US008329164B2

(12) United States Patent
Kirn et al.

(10) Patent No.: US 8,329,164 B2
(45) Date of Patent: Dec. 11, 2012

(54) METHODS AND COMPOSITIONS CONCERNING POXVIRUSES AND CANCER

(75) Inventors: David Kirn, Mill Valley, CA (US); Steve H. Thorne, Palo Alto, CA (US)

(73) Assignee: Jennerex, Inc., San Francisco, CA (US)

(*) Notice: Subject to any disclaimer, the term of this patent is extended or adjusted under 35 U.S.C. 154(b) by 0 days.

(21) Appl. No.: 11/838,757

(22) Filed: Aug. 14, 2007

(65) Prior Publication Data

US 2009/0004723 A1 Jan. 1, 2009

Related U.S. Application Data

(63) Continuation of application No. 10/524,932, filed as application No. PCT/US03/25141 on Aug. 11, 2003, now abandoned.

(60) Provisional application No. 60/402,857, filed on Aug. 12, 2002.

(51) Int. Cl.
*A61K 39/275* (2006.01)
*C12N 7/01* (2006.01)

(52) U.S. Cl. .................................... 424/93.3; 435/235.1

(58) Field of Classification Search ........................ None
See application file for complete search history.

(56) References Cited

U.S. PATENT DOCUMENTS

| | | | |
|---|---|---|---|
| 5,151,509 A | 9/1992 | Kotwal et al. | 536/23.2 |
| 5,656,465 A | 8/1997 | Panicali et al. | 435/456 |
| 5,739,169 A | 4/1998 | Ocain et al. | 514/658 |
| 5,762,938 A | 6/1998 | Paoletti et al. | 424/199.1 |
| 5,801,005 A | 9/1998 | Cheever et al. | 435/7.24 |
| 5,824,311 A | 10/1998 | Greene et al. | 424/138.1 |
| 5,830,880 A | 11/1998 | Sedlacek et al. | 514/44 |
| 5,846,945 A | 12/1998 | McCormick | 514/44 |
| 5,871,740 A | 2/1999 | Smith | 424/186.1 |
| 5,969,094 A * | 10/1999 | Compans et al. | 530/324 |
| 6,093,700 A | 7/2000 | Mastrangelo et al. | 514/44 |
| 6,177,076 B1 | 1/2001 | Lattime et al. | 424/93.6 |
| 6,265,189 B1 | 7/2001 | Paoletti et al. | 435/70.1 |
| 6,355,252 B1 | 3/2002 | Smith et al. | 424/232.1 |
| 6,475,999 B1 | 11/2002 | Mastrangelo et al. | 514/44 |
| 6,521,449 B1 | 2/2003 | Polack et al. | 435/320.1 |
| 7,208,313 B2 | 4/2007 | McCart et al. | 435/320.1 |
| 2003/0025141 A1 | 2/2003 | Grimm | 257/301 |
| 2003/0086906 A1 | 5/2003 | Mastrangelo et al. | 424/93.2 |
| 2003/0206886 A1 | 11/2003 | Lattime et al. | 424/93.2 |
| 2004/0091995 A1 | 5/2004 | Schlom et al. | 435/235.1 |
| 2005/0031643 A1 | 2/2005 | Szalay et al. | 424/199.1 |
| 2006/0051370 A1 | 3/2006 | Szalay et al. | 424/199.1 |
| 2007/0025981 A1 | 2/2007 | Szalay et al. | 424/130.1 |
| 2007/0065411 A1 | 3/2007 | Kirn | 424/93.2 |
| 2008/0286237 A1 | 11/2008 | Kirn | 435/6 |

FOREIGN PATENT DOCUMENTS

| | | |
|---|---|---|
| CA | 2105277 | 9/1992 |
| CA | 2305269 | 4/1999 |
| CA | 2370187 | 10/2000 |
| CA | 2388807 | 5/2001 |
| CA | 2375189 | 2/2010 |
| WO | WO 99/29343 | 6/1999 |
| WO | WO 00/62735 | 10/2000 |
| WO | WO 00/73479 | 12/2000 |
| WO | WO 2004/014314 | 2/2004 |

OTHER PUBLICATIONS

McIntosh et al. J. Virol. 1996, vol. 70, No. 1, pp. 272-281.*
Mogiez-Hellin et al. Proc. Natl. Acad. Sci. USA, 1996, vol. 93, pp. 4175-4180.*
Blasco et al. J. Virol. 1993, vol. 67, pp. 3319-3325.*
Blasco et al. J. Virol. 1992, vol. 66, No. 7, pp. 4170-4179.*
Payne et al. Journal of Virology, 1979, vol. 31, No. 1, pp. 147-155.*
Payne L. Journal of Virology, 1979, vol. 31, No. 4, pp. 147-155.*
Extended European Search Report, issued in European Patent Application No. 08167984.7, dated Mar. 6, 2009.
Broyles et al., "Antiviral activity of distamycin A against vaccinia virus is the result of inhibition of postreplicative mRNA synthesis," *Journal of Virology*, 78(4):2137-2141, 2004.
Legrand et al., "Vaccinia viruses with a serpin gene deletion and expressing IFN-γ induce potent immune responses without detectable replication in vivo," *PNAS*, 102(8):2940-2945, 2005.
Office Communication, issued in European Application No. 06 814 307.2, dated Mar. 19, 2009.
Office Communication, issued in U.S. Appl. No. 10/524,932, dated Jan. 2, 2008.
Office Communication, issued in U.S. Appl. No. 10/524,932, dated Apr. 15, 2008.
Office Communication, issued in U.S. Appl. No. 10/524,932, dated Oct. 24, 2008.
Thorne et al., "Rational strain selection and engineering creates a broad spectrum, systemically effective oncolytic poxvirus, JX-963," *The Journal of Clinical Investigation*, 117(11):3350-3358, 2007.
Office Action issued in European Application No. 08167984.7, mailed Sep. 10, 2009.
Office Communication, issued in Japanese Patent Application No. 2004-528045, dated Jul. 6, 2009.
Office Communication, issued in Japanese Patent Application No. 2004-528045, dated May 26, 2010. (English translation).
Vanderplasschen and Smith, "A novel virus binding assay using confocal microscopy: demonstration that the intracellular and extracellular vaccinia virions bind to different cellular receptors," *J. Virol.*, 71(5):4032-4041, 1997.
Vanderplasschen and Smith, "Intracellular and extracellular vaccinia virions enter cells by different mechanisms," *J. Gen. Virol.*, 79(Part 4):877-887, 1998.

(Continued)

*Primary Examiner* — Bao Li
(74) *Attorney, Agent, or Firm* — Morgan, Lewis & Bockius LLP

(57) ABSTRACT

The present invention concerns methods and compositions for the treatment of cancer and cancer cells using altered poxviruses, including a vaccinia virus that has been altered to generate a more effective therapeutic agent. Such poxviruses are engineered to be attenuated or weakened in their ability to affect normal cells. In some embodiments, methods and compositions involve poxviruses that possess mutations that result in poxviruses with diminished or eliminated capability to implement an antiviral response in a host. Poxviruses with these mutations in combination with other mutations can be employed for more effective treatment of cancer.

9 Claims, 10 Drawing Sheets

OTHER PUBLICATIONS

Office Communication issued in corresponding Canadian Patent Application No. 2,494,844 mailed Jul. 22, 2010.
Sinkovics, "New Developments in the Virus Therapy of Cancer: A Historical Review," *Intervirology*, 36:193-214, 1993.
Kurata et al., "Recombinant adenovirus vectors for cytokine gene therapy in mice," *J. Allergy Clin. Immunol.*, 103(5 Pt. 2):S471-484, 1999.
Office Action issued in U.S. Appl. No. 11/470,951, mailed Apr. 1, 2008.
Office Action issued in U.S. Appl. No. 11/470,951, mailed Aug. 16, 2010.
Office Action issued in U.S. Appl. No. 11/470,951, mailed Apr. 26, 2007.
Office Action issued in U.S. Appl. No. 11/470,951, mailed Jul. 6, 2009.
Office Action issued in U.S. Appl. No. 11/470,951, mailed Jul. 11, 2007.
Office Action issued in U.S. Appl. No. 11/470,951, mailed Oct. 15, 2008.
Office Action issued in U.S. Appl. No. 11/838,774, mailed Jul. 6, 2010.
Office Action issued in U.S. Appl. No. 11/838,774, mailed May 19, 2009.
Office Action issued in U.S. Appl. No. 11/838,774, mailed Nov. 19, 2009.
Peplinski et al., "In vivo gene therapy of a murine pancreas tumor with recombinant vaccinia virus encoding human interleukin-1beta," Surgery, 118:185-191, 1995.
Perera et al., "Comparative assessment of virulence of recombinant vaccinia viruses expressing IL-2 and IL-15 in immunodeficient mice," PNAS, 98(9):5146-5151, 2001.
Extended European Search Report issued in European Patent Application No. 10181820.1, dated Dec. 7, 2010.
Extended European Search Report issued in European Patent Application No. 10181845.8, dated Dec. 3, 2010.
Office Communication, issued in Australian Patent Application No. 2006287441, dated May 6, 2011.
Office Communication, issued in Chinese Patent Application No. 201010158338.1, dated May 3, 2011. (English translation).
Office Communication, issued in Chinese Patent Application No. 200680041389.8, dated Jun. 10, 2011. (English translation).
Office Communication, issued in European Patent Application No. 08 167 984.7, dated Nov. 3, 2010.
Office Communication, issued in European Patent Application No. 06 814 307.2, dated Mar. 8, 2011.
Office Communication, issued in U.S. Appl. No. 11/838,757, dated Dec. 13, 2010.
Adams et al., "Clinical studies of human papilloma vaccines in pre-invasive and invasive cancer," *Vaccine*, 19(17-19):2549-56, 2001.
Alcami and Smith, "A soluble Receptor for Interleukin-1 beta encoded by Vaccinia Virus: A Novel Mechanism of Virus Modulation of the Host Response to Infection," *Cell*, 71(1):153-67, 1992.
Alcami and Smith., "The vaccinia virus soluble interferon-gamma receptor is a homodimer," *J Gen Virol.*, 83(Pt 3):545-9, 2002.
Alcami et al., "Poxviruses: Capturing Cytokines and Chemokines," *Sem Virol*, 5:419-427, 1998.
Alcami et al., "The vaccinia virus soluble alpha/beta interferon (IFN) receptor bnds to the cell surface and protects cells from the aniviral effect of IFN," *J Virology*, 74(23):11230-11239, 2000.
Alcami et al., "Vaccinia virus strains Lister, USSR and Evans express soluble and cell-surface tumour necrosis factor receptors," *J Gen Virol*, 80(Pt 4):949-59, 1999.
Alimonti et al., "TAP expression provides a general method for improving the recognition of malignant cells in vivo," *Nature Biotech*, 18(5):515-520, 2000.
Andoh et al., "Sodium butyrate enhances complement-mediated cell injury via down-regulation of decay-accelerating factor expression in colonic cancer cells," *Cancer Immunol Immunother*, 50(12):663-672, 2002.

Arakawa et al., "Clinical trial of attenuated vaccinia virus AS strain in the treatment of advanced adenocarcinoma," *J Cancer Res Clin Oncol*, 113:95-98, 1987.
Austin-Ward and Villaseca, "Gene therapy and its applications," *Rev Med Chil*, 126(7):838-845, 1998.
Bartlett et al., "The vaccinia virus N1L protein is an intracellular homodimer that promotes virulence," *J. Gen. Virol.*, 83:1965-1976, 2002.
Berwin et al., "Virally induced lytic cell death elicits the release of immunogenic GRP94/gp96," *J Biol Chem*, 276(24):21083-8, 2001.
Blanchard et al., "Modified vaccinia virus Ankara undergoes limited replication in human cell and lacks several immunomodulatory proteins: implications for use as a human vaccine," *J Gen Virol.*, 79(Pt 5):1159-67, 1998.
Blanchard et al., "Vaccinia virus strain modified virus ankara: characterization of cytokine receptor profile, virological features, and use as an immunological reagent," *Conf Adv AIDS Vaccine Dev*, 108 (Poster 3): May 4-7, 1997. (Abstract).
Blasco and Moss, "Role of cell-associated enveloped vaccinia virus in cell-to-cell spread," *J Virology*, 66(7):4170-4179, 1992.
Blasco et al., "Dissociation of progeny vaccinia virus from the cell membrane is regulated by a viral envelope glycoprotein: effect of a point mutation in the lectin homology domain of the A34R gene," *J Virology*, 67(6):3319-3325, 1993.
Bowie et al., "A46R and A52R from vaccinia virus are antagonist of host IL-1 and toll-like receptor signaling," *Proc Natl Acad Sci USA*, 97(18):10162-10167, 2000.
Boyd et al., "Adenovirus E1B 19 kDa and Bcl-2 proteins interact with a common set of cellular proteins," *Cell*, 79:341-351, 1994.
Bukowski et al., "Signal transduction abnormalities in T lymphocytes from patients with advanced renal carcinoma: clinical relevance and effects of cytokine therapy," *Clin Cancer Res*, 4(10):2337-2347, 1998.
Buller and Palumbo, "Poxvirus Pathogenesis," *Microbiol Rev*, 55:80-122, 1991.
Burke, "Cytokines (IFNs, TNF-alpha, IL-2 and IL-12) and animal models of cancer," *Cytokines Cell Mol Ther*, 5(1):51-61, 1999.
Cantrell et al., "Cloning, sequence, and expression of a human granulocyte/macrophage colony-stimulating factor," *Proc. Natl Acad. Sci. USA*, 82:6250-6254, 1985.
Caragine et al., "A tumor-expressed inhibitor of the early but not late complement lytic pathway enhances tumor growth in a rat model of human breast cancer," *Cancer Res*, 62(4):1110-1115, 2002.
Chen et al., "Low-dose vaccinia virus-mediated cytokine gene therapy of glioma," *J Immunother*, 24:46-57, 2001.
Christodoulides et al., "Immunization with recombinant class 1 outer-membrane protein from *Neisseria meningitidis*: influence of liposomes and adjuvants on antibody avidity, recognition of native protein and the induction of a bactericidal immune response against meningococci," *Microbiology*, 144(Pt 11):3027-3037, 1998.
Colamonici et al., "Vaccinia virus B18R gene encodes a type I interferon-binding protein that blocks interferon alpha transmembrane signaling," *J Biol Chem*, 270:15974-15978, 1995.
Cunnion, "Tumor necrosis factor receptors encoded by poxviruses," *Mol Genet Metab*, 67(4):278-82, 1999.
Davidson et al., "Intralesional cytokine therapy in cancer: a pilot study of GM-CSF infusion in mesothelioma," *J Immunother*, 21(5):389-398, 1998.
Dobbelstein and Shenk, "Protection against apoptosis by the vaccinia virus SPI-2 (B13R) gene product," *J Virology*, 70:6479-6485, 1996.
Doehn amd Jocham, "Technology evaluation: TG-1031, Transgene SA," *Curr Opin Mol Ther*, 106-11, 2000.
Dranoff et al., "Vaccination with irradiated tumor cells engineered to secrete murine granulocyte-macrophage colony-stimulating factor stimulates potent, specific, and long-lasting anti-tumor immunity," *Proc. Natl. Acad. Sci. USA*, 90:3539-3543, 1993.
Durrant and Spendlove, "Immunization against tumor cell surface complement-regulatory proteins," *Curr Opin Investig Drugs*, 2(7):959-966, 2001.
Eliopoulos et al., "The control of apoptosis and drug resistance in ovarian cancer: influence of p53 and Bcl-2," *Oncogene*, 11(7):1217-1228, 1995.

Feng et al., "Induction of CD8+ T-lymphocyte responses to a secreted antigen of Mycobacterium tuberculosis by an attenuated vaccinia virus," *Immunol Cell Biol.*, 79(6):569-75, 2001.

Gardner et al., "Vaccinia virus semaphorin A39R is a 50-55 kDa secreted glycoprotein that affects the outcome of infection in a murine intradermal model," *J Gen Virol.*, 82(Pt 9):2083-93, 2001.

Gnant et al., "Systemic administration of a recombinant vaccinia virus expressing the cytosine deaminase gene and subsequent treatment with 5-fluorocytosine leads to tumor-specific gene expression and prolongation of survival in mice," *Cancer Res*, 59(14):3396-3403, 1999.

Goebel et al., "The complete DNA sequence of vaccinia virus," *Virology*, 179(1):247-266 and 517-563, 1990.

Gomella et al., "Phase i study of intravesical vaccinia virus as a vector for gene therapy of bladder cancer," *J Urol*, 166:1291-5, 2001.

Graham et al., "The T1/35kDa Family of Poxvirus-Secreted Proteins Bind Chemokines and Modulate Leukocyte Influx to Virus-Infected Tissues," *Virology*, 229(1):12-24, 1997.

Gross et al., "BCL-2 family members and the mitochondria in apoptosis," *Genes Dev*, 13(15):1899-1911, 1999.

Hanibuchi et al., "Therapeutic efficacy of mouse-human chimeric anti-ganglioside GM2 monoclonal antibody against multiple organ micrometastases of human lung cancer in NK cell-depleted SCID mice," *Int J Cancer*, 78(4):480-485, 1998.

Hawkins et al., "Oncolytic biotherapy: a novel therapeutic plafform," *Lancet Oncol*, 3(1):17-26, 2002.

He et al., "Viral recombinant vaccines to the E6 and E7 antigens of HPV-16," *Virology*, 270(1):146-161, 2000.

Heise et al., "Efficacy of a replication-competent adenovirus (ONYX-015) following intratumoral injection: intratumoral spread and distribution effects," *Cancer Gene Ther*, 6(6):499-504, 1999.

Heise et al., "ONYX-015, an E1b gene-attenuated adenovirus, causes tumor-specific cytolysis and antitumoral efficacy that can be augmented by standard chemotherapeutic agents," *Nat Med*, 3:639-45, 1997.

Hellstrand et al., "Histamine and cytokine therapy," *Acta Oncol*, 37(4):347-353, 1998.

Hermiston, "Gene delivery from replication-selective viruses: arming guided missiles in the war against cancer," *J Clin Invest*, 105:1169-1172, 2000.

Holzer et al., "Highly efficient induction of protective immunity by a vaccinia virus vector defective in late gene expression," *Journal of Virology*, 73(6):4536-4542, 1999.

Homey et al., "Chemokines: Agents for the Immunotherapy of Cancer?," *Nature Rev Immunol*, 2:175-184, 2002.

Hui and Hashimoto, "Pathways for potentiation of immunogenicity during adjuvant-assisted immunizations with *Plasmodium falciparum* major merozoite surface protein 1," *Infect Immun*, 66(11):5329-5336, 1998.

Ikeda et al., "Oncolytic virus therapy of multiple tumors in the brain requires suppression of innate and elicited antiviral responses," *Nat Med*, 5(8):881-887, 1999.

Isaacs et al., "Vaccinia virus complement-control protein prevents antibody-dependent complement-enhanced neutralization of infectivity and contributes to virulence," *Proc. Natl. Acad. Sci. USA*, 89(2):628-32, 1992.

Kantor et al., "Antitumor activity and immune responses induced by a recombinant carcinoembryonic antigen-vaccinia virus vaccine," *J Natl Cancer Inst*, 84(14):1084-1091, 1992.

Kawakita et al., "Poxvirus vectors for gene transfer," *Acta Urologica Japonica*, 43(11):835-838, 1997.

Kay et al., "Transient immunomodulation with anti-CD40 ligand antibody and CTLA41g enhances persistence and secondary adenovirus-mediated gene transfer into mouse liver," *Proc Natl Acad Sci USA*, 97(9):4686-4691, 1997.

Kette, "Vaccinia virus serpin B12R (SPI-2) inhibits interleukin 1-beta converting enzyme and protects virus-infected cells from TNF- and Fas-mediated apoptosis, but does not prevent IL-1-beta induced fever," *J Gen. Vir.*, 78:677-685, 1997.

Kim et al., "167. Both Oncolysis and Tumor Immunity Are Involved in an Antitumoral Efficacy by Intratumoral Injection of Recombinant Vaccinia Virus (TK Deleted, hGM-CSF Inserted Wyeth Strain) in a VX2 Rabbit Model," *Mol. Therapy*, 11:67, 2005.

Kim et al., "Systemic Armed Oncolytic and Immunologic Therapy for Cancer with JX-594, a Targeted Poxvirus Expressing GM-CSF," *Mol Ther*, 14:361-70, 2006.

Kirn et al., "Replication-selective virotherapy for cancer: biological principles, risk management and future direction," *Nat Med*, 7(7):781-787, 2001.

Kirn et al., "Systemic Oncolytic and Immunologic Therapy for Cancer with JX-594, a Targeted Poxvirus Expressing GM-CSF," *Mol. Ther.*, 13:S244-S245, 2006.

Kirn et al., "The emerging fields of suicide gene therapy and virotherapy," *Trends Mol Med*, 8(4):S68-S73, 2002.

Law et al., "Antibody-sensitive and antibody-resistant cell-to-cell spread by vaccinia virus: role of the A33R protein in antibody-resistant spread," *J Gen Virol.*, 83(Pt 1):209-22, 2002.

Lee et al., "406. Enhancedc Vaccinia-meditated Antitumor Response after Specific Inhibiton of the Cellular Immune Response," *Mol. Ther.*, 1:S156-S157, 2000.

Loparev et al., "A third distinct tumor necrosis factor receptor of orthopoxviruses," *Proc Natl Acad Sci USA*, 95:3789-3791, 1998.

Marshall et al., "Phase I study in advanced cancer patients of a diversified prime-and-boost vaccination protocol using recombinant vaccinia virus and recombinant nonreplicating avipox virus to elicit anti-carcinoembryonic antigen immune responses," *J Clin Oncol*, 18(23):3964-73, 2000.

Mastrangelo and Lattime, "Virotherapy clinical trials for regional disease: in situ immune modulation using recombinant poxvirus vectors," *Cancer Gene Ther.*, 9:1013-1021, 2002.

Mastrangelo et al., "Intralesional Vaccinia/GM-CSF Recombinant Virus in the Treatment of Metastatic Melanoma," *Adv. Exp. Med. Biol.*, 465:391-400, 2000.

Mastrangelo et al., "Intratumoral recombinant GM-CSF-encoding virus as gene therapy in patients with cutaneous melanoma," *Cancer Gene Ther.*, 6:409-422, 1999.

Mathew et al., "A mutational analysis of the vaccinia virus B5R protein," *J Gen Virol.*, 82(Pt 5):1199-213, 2001.

McCart et al., "Complex interactions between the replicating oncolytic effect and the enzyme/prodrug effect of vaccinia-mediated tumor regression," *Gene Ther*, 7(14):1217-1223, 2000.

McCart et al., "Systemic cancer therapy with a tumor-selective vaccinia virus mutant lacking thymidine kinase and vaccinia growth factor genes," *Cancer Res.*, 61:8751-8757, 2001.

McFadden and Murphy, "Host-related immunomodulators encoded by poxviruses and herpesviruses," *Curr Opin Microbiol*, 3(4):371-8, 2000.

McIntosh and Smith, "Vaccinia virus glycoprotein A34R is required for infectivity of extracellular enveloped virus," *J. Virol.*, 70:272-281, 1996.

Moss, "Poxviridae and Their Replication," In: *Fields Virology*, Fields et al. (ed.), Raven Publ, New York, pp. 953-985, 1996.

Mossman et al., "Myxoma virus M-T7, a secreted homolog of the interferon-gamma receptor, is a critical virulence factor for the development of myxomatosis in European rabbits," *Virology*, 215(1):17-30, 1996.

Mukherjee et al., "Replication-restricted vaccinia as a cytokine gene therapy vector in cancer: persistent transgene expression despite antibody generation," *Cancer Gene Ther*, 7(5):663-670, 2000.

Mullen and Tanabe, "Viral Oncolysis 2002," *The Oncologist*, 7:106-119, 2002.

Ng et al., "The vaccinia virus A41L protein is a soluble 30 kDa glycoprotein that affects virus virulence," *J Gen Virol.*, 82(Pt 9):2095-105, 2001.

Nielsen et al., "Adenovirus-mediated p53 gene therapy and paclitaxel have synergistic efficacy in models of human head and neck, ovarian, prostate, and breast cancer," *Clin Cancer Res*, 4(4):835-846, 1998.

Nielsen et al., "Adenovirus-mediated p53 therapy synergizes with paclitaxel against human ovarian, mammary, prostate, head and neck, and liver cancer," *Cancer Gene Therapy*, 4(6):S12, 1997.

Parato et al., "Recent Progress in the Battle between Oncolytic Viruses and Tumours," *Nat Rev Cancer*, 5, 965-76, 2005.

Pietras et al., "Remission of human breast cancer xenografts on therapy with humanized monoclonal antibody to HER-2 receptor and DNA-reactive drugs," *Oncogene*, 17(17):2235-2249, 1998.

Price et al. "The vaccinia virus B9R protein is a 6 kDa intracellular protein that is non-essential for virus replication and virulence," *J Gen Virol.*, 83(Pt 4):873-8, 2002.
Price et al., "Vaccinia virus gene B7R encodes an 18-kDa protein that is resident in the endoplasmic reticulum and affects virus virulence," *Virology*, 1;267(1):65-79, 2000.
Puhlmann et al., "Thymidine Kinase-Deleted Vaccinia Virus Expressing Purine Nucleoside Phosphorylase as a Vector for Tumor-Directed Gene Therapy," *Hum Gene Ther.*, 10: 649-57, 1999.
Puhlmann et al., "Vaccinia as a vector for tumor-directed gene therapy: biodistribution of a thymidine kinase-deleted mutant," *Cancer Gene Ther*, 7(1):66-73, 2000.
Qin et al., "Interferon-beta gene therapy inhibits tumor formation and causes regression of established tumors in immune-deficient mice," *Proc Natl Acad Sci USA*, 95(24):14411-14416, 1998.
Reading et al., "Vaccinia virus CrmE encodes a soluble and cell surface tumor necrosis factor receptor that contributes to virus virulence," *Virology*, 292(2):285-98, 2002.
Rosel et al., "Conserved TAAATG sequence a the transcriptional and translational initiation sites of vaccinia virus late genes deduced by structural and functional analysis of the HindIII H genome fragment," *J Virology*, 60(2):436-449, 1986.
Saraiva and Alcami, "CrmE, a novel soluble tumor necrosis factor receptor encoded by poxviruses," *J Virol*, 75(1):226-233, 2001.
Scholl et al., "Recombinant vaccinia virus encoding human MUC1 and IL2 as immunotherapy in patients with breast cancer," *J Immunother*, 23:570-80, 2000.
Seet et al., "Molecular determinants for CC-chemokine recognition by a poxvirus CC-chemokine inhibitor," *Proc Natl Acad Sci USA*, 98(16):9008-9013, 2001.
Siemens et al., "Comparison of gene transfer and expression of viral vectors in an orthotopic murine bladder cancer model," *Journal of Urology*, 170(3):979-84, 2003.
Sinkovics and Horvath, "Newcastle disease virus (NDV): brief history of its oncolytic strains," *J Clin Viro*, 16:1-15, 2000.
Smith and Vanderplasschen, "Extracellular enveloped vaccinia virus," *Adv Exp Med Biol*, 440:395-414, 1998.
Smith et al., "Ectromelia, vaccinia and cowpox viruses encode secreted interleukin-18-binding proteins," *J. Gen. Virol.*, 81:1223-1230, 2000.
Smith et al., "Lethality-based selection of recombinant genes in mammalian cells: application to identifying tumor antigens," *Nat Med*, 967-72, 2001.
Smith et al., "Vaccinia virus immune evasion," *Immunol Rev*, 159:137-154, 1997.
Smith, "Vaccinia virus immune evasion," *Immunol Lett.*, 65(1-2):55-62, 1999.
Spehner et al. "Enveloped virus is the major virus form produced during productive infection with the modified vaccinia virus Ankara strain," *Virology*, 273(1):9-15, 2000.
Spriggs et al., "Vaccinia and Cowpox Viruses Encode a Novel Secreted Interleukin-1-Binding Protein," *Cell*, 71(1):145-152, 1992.
Sroller, "Effect of IFN-gamma receptor gene deletion on vaccinia virus virulence," *Arch. Virol.*, 146:239-249, 2001.
Symons et al., "A study of the vaccinia virus interferon-gamma receptor and its contribution to virus virulence," *J Gen. Virol.*, 83:1953-1964, 2002.
Symons et al., "The vaccinia virus C12L protein inhibits mouse IL-18 and promotes virus virulence in the murine intranasal model," *J. Gen. Virol.*, 83:2833-2844, 2002.

Symons et al., "Vaccinia virus encodes a soluble type I interferon receptor of novel structure and broad species specificity," *Cell*, 81:551-560, 1995.
Thorne and Kirn, "Future directions of the field oncolytic virotherapy: a perspective on the use of vaccinia virus," *Expert Opinion Biol. Ther.*, 4:1307-1321, 2004.
Thorne et al., "169. The Creation of Novel Oncolytic Vaccinia Virus Vectors for Efficient Systemic Delivery of Transgenes to Tumors," *Mol. Ther.*, 11:67, 2005.
Thorne et al., "Rational Strain Selection and Engineering Creates a Broad Spectrum Systemically Effective Oncolytic Poxvirus JX-963," *Article in Press*, 2007.
Thorne et al., "The Use pf Oncolytic Vaccinia Viruses in the Treatment of Cancer: A New Role for an Old Ally?," *Current Gene Therapy*, 5:429-443, 2005.
Timiryasova et al., "Antitumor effect of vaccinia virus in glioma model," *Oncol Res*, 11:133-144, 1999.
Todo et al., "In situ expression of soluble B7-1 in the context of oncolytic herpes simplex virus induces potent antitumor immunity," *Cancer Res*, 61:153-161, 2001.
Trevor et al., "Transduction of human dendritic cells with a recombinant modified vaccinia Ankara virus encoding MUC1 and IL-2," *Cancer Immunology Immunotherapy*, 50(8):397-407, 2001.
Tscharke et al., "Dermal infection with vaccinia virus reveals roles for virus proteins not seen using other inoculation routes," *J. Gen. Virol.*, 83:1977-1986, 2002.
Upton et al., "Encoding of a Homolog of the IFN-γ Receptor by Myxoma Virus," *Science*, 258:1369-1372, 1992.
Upton et al., "Myxoma Virus Expresses a Secreted Protein with Homology to the Tumor Necrosis Factor Receptor Gene Family That Contributes to Viral Virulence," *Virology*, 184(1):370-382, 1991.
Vanderplasschen et al., "Extracellular enveloped vaccinia virus is resistant to complement because of incorporation of host complement control proteins into its envelope," *Proc Natl Acad Sci USA*, 95(13):7544-7549, 1998.
Verardi et al., "Vaccinia virus vectors with a inactivated gamma interferon receptor homolog gen (B8R) are attenuated in vivo without a concomitant reduction in immunogenicity," *J Virol*, 75(1):11-18, 2001.
Vicari and Caux, "Chemokines in cancer," *Cytokine Growth Factor Rev*, 13:143-154, 2002.
Weijer et al., "Histopathology of tumor regression after intralesional injection of *Mycobacterium bovis.*, 2. Comparative effects of vaccinia virus, oxazolone, and turpentine," *J Natl Cancer Inst*, 48:1697-707, 1972.
Wold et al., "Adenovirus proteins that subvert host defenses," *Trends Microbiol*, 2:437-443, 1994.
Wolffe et al., "Deletion of the vaccinia virus B5R gene encoding a 42-kilodalton membrane glycoprotein inhibits extracellular virus envelope formation and dissemination," *J. Virol.*, 67,4732-4741, 1993.
Xiang et al., "Blockade of interferon induction and action by the E3L double-stranded RNA binding proteins of vaccinia virus," *J Virol*, 76(10):5251-9, 2002.
Xu et al., "Myxoma virus expresses a TNF receptor homolog with two distinct functions," *Virus Genes*, 21(I-2):97-109, 2000.

\* cited by examiner

METHODS AND COMPOSITIONS CONCERNING POXVIRUSES AND CANCER

This application is a continuation of U.S. patent application Ser. No. 10/524,932 filed Jan. 4, 2006 now abandoned, which is a national phase application under 35 U.S.C. §371 of International Application No. PCT/US2003/025141 filed 11 Aug. 2003, which claims priority to U.S. Provisional Application No. 60/402,857 filed 12 Aug. 2002. The entire text of each of the above-referenced disclosures is specifically incorporated by reference herein without disclaimer.

BACKGROUND OF THE INVENTION

1. Field of the Invention

The present invention relates generally to the fields of oncology and virology. More particularly, it concerns poxviruses, specifically including vaccinia viruses, that comprise one or more mutations rendering them particularly suitable for the treatment of cancer.

2. Description of Related Art

Normal tissue homeostasis is a highly regulated process of cell proliferation and cell death. An imbalance of either cell proliferation or cell death can develop into a cancerous state (Solyanik et al., 1995; Stokke et al, 1997; Mumby and Walter, 1991; Natoli et al., 1998; Magi-Galluzzi et al., 1998). For example, cervical, kidney, lung, pancreatic, colorectal and brain cancer are just a few examples of the many cancers that can result (Erlandsson, 1998; Kolmel, 1998; Mangray and King, 1998; Gertig and Hunter, 1997; Mougin et al., 1998). In fact, the occurrence of cancer is so high that over 500,000 deaths per year are attributed to cancer in the United States alone.

The maintenance of cell proliferation and cell death is at least partially regulated by proto-oncogenes and tumor suppressors. A proto-oncogene or tumor suppressor can encode proteins that induce cellular proliferation (e.g., sis, erbB, src, ras and myc), proteins that inhibit cellular proliferation (e.g., Rb, p16, p19, p21, p53, NF1 and WT1) or proteins that regulate programmed cell death (e.g., bcl-2) (Ochi et al., 1998; Johnson and Hamdy, 1998; Liebermann et al., 1998). However, genetic rearrangements or mutations of these proto-oncogenes and tumor suppressors result in the conversion of a proto-oncogene into a potent cancer-causing oncogene or of a tumor suppressor into an inactive polypeptide. Often, a single point mutation is enough to achieve the transformation. For example, a point mutation in the p53 tumor suppressor protein results in the complete loss of wild-type p53 function (Vogelstein and Kinzler, 1992.

Currently, there are few effective options for the treatment of many common cancer types. The course of treatment for a given individual depends on the diagnosis, the stage to which the disease has developed and factors such as age, sex and general health of the patient. The most conventional options of cancer treatment are surgery, radiation therapy and chemotherapy. Surgery plays a central role in the diagnosis and treatment of cancer. Typically, a surgical approach is required for biopsy and to remove cancerous growth. However, if the cancer has metastasized and is widespread, surgery is unlikely to result in a cure and an alternate approach must be taken. Radiation therapy, chemotherapy and immunotherapy are alternatives to surgical treatment of cancer (Mayer, 1998; Ohara, 1998; Ho et al., 1998). Radiation therapy involves a precise aiming of high energy radiation to destroy cancer cells and much like surgery, is mainly effective in the treatment of non-metastasized, localized cancer cells. Side effects of radiation therapy include skin irritation, difficulty swallowing, dry mouth, nausea, diarrhea, hair loss and loss of energy (Curran, 1998; Brizel, 1998).

Chemotherapy, the treatment of cancer with anti-cancer drugs, is another mode of cancer therapy. The effectiveness of a given anti-cancer drug therapy often is limited by the difficulty of achieving drug delivery throughout solid tumors (el-Kareh and Secomb, 1997). Chemotherapeutic strategies are based on tumor tissue growth, wherein the anti-cancer drug is targeted to the rapidly dividing cancer cells. Most chemotherapy approaches include the combination of more than one anti-cancer drug, which has proven to increase the response rate of a wide variety of cancers (U.S. Pat. No. 5,824,348; U.S. Pat. No. 5,633,016 and U.S. Pat. No. 5,798, 339, incorporated herein by reference). A major side effect of chemotherapy drugs is that they also affect normal tissue cells, with the cells most likely to be affected being those that divide rapidly in some cases (e.g., bone marrow, gastrointestinal tract, reproductive system and hair follicles). Other toxic side effects of chemotherapy drugs can include sores in the mouth, difficulty swallowing, dry mouth, nausea, diarrhea, vomiting, fatigue, bleeding, hair loss and infection.

Immunotherapy, a rapidly evolving area in cancer research, is yet another option for the treatment of certain types of cancers. Theoretically, the immune system may be stimulated to identify tumor cells as being foreign and targets them for destruction. Unfortunately, the response typically is not sufficient to prevent most tumor growth. However, recently there has been a focus in the area of immunotherapy to develop methods that augment or supplement the natural defense mechanism of the immune system. Examples of immunotherapies currently under investigation or in use are immune adjuvants (e.g., *Mycobacterium bovis*, *Plasmodium falciparum*, dinitrochlorobenzene and aromatic compounds) (U.S. Pat. No. 5,801,005; U.S. Pat. No. 5,739,169; Hui and Hashimoto, 1998; Christodoulides et al., 1998), cytokine therapy (e.g., interferons (IL-1, GM-CSF and TNF) Bukowski et al., 1998; Davidson et al., 1998; Hellstrand et al., 1998), and gene therapy (e.g., TNF, IL-1, IL-2, p53) (Qin et al., 1998; Austin-Ward and Villaseca, 1998; U.S. Pat. No. 5,830,880 and U.S. Pat. No. 5,846,945) and monoclonal antibodies (e.g., anti-ganglioside GM2, anti-HER-2, anti-p185) (Pietras et al., 1998; Hanibuchi et al., 1998; U.S. Pat. No. 5,824,311). Such methods, while showing some promise, have demonstrated limited success.

Replication-selective oncolytic viruses hold promise for the treatment of cancer (Kirn et al., 2001). These viruses can cause tumor cell death through direct replication-dependent and/or viral gene expression-dependent oncolytic effects (Kirn et al., 2001). In addition, viruses are able to enhance the induction of cell-mediated antitumoral immunity within the host (Todo et al., 2001; Sinkovics et al., 2000). These viruses also can be engineered to expressed therapeutic transgenes within the tumor to enhance antitumoral efficacy (Hermiston, 2000).

However, major limitations exist to this therapeutic approach. Although a degree of natural tumor-selectivity can be demonsated for some virus species, new approaches are still needed to engineer and/or enhance tumor-selectivity for oncolytic viruses in order to maximize safety. This selectivity will become particularly important when intravenous administration is used, and when potentially toxic therapeutic genes are added to these viruses to enhance antitumoral potency; gene expression will need to be tightly limited in normal tissues. In addition, increased antitumoral potency through additional mechanisms such as induction of antitumoral immunity or targeting of the tumor-associated vasculature is highly desirable.

Therefore, more effective and less toxic therapies for the treatment of cancer are needed. The use of oncolytic viruses presents an area that can be developed, however, the limitation discussed above need to be overcome. Thus, the present invention addresses those limitations.

SUMMARY OF THE INVENTION

The present invention is based on the discovery that poxviruses can be altered 1) to generate an agent that differentially affects different cell populations or tissue types and/or 2) to generate a form of poxviruses that is more infectious and capable of infecting other cells by virtue of improved release from an infected cell. The poxviruses of the invention, e.g., the copenhagen strain of vaccinia virus, may act synergistically with other therapies (e.g. chemotherapy) and provide beneficial effects by targeting tumor vasculature while not opposing or inhibiting TNF and/or INF pathways. It is specifically contemplated that vaccinia virus of any strain may be used. In certain embodiments, the Copenhagen strain of vaccinia virus, or a derivative thereof, is also contemplated.

In some embodiments, the poxvirus may be more toxic or therapeutically efficient with respect to the targeted cells, while being relatively innocuous to other non-targeted cells, by virtue of its being cleared from the non-targeted cells through an antiviral response. This agent may be used to express a poxvirus or heterologous peptide or polypeptide in the targeted cells and/or to lethally infect such cells. It is particularly contemplated that the poxvirus is "attenuated" in respect to non-target cells or tissues, meaning the virus has a reduced, decreased, lessened, inhibited, or eliminated virulence, including its capability to modulate a host's endogenous anti-viral response. Thus, the present invention concerns compositions and methods involving vaccinia virus that has been altered to render it useful for treating cells or tissues that have a diminished capability to wage an antiviral response, yet be ineffective with respect to normal cells or tissues that can induce an efficient antiviral response. Methods of the invention specifically contemplate using such vaccinia viruses for treating cancer cells or tumors.

The mechanism by which viruses of the invention can be considered oncolytic and have enhanced safety and/or accelerated clearance from normal tissues involves the extent to which normal cells as opposed to non-normal cells (such as cancer cells or tissues) are capable of exhibiting an antiviral response (i.e., mounting, responding and/or inducing an immune response). Normal cells or tissues have such an ability, while cancer cells or tissues often do not express or have reduced levels of cellular proteins that induce or are involved in the anti-viral response. Such cellular proteins include interferons, TNF, chemokines, cytokines, and other factors. In normal cells or tissues, viruses that were attenuated and less able to counter an anti-viral immune response are readily cleared; however, in non-normal cells and/or tissues, the antiviral response is reduced and thus, even the attenuated virus is not as efficiently cleared. The basis for some embodiments of the invention is that the viruses discussed herein are an improved form of therapy, such as by enhanced safety and reduced toxicity on normal cells, as they will have less effect on normal, in contrast to non-normal, cells. Thus, the attenuated virus will preferentially replicate and express genes in cancer cells in which the induction or response to interferon, for example, is reduced or absent.

Compositions and methods of the invention concern poxviruses. Viruses discussed below may be included in compositions and methods of the invention. While many embodiments involve vaccinia virus, it is contemplated that other poxviruses may be generated or implemented in the same way, and thus, an embodiment concerning vaccinia virus can be applied with respect to any other poxvirus or other viruses with similar genes.

The present invention concerns altered vaccinia virus that comprises one or more mutations in its viral genome. The mutations may be introduced into the virus through recombinant engineering, by random mutagenesis, or by passaging the virus repeatedly. A virus whose viral genome has been manipulated using recombinant engineering (or the viral genome of any predecessor) is referred to as a "recombinant" virus. The mutation may be a deletion, insertion, or substitution of one or more nucleic acid residues. The mutation may be in a gene (which includes coding or noncoding sequences, such as transcriptional control sequences) or it may be elsewhere. The mutation in a coding region may lead to a cognate peptide or polypeptide that has a deletion, insertion, or substitution introduced into it. The nucleic acid mutation may also result in a frameshift mutation that gives rise to a truncated peptide or polypeptide or a peptide or polypeptide that has an altered amino acid sequence.

In some embodiments of the invention, the vaccinia virus is attenuated, which requires that the viral genome be altered to result in the viral attenuation. Mutations may affect different polypeptides that are classified according to function. Mutations may be in one or more of the following classes of polypeptides: 1) interferon-modulating polypeptide; 2) complement control polypeptide; 3) TNF or chemokine-modulating polypeptide; 4) serine protease inhibitor, 5) IL-1β modulating polypeptide; 6) non-infectious EEV form polypeptides; and, 7) viral polypeptide that act to inhibit release of infectious virus from cells (anti-infectious virus form polypeptide). In addition, there may be mutations in A41L or C11R of vaccinia virus (or the corresponding polypeptide in other poxviruses). Each class of polypeptides identifies polypeptides that have that particular function, either directly or indirectly. The classes are not mutually exclusive, as one polypeptide may possess more than one of the identified functions.

An interferon-modulating polypeptide refers to a poxvirus polypeptide that has an activity that affects a cell's interferon-induced or -activated pathway. Interferon is involved in the antiviral mechanism of some cells and organisms. Poxviruses express interferon-modulating polypeptides that attempt to inhibit this mechanism. It is specifically contemplated that these polypeptides may suppress, diminish, or eliminate this particular anti-viral reaction. These polypeptides modulate, affect, interfere with, inhibit, reduce, alter, or eliminate the activity or function of an interferon directly or indirectly. Interferon α, β, and γ are targets of interferon-modulating polypeptides. Interferon-modulating polypeptides may further be subdivided into polypeptides that specifically bind to an interferon; such polypeptides may be referred to as interferon-binding polypeptides. B18R is a soluble vaccinia virus polypeptide that is an interferon-binding polypeptide, as it specifically binds IFNα/β. B8R is another vaccinia virus polypeptide that specifically bind interferon-γ. Interferon modulating polypeptides include, but are not limited to, B18R—which may be termed B19R in other viral strains, such as the Copenhagen strain of Vaccinia virus—B8R, B13R, vC12L, A53R, and E3L of vaccinia virus, and other viral polypeptides with similar activities or properties. IFN modulating polypeptides may also be divided into the nonexclusive categories of those that preferentially modulate. IFNα and/or β pathways (including B18R, B8R, B13R, and vC12L of vaccinia virus) and those that modulate IFNγ pathways (including B8R, B13R, and vC12L of vaccinia virus). Any other polypeptide with an immunosuppressive function is also included.

A complement control polypeptide refers to a poxvirus polypeptide that plays a role in the prevention of complement-mediated cell killing and/or virus inactivation. A mechanism for the clearance of viral pathogens is the killing of infected cells or inactivation of virions within the host by complement-dependent mechanisms. It is specifically contemplated that these polypeptides may suppress, diminish, or eliminate this particular anti-viral reaction. These complement control polypeptides modulate, affect, interfere with, inhibit, reduce, alter, or eliminate the activity or function of this mechanism directly or indirectly. Complement control polypeptides include, but is not limited to, VCP of vaccinia virus, also known as C3L or C21L, and other polypeptides with this property or function (the terms "function" and activity" are used interchangeably).

A TNF-modulating polypeptide refers to a poxvirus polypeptide that has an activity that affects a cell's immune and inflammatory response that is activated via INF receptors. This response may involve inducing apoptotic cell death. Poxviruses express these TNF-modulating polypeptides as a way to counteract the TNF-mediated clearance of virus and/or virus-infected cells. These polypeptides have function in which they specifically bind and sequester extracellular TNF, resulting in the inhibition of viral clearance. It is specifically contemplated that these polypeptides may suppress, diminish, or eliminate this particular anti-vial reaction. These TNF-modulating polypeptides modulate, affect, interfere with, inhibit, reduce, alter, or eliminate the activity or function of this mechanism directly or indirectly. Thus, allowing the viral infection to proceed and viral virulence to be increased. TNF modulatory polypeptides include, but are not limited to, A53R and B28R of vaccinia virus, and other polypeptides with similar activities or properties.

A serine protease inhibitor (SPI) refers to a poxvirus polypeptide that is capable of inhibiting a serine protease. Such polypeptides are referred to as serpins. These polypeptides prevent apoptosis by apoptosis-inducing molecules through their SPI activity, and thus allow viral replication to proceed despite the presence of antiviral apoptosis-inducing cytokines, fas, granzyme or other stimulators of apoptosis. SPIs include, but are not limited to, B13R and B22R of vaccinia virus, and other polypeptides with similar activities or properties.

An IL-1β modulator refers to a poxvirus polypeptide that has an activity that affects the antiviral reactions elicited by IL-1 to be altered, directly or indirectly. IL-1 acts directly on B-cells, promoting their proliferation and the synthesis of immunoglobulins. IL-1 also functions as one of the priming factors that makes B-cells responsive to IL-5. IL-1 stimulates the proliferation and activation of NK-cells and fibroblasts, thymocytes, glioblastoma cells. An IL-18 modulator refers to a poxvirus polypeptide that has an activity that affects the antiviral reactions elicited by IL-18 to be altered, directly or indirectly. IL-18 acts by inducing IFNγ and/or inducing activation of cytotoxic T-cells and NK cells. These IL-1β or IL-18 modulator polypeptides modulate, affect, interfere with, inhibit, reduce, alter, or eliminate the activity or function of this mechanism directly or indirectly. It is specifically contemplated that these modulator polypeptides may suppress, diminish, or eliminate their particular anti-viral reaction. IL-1β modulating polypeptides include, but are not limited to, B13R and B15R of vaccinia virus, and other polypeptides with similar activities or properties. It is contemplated that other IL-1 modulators may be mutated as part of the invention. IL-18 modulating polypeptides include, but are not limited to vC12L and other polypeptides.

A viral polypeptide that acts to inhibit release of infectious virus from cells, anti-infectious EEV form polypeptide, refers to a viral polypeptide that has a function that directly contributes to the absence of vaccinia virus in an infectious EEV form. For example, the polypeptide that tethers or prevents the release of the EEV form from the cell membrane is an anti-infectious EEV form polypeptide. Polypeptides involved in the modulation of the EEV form of a virus include, but are not limited to, A34R and B5R of vaccinia virus, and various other proteins that influence the production of the EEV form of the poxviruses. A mutation at codon 151 of A34R from a lysine to a lutamic acid (K151E mutation) renders the A34R protein less able to tether the EEV form to the cell membrane.

Other mutations that may be included in poxviruses of the invention are mutations in the gene encoding C11R, a viral EGF-like protein, as well as A41L, B7R, N1L and/or vCKBP, which may have chemokine binding activity (U.S. Pat. No. 5,871,740 and Seet et al., 2001, each of which is incorporated herein by reference). For an exemplary description of vCKBP see U.S. Pat. No. 5,871,740 and Seet et al., 2001, each of which is incorporated herein by reference. Furthermore, it is contemplated that viruses of the invention may also have deletions in the viral genome to accommodate heterologous nucleic acid sequences. Such deletions may be non-essential regions, or they may be in essential regions that are complemented with either a helper virus or host cell.

In some embodiments, a poxvirus, particularly a vaccinia virus has at least one mutation in a first gene encoding an interferon-modulating polypeptide that results in the virus lacking at least a first interferon-modulating function. In further embodiments, the mutation is in a gene encoding an interferon-modulating polypeptide that directly binds interferon. It is contemplated that the interferon-binding polypeptide may be B8R and/or B18R.

Other more general classifications may also be applicable. Mutations may also be characterized in one or more of the following classes of polypeptides: 1) secreted viral factors that inhibit immune response components (e.g., TNF and other cytokines; chemokines, complement cascade; interferons α/β and γ; interleukins such as IL-1 and IL-18; A41L; N1L; vC12L; and C11R); 2) intracellular viral factors that act to block apoptosis (e.g., serine protease inhibitors) and/or immune activation (e.g., B13R, B22R, and B7R); and, 3) viral polypeptide(s) that act to inhibit release of infectious virus from cells. The classes are not mutually exclusive, as one polypeptide may possess more than one of the identified functions.

Throughout this application, the phrase "virus lacks functional X" refers to a virus that lacks at least one function of protein X. If protein X normally has two functions, then a virus lacking functional X refers to a virus that lacks at least one of these functions of polypeptide X. The lack of function may be achieved by a variety of mechanisms, including those in which the nucleic acid encoding polypeptide X, or the nucleic acid regions involved in its expression, is mutated compared to a virus having functional polypeptide X. Furthermore, a "virus lacking at least X function" refers to a virus that is missing or lacking the X function or activity of at least one polypeptide having X function. Furthermore, this phrase does not mean that the virus lacks any AND all X function, but that it has a mutation in its viral genome that renders a polypeptide having that X function either 1) no longer expressed or 2) no longer functional with respect to only function X (polypeptide may have other functions intact).

Vaccinia virus (or other poxviruses) of the invention may have alterations or mutations in one or more of the following seven classes 1) a gene encoding interferon-modulating polypeptide (including, but not limited to, B8R, B18R, B13R, E3L, and/or vC12L) that results in the virus lacking at least an interferon-modulating function; 2) a gene encoding a complement control polypeptide (including, but not limited to, VCP) that results in the virus lacking at least one complement control function; 3) a gene encoding a TNF-modulating polypeptide (including, but not limited to, A53R and B28R) that results in the virus lacking at least one TNF-modulating function; 4) a gene encoding a serine protease inhibitor (including, but not limited to, B13R, B22R, and/or K2L) that results in the virus lacking at least one serine protease inhibitor function; 5) a gene encoding an IL-1β modulator polypeptide (including, but not limited to, B15R) that results in the virus lacking at least one IL-1β modulator function; 6) a gene: encoding a polypeptide (including, but not limited to, B5R and/or A34R) that results in an increase in infectious EEV form of vaccinia virus; or 7) C11R, vCKBP, B7R, N1L and/or A41L.

Other vaccinia viruses of the invention may have a mutation that results in the virus lacking vC12L IL-18-modulating function. Additionally, such viruses may further comprises mutations in any of the seven classes discussed above.

It is contemplated that viruses of the invention may have a mutation in more than one gene from a single class of polypeptides. Thus, a viral genome may have mutations that render 1, 2, 3, 4, 5 or more polypeptides in the same class without the function that characterizes the class. It is further contemplated that viruses of the invention may have mutations in more than one class of polypeptides. Therefore, viral genomes may have mutations in genes encoding 1, 2, 3, 4, 5, 6, 7, or 8 of the 8 classes of polypeptides so as to render the virus lacking in the corresponding function of the encoded polypeptide. Moreover, viruses of the invention may have mutations in multiple genes from the same class of polypeptide and from different classes of polypeptides. The genes and their cognate polypeptides discussed in this application above are specifically contemplated as targets for mutation to render vaccinia viruses of the invention lacking in those particular polypeptides and respective functions. Also, any mutation discussed with respect to vaccinia virus may be implemented with respect to other poxviruses without undue experimentation.

The specific poxvirus polypeptides that may be mutated or rendered nonfunctional with respect to at least one function include, but are not limited to: A34R, A41L, A53R, B5R, B7R, B8R, B13R, B15R, B18R, B22R, B28R, B29R, C11R, E3L, K2L, N1L, vC12L, and vCKBP. Thus, poxviruses of the invention may have mutations in one or more of these genes encoding these corresponding vaccinia virus polypeptides.

In vaccinia viruses of the invention, a vaccinia virus may have a mutation that eliminates at least one function in A34R, in combination with mutation(s) that eliminate at least one function of 1, 2, 3, 4, 5, 6, 7, 8, 9, 10, 11, 12, 13, 14, 15, 16, or 17 of the following polypeptides: A41L, A53R, B5R, B7R, B8R, B13R, B15R, B18R, B22R, B28R, B29R, C11R, E3L, K2L, N1L, vC12L, and/or vCKBP.

In other vaccinia viruses of the invention, a vaccinia virus may have a mutation that eliminates at least one function in A41L in combination with mutation(s) that eliminate at least one function of 1, 2, 3, 4, 5, 6, 7, 8, 9, 10, 11, 12, 13, 14, 15, 16, or 17 of the following polypeptides: A34R, A53R, B5R, B7R, B8%, B13R, B1R, B18R, B22R, B28R, B29R, C11R, E3L, K2L, N1L, vC12L, and/or vCKBP. In other vaccinia viruses of the invention, a vaccinia virus may have a mutation that eliminates at least one function in A53R in combination with mutation(s) that eliminate at least one function of 1, 2, 3, 4, 5, 6, 7, 8, 9, 10, 11, 12, 13, 14, 15, 16, or 17 of the following polypeptides: A34R, A41L, B5R, B7R, B8R, B13R, B15R, B18R, B22R, B28R, B29R, C11R, E3L, K2L, N1L, vC12L, and/or vCKBP.

In other vaccinia viruses of the invention, a vaccinia virus may have a mutation that eliminates at least one function in B5R in combination with mutation(s) that eliminate at least one function of 1, 2, 3, 4, 5, 6, 7, 8, 9, 10, 11, 12, 13, 14; 15, 16, or 17 of the following polypeptides: A34R, A41L, A53R, B7R, B8R, B13R, B15R, B18R, B22R, B28R, B29R, C11R, E3L, K2L, N1L, vC12L, and/or vCKBP.

In other vaccinia viruses of the invention, a vaccinia virus may have a mutation that eliminates at least one function in B7R in combination with mutation(s) that eliminate at least one function of 1, 2, 3, 4, 5, 6, 7, 8, 9, 10, 11, 12, 13, 14, 15, 16, or 17 of the following polypeptides: A34R, A41L, A53R, B5R, B8R, B13R, B15R, B18R, B22R, B28R, B29R, C11R, E3L, K2L, N1L, vC12L, and/or vCKBP.

In other vaccinia viruses of the invention, a vaccinia virus may have a mutation that eliminates at least one function in B8R in combination with mutation(s) that eliminate at least one function of 1, 2, 3, 4, 5, 6, 7, 8, 9, 10, 11, 12, 13, 14, 15, 16, or 17 of the following polypeptides: A34R, A41L, A53R, B5R, B7R, B13R, B15R, B18R, B22R, B28R, B29R, C11R, E3L, K2L, N1L, vC12L, and/or vCKBP.

In other vaccinia viruses of the invention, a vaccinia virus may have a mutation that eliminates at least one function in B13R in combination with mutation(s) that eliminate at least one function of 1, 2, 3, 4, 5, 6, 7, 8, 9, 10, 11, 12, 13, 14, 15, or 16 of the following polypeptides: A34R, A41L, A53R, B5R, B7R, B8R, B15R, B18R, B22R, B28R, B29R, C11R, E3L, K2L, N1L, vC12L, and/or vCKBP.

In other vaccinia viruses of the invention, a vaccinia virus may have a mutation that eliminates at least one function in B15R in combination with mutation(s) that eliminate at least one function of 1, 2, 3, 4, 5, 6, 7, 8, 9, 10, 11, 12, 13, 14, 15, 16, or 17 of the following polypeptides: A34R, A41L, A53R, B5R, B7R, B8R, B13R, B18R, B22R, B28R, B29R, C11R, E3L, K2L, N1L, vC12L, and/or vCKBP.

In other vaccinia viruses of the invention, a vaccinia virus may have a mutation that eliminates at least one function in B18R in combination with mutation(s) that eliminate at least one function of 1, 2, 3, 4, 5, 6, 7, 8, 9, 10, 11, 12, 13, 14, 15, 16, or 17 of the following polypeptides: A34R, A41L, A53R, B5R, B7R, B8R, B13R, B15R, B22R, B28R, B29R, C11R, E3L, K2L, N1L, vC12L, and/or vCKBP.

In other vaccinia viruses of the invention, a vaccinia virus may have a mutation that eliminates at least one function in B22R in combination with mutation(s) that eliminate at least one function of 1, 2, 3, 4, 5, 6, 7, 8, 9, 10, 11, 12, 13, 14, 15, 16, or 17 of the following polypeptides: A34R, A41L, A53R, B5R, B7R, B8R, B13R, B15R, B18R, B28R, B29R, C11R, E3L, K2 N1L, vC12L, and/or vCKBP.

In other vaccinia viruses of the invention, a vaccinia virus may have a mutation that eliminates at least one function in B28R in combination with mutation(s) that eliminate at least one function of 1, 2, 3, 4, 5, 6, 7, 8, 9, 10, 11, 12, 13, 14, 15, 16, or 17 of the following polypeptides: A34R, A41L, A53R, B5R, B7R, B8R, B13R, B15R, B18R, B22R, B29R, C11R, E3L, K2 N1L, vC12L, and/or vCKBP.

In other vaccinia viruses of the invention, a vaccinia virus may have a mutation that eliminates at least one function in B29R (also known as C23L) in combination with mutation(s)

that eliminate at least one function of 1, 2, 3, 4, 5, 6, 7, 8, 9, 10, 11, 12, 13, 14, 15, 16, or 17 of the following polypeptides: A34R, A41L, A53R, B5R, B7R, B8R, B13R, B15R, B18R, B22R, B28R, C11R, E3L, K2L, N1L, vC12L, and/or vCKBP.

In other vaccinia viruses of the invention, a vaccinia virus may have a mutation that eliminates at least one function in C11R in combination with mutation(s) that eliminate at least one function of 1, 2, 3, 4, 5, 6, 7, 8, 9, 10, 11, 12, 13, 14, 15, 16, or 17 of the following polypeptides: A34R, A41L, A53R, B5R, B7R, B8R, B13R, B15R, B18R, B22R, B28R, B29R, E3L, K2L, N1L, vC12L, and/or vCKBP.

In other vaccinia viruses of the invention, a vaccinia virus may have a mutation that eliminates at least one function in E3L in combination with mutation(s) that eliminate at least one function of 1, 2, 3, 4, 5, 6, 7, 8, 9, 10, 11, 12, 13, 14, 15, 16, or 17 of the following polypeptides: A34R, A41L, A53R, B5R, B7R, B8R, B13R, B15R, B18R, B22R, B28R, B29R, C11R, K2L, N1L, vC12L, and/or vCKBP.

In other vaccinia viruses of the invention, a vaccinia virus may have a mutation that eliminates at least one function in K2L in combination with mutation(s) that eliminate at least one function of 1, 2, 3, 4, 5, 6, 7, 8, 9, 10, 11, 12, 13, 14, 15, 16, or 17 of the following polypeptides: A34R, A41L, A53R, B5R, B7R, B8R, B13R, B15R, B18R, B22R, B28R, B29R, C11R, E3L, N1L, vC12L, and/or vCKBP.

In other vaccinia viruses of the invention, a vaccinia virus may have a mutation that eliminates at least one function in N1L in combination with mutation(s) that eliminate at least one function of 1, 2, 3, 4, 5, 6, 7, 8, 9, 10, 11, 12, 13, 14, 15, 16, or 17 of the following polypeptides: A34R, A41L, A53R, B5R, B7R, B8R, B13R, B15R, B18R, B22R, B28R, B29R, C11R, E3L, K2L, vC12L, and/or vCKBP.

In other vaccinia viruses of the invention, a vaccinia virus may have a mutation that eliminates at least one function in vC12L in combination with mutation(s) that eliminate at least one function of 1, 2, 3, 4, 5, 6, 7, 8, 9, 10, 11, 12, 13, 14, 15, 16, or 17 of the following polypeptides: A34R, A41L, A53R, B5R, B7R, B8R, B13R, B15R, B18R, B22R, B28R, B29R, C11R, E3L, K2L, N1L, and/or vCKBP.

In other vaccinia viruses of the invention, a vaccinia virus may have a mutation that eliminates at least one function in vCKBP in combination with mutation(s) that eliminate at least one function of 1, 2, 3, 4, 5, 6, 7, 8, 9, 10, 11, 12, 13, 14, 15, 16, or 17 of the following polypeptides: A34R, A41L, A53R, B5R, B7R, B8R, B13R, B15R, B18R, B22R, B28R, B29R, C11R, E3L, K2L, N1L, and/or vC12L.

In some embodiments of the invention, the Copenhagen or Western Reserve strain is mutated to generate vaccinia viruses of the invention. These strains may be further mutated in one or more of the seven classes of polypeptides discussed above.

Vaccinia viruses of the invention may comprise a virus that lacks B8R, B18R, B13R, or vC12L interferon-modulating function; a virus that lacks B8R interferon-modulating function, a virus that lacks B13R interferon-modulating function; a virus that lacks B8R and, B13R interferon-modulating functions; a virus that lacks B8R, B13R, and vC12L interferon-modulating functions, and that may further lack B28R or A53R, or both interferon-modulating function(s); a virus that lacks B8R, B13R, and vC12L interferon-modulating functions, and that may further lack B18R interferon-modulating function; a virus that lacks B8R, B13R, B18R, and vC12L interferon-modulating functions, and that may further lack B28R and/or A53R interferon-modulating function(s); a virus that lacks at least one interferon-modulating function and VCP complement control function; a virus that lacks at least one interferon-modulating function and A53R, B28R, and/or vCKBP TNF-modulating function(s); a virus that lacks at least one interferon-modulating function and B13R, B22R, and/or K2L serine protease function(s); a virus that lacks at least one interferon-modulating function and B13R and/or B15R IL-1β modulating function (s); a virus that lacks at least one interferon-modulating function and comprising a mutation in A34R or B5R that results in an increase in production of infectious EEV form of vaccinia virus; a virus that lacks the function of C11R, vCKBP, B7R, N1L and/or A41L; or a virus lacking any combination of functions discussed above.

Other vaccinia viruses have a mutation resulting in a virus that lacks vC12L interferon-modulating function. Such viruses may further include mutations in one or more of the seven classes discussed above. In some embodiments, the virus lacks B8R, B13R, and/or B18R functions(s), while in others it also lacks B15R IL-1β modulating function, and/or any other function discussed above, such as vCKBP and/or B13R function and/or B29R TNF-modulating function.

In some embodiments of the invention, poxviruses are used for administration to a subject, in which case the virus is comprised in a pharmaceutical composition. Compositions of the invention may also include interferon (α, β, and/or γ) and/or an anti-cancer agent, such as an antibody, a chemotherapeutic, or a nucleic acid encoding a therapeutic cancer polypeptide.

Methods of the invention involve using any of the poxviruses discussed herein. Many embodiments concern treating a cancer cell or treating a patient with cancer by administering to the cancer cell or patient an effective amount of a vaccinia virus. In some embodiments, the vaccinia virus is unable to express at least one of the following:

a) a functional first interferon-modulating polypeptide;
    b) a functional complement control polypeptide;
    c) a functional TNF-modulating polypeptide;
    d) a functional serine protease inhibitor,
    e) a functional IL-1β modulating polypeptide;
    f) a functional non-infectious EEV form polypeptide;
    g) a functional A41L, B7R, N1L or vCKBP chemokine binding polypeptide or C11R EGF-like polypeptide.

It is specifically contemplated that the virus lacks more than one of a)-g) functional polypeptides A "functional polypeptide" refers to a polypeptide that contains the identified function; for example, a virus that lacks a functional interferon-modulating polypeptide refers to a virus whose genome is mutated, and consequently, the virus is lacking an interferon-modulating function (as opposed to lacking all interferon-modulating functions of all interferon modulating polypeptides). The virus may have a mutation that allows a mutated polypeptide to be expressed, but the resultant polypeptide may be mutated so that it no longer possesses the identified function.

In some methods of the invention, the cancer cell is a tumor cell. Furthermore, the cell may be administered compositions of the invention in vitro, in vivo, or ex vivo. Thus, the cancer cell may be in a patient. The patient may have a solid tumor. In such cases, embodiments may further involve performing surgery on the patient, such as by resecting all or part of the tumor. Viral compositions may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intrarterially, intravesically, or subcutaneously. Viral compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. In addition, a cell or patient may be administered a protease or peptidase to increase the production of infectious EEV form of the virus from cells. The peptidase or protease may be included in pharmaceutical compositions that also include virus. Moreover, a cell or a patient may be administered a microtubule stabilizing agent, including, but not limited to, taxane, as part of methods of the invention. It is specifically contemplated that any of the poxviruses or modified poxviruses discussed herein, including the Western Reserve and Copenhagen vaccinia virus strains (as well as derivatives thereof), can be used with these combination therapies. For example, the Copenhagen vaccinia virus strain can be employed in conjunction with taxol to achieve a therapeutic effect on a cancer cell or in a cancer patient.

In some embodiments, the cancer cell that is administered viral compositions may be a bladder, blood, bone, bone marrow, brain, breast, colorectal, esophagus, gastrointestine, head, kidney, liver, lung, nasopharynx, neck, ovary, pancreas, prostate, skin, stomach, testicular, tongue, or uterus cell.

In other embodiments of the invention, attenuated vaccinia virus further includes a nucleic acid sequence encoding a heterologous therapeutic polypeptide. The heterologous therapeutic polypeptide is a tumor suppressor, immunomodulator, angiogenesis inhibitor, anti-vascular polypeptide, cytotoxic polypeptide, apoptosis inducer, pro-drug activating enzyme, or cytostatic polypeptide in different embodiments of the invention.

Methods of the invention may involve employing an attenuated vaccinia virus that is the IHD-J strain or comprises a K151E mutation in A34R. Alternatively, to generate vaccinia viruses that are more resistant to destruction by complement or the complement pathway, virus may be produced from a cell line that overexpresses at least one human complement inhibitory protein. The complement inhibitory protein can be CD55, CD46, or CD59.

In specific embodiments, there are methods for treating cancer in a patient involving administering to the patient an effective amount of a pharmaceutically acceptable composition comprising a recombinant vaccinia virus comprising a mutation in the gene encoding B8R, B18R, or vC12L, resulting in a virus that lacks B8R, B18R, or vC12L interferon modulating function. An "effective amount" of the pharmaceutical composition, generally, is defined as that amount sufficient to detectably and repeatedly ameliorate, reduce, minimize or limit the extent of the disease or its symptoms, such as cancer. It is contemplated that a composition comprising $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, $10^{25}$, or more viral particles or pfus may be administered 1, 2, 3, 4, 5, 6, 7, 8, 9, 10 or more times to a patient.

It is further contemplated that the attenuated vaccinia virus will lack B8R, B18R or vC12L interferon-modulating function and further possess a mutation in a gene encoding B13R, which results in the virus lacking B13R interferon-modulating function. In still further embodiments, the attenuated vaccinia virus lacks B8R, vC12L, and B13R interferon-modulating functions, while in others it lacks at least two of B8R, B18R, or vC12L interferon modulating functions. It is specifically contemplated that the attenuated vaccinia virus lacks B8R, B18R, and vC12L interferon-modulating functions. In addition, a recombinant vaccinia virus that lacks B8R, B18R, or vC12L interferon modulating function may further lacks at least one of the following:

a) a complement control polypeptide function;
b) a TNF-modulating function
c) a serine protease inhibitor function;
d) an IL-1β modulator function;
e) an anti-infectious EEV form function; or
f) A41L, B7R, N1L, and/or vCKBP chemokine modulating function or C11R EGF-like function.

Other embodiments of the invention include methods for killing a cancer cell by contacting the cancer cell with an attenuated vaccinia virus comprising a mutation that reduces the virus' ability to inhibit an antiviral response mediated by an interferon, a chemokine, a cytokine, complement, or neutralizing antibody. Some embodiments involve an attenuated vaccinia virus that has a mutation in a nucleic acid sequence encoding B8R, B13R, B18R, or vC12L. It is further contemplated that these viruses may lack one or more of a)-f) discussed in the preceding paragraph.

In still further embodiments of the invention, there are methods of treating cancer in a cancer patient involving contacting a tumor site with a therapeutically effective amount of a composition comprising an attenuated vaccinia virus and an agent that increases antitumoral efficacy of the attenuated vaccinia virus, so as to effect treatment of the cancer. The agent that increases the antitumoral efficacy of the attenuated vaccinia virus can be an interferon, proteinase, peptidase, microtubule stabilizing agent, chemotherapy, radiotherapy, gene therapy, immunotherapy, or immunomodulatory therapy.

In addition to therapeutic methods, the present invention concerns methods for producing a fortified EEV form of vaccinia virus comprising: a) infecting a human cell line that overexpresses a complement inhibitory protein with a vaccinia virus; and, b) isolating the EEV form of the vaccinia virus from the infected cell. A "fortified EEV form of vaccinia virus" refers to an EEV form of vaccinia virus that is stronger or more resistant to viral degradation mechanisms of an organism than an EEV form produced from a wild-type vaccinia virus.

In some methods, the vaccinia virus comprises a mutation in the gene encoding A34R protein. In some cases, the mutation results in a K151E mutation. Other embodiments involve complement inhibitory protein that is CD55, CD46, or CD59. In still further embodiments, the human cell line overexpresses more than one complement inhibitory protein.

In addition to methods, compositions that result from methods for producing fortified EEV form of vaccinia virus are included as part of the invention. A composition comprising vaccinia virus in which the composition is at least 10%, 15%, 20%, 25%, 30%, 40%, 50%, 60%, 70%, 80%, 90%, or is 100% fortified EEV form of vaccinia virus are specifically included.

Similarly, the present invention concerns human cell lines for the production of fortified EEV form of vaccinia virus. Such cell lines are injectable with vaccinia virus, have vaccinia virus, or vaccinia virus expression constructs, and they overexpress at least one complement inhibitory polypeptide. The complement inhibitory polypeptide may be CD55, CD46, or CD59. The host cell may be infected with a vaccinia virus that lacks at least one of the following:
- a) an interferon-modulating function;
- b) a complement control polypeptide function;
- c) a TNF-modulating function
- d) a serine protease inhibitor function;
- e) an IL-1β modulator function;
- f) a functional anti-infectious EEV form polypeptide; or
- g) a functional A41L, B7R, N1L or vCKBP chemokine binding polypeptide or C11R EGF-like polypeptide.

Other methods of the invention include methods for treating microscopic residual cancer comprising: i) identifying a patient having a resectable tumor, (ii) resecting the tumor, and (iii) contacting the tumor bed with a vaccinia virus having at least one mutation in a gene encoding A34R, A41L, A53R, B5R, B7R, B8R, B13R, B15R, B18R, B22R, B28R, B29R, C11R, E3L, K2L, N1L, vC12L, or vCKBP.

Other methods include treating a subject having a tumor comprising: (i) surgically revealing the tumor; and (ii) contacting said tumor with an attenuated vaccinia virus lacking A34R, A41L, A53R, B5R, B7R, B8R, B13R, B15R, B18R, B22R, B28R, B29R, C11R, E3L, K2L, N1L, vC12L, or vCKBP function.

In additional embodiments, methods for treating a subject having a tumor include perfusing the tumor, over an extended period of time, with an attenuated vaccinia virus. While in other embodiments, there are methods of inhibiting metastatic disease in a subject having cancer comprising administering to the subject an attenuated vaccinia virus, thereby conferring a therapeutic benefit on the subject. The term "therapeutic benefit" used throughout this application refers to anything that promotes or enhances the well-being of the subject with respect to the medical treatment of his condition, which includes treatment of pre-cancer and cancer. A list of nonexhaustive examples of this includes extension of the subject's life by any period of time, decrease or delay in the neoplastic development of the disease, decrease in hyperproliferation, reduction in tumor growth, delay of metastases, reduction in cancer cell or tumor cell proliferation rate, and a decrease in pain to the subject that can be attributed to the subject's condition.

In further aspects of the invention, there are methods of treating a multidrug-resistant tumor in a patient comprising i) administering to the patient an attenuated vaccinia virus and ii) administering chemotherapy or radiotherapy to the patient, thereby conferring a therapeutic benefit on the subject. Furthermore, there are methods of rendering an unresectable tumor in a patient resectable comprising administering to the patient an effective amount of an attenuated vaccinia virus and resecting all or part of the tumor. Alternatively, the invention covers treating a cancer patient whose cancer is resistant to chemotherapy or radiotherapy comprising administering to the patient an attenuated vaccinia virus and administering chemotherapy or radiotherapy to the patient.

It is specifically contemplated that any embodiment discussed with respect to a particular method or composition may be implemented with respect to other methods and compositions of the invention.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
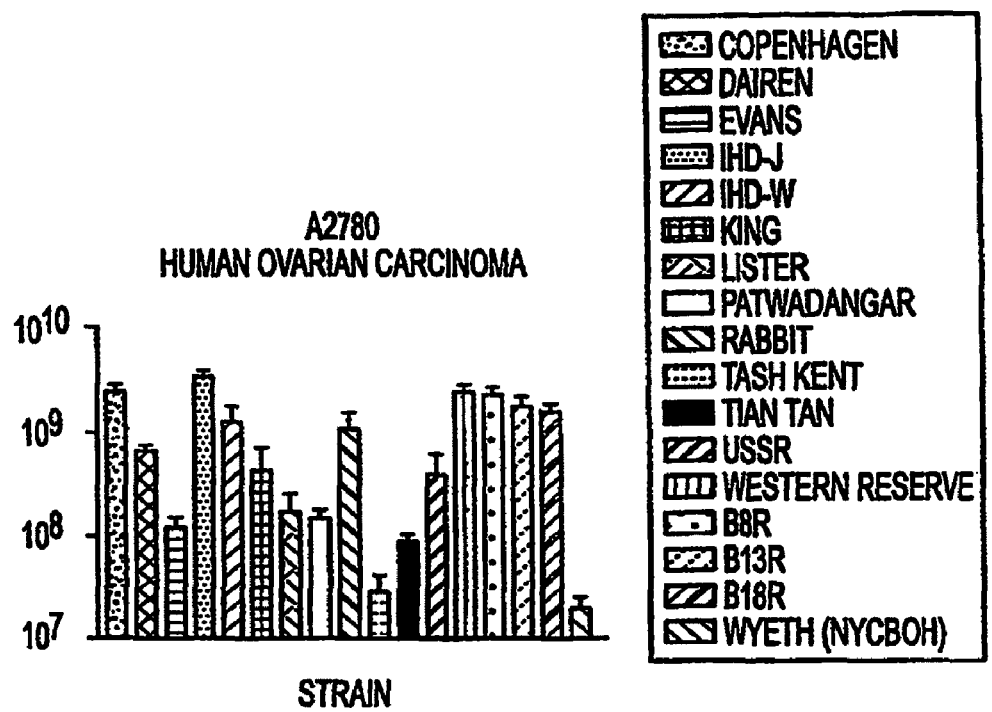
FIGS. 1A and 1B illustrates an example of Vaccinia virus strain replication in (FIG. 1A) A2780 human ovarian carcinoma cell line and (FIG. 1B) HCT116 human colon carcinoma cell line. (x-axis is the strain and the y-axis is plaque forming units per ml +/−S.E.)
Figure 1B:
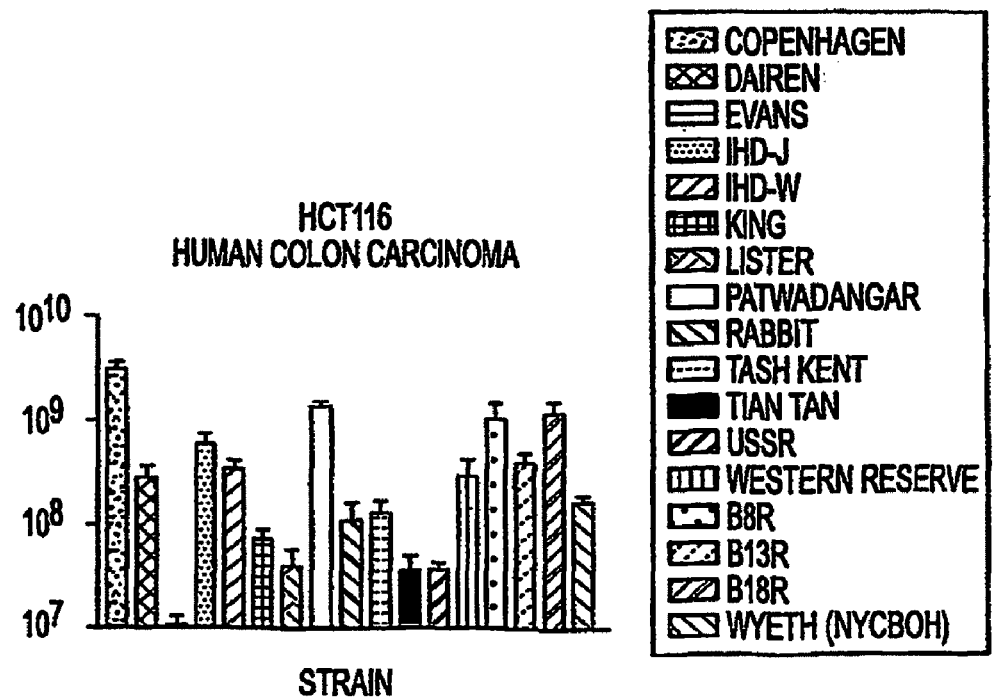

The present invention concerns oncolytic poxviruses for the treatment of cancer. Poxviruses can be engineered to be more effective or more efficient at killing cancer cells and/or be less toxic or damaging to non-cancer cells. More specifically, poxviruses may be mutated to modify gene products such that the modifications render the viruses better able to infect the host, better able to infect cancer cells.

I. Poxviruses

Viruses are frequently inactivated, inhibited or cleared by immunomodulatory molecules such as interferons (-α, -γ, -γ) and tumor necrosis factor-α (TNF) (Moss, 1996). Host tissues and inflammatory/immune cells frequently secrete these molecules in response to viral infection. These molecules can have direct antiviral effects and/or indirect effects through recruitment and/or activation of inflammatory cells and lymphocytes. Given the importance of these immunologic clearance mechanisms, viruses have evolved to express gene products that inhibit the induction and/or function of these cytokines/chemokines and interferons. For example, vaccinia virus (VV; and some other poxviruses) encodes the secreted protein vCKBP (B29R) that binds and inhibits the CC chemokines (e.g., RANTES, eotaxin, MIP-1-alpha) (Alcami et al., 1998). Some VV strains also express a secreted viral protein that binds and inactivates TNF (e.g., Lister A53R) (Alcami et al., 1999). Most poxvirus strains have genes encoding secreted proteins that bind and inhibit the function of interferons-α/β (e.g., B18R) or interferon-γ (B8R). vC12L is an IL-18-binding protein that prevents IL-18 from inducing IFN-γ and NK cell/cytotoxic T-cell activation.

Most poxvirus virulence research has been performed in mice. Many, but not all, of these proteins are active in mice (B18R, for example, is not). In situations in which these proteins are active against the mouse versions of the target cytokine, deletion of these genes leads to reduced virulence and increased safety with VV mutants with deletions of or functional mutations in these genes. In addition, the inflammatory/immune response to and viral clearance of these mutants is often increased compared to the parental virus strain that expresses the inhibitory protein. For example, deletion of the T1/35 kDa family of poxvirus-secreted proteins (chemokine-binding/-inhibitory proteins) can lead to a marked increase in leukocyte infiltration into virus-infected tissues (Graham et al., 1997). Deletion of the vC12L gene in VV leads to reduced viral titers/toxicity following intranasal administration in mice; in addition, NK cell and cytotoxic T-lymphocyte activity is increased together with IFN-γ induction (Smith et al., 2000). Deletion of the Myxoma virus T7 gene (able to bind IFN-γ and a broad range of chemokines) results in reduced virulence and significantly increased tissue inflammation/infiltration in a toxicity model (Upton et al., 1992; Mossman et al., 1996). Deletion of the M-T2 gene from myxoma virus also resulted in reduced virulence in a rabbit model (Upton et al. 1991). Deletion of the B18R anti-interferon-α/-β gene product also leads to enhanced viral sensitivity to IFN-mediated clearance, reduced titers in normal tissues and reduced virulence (Symons et al., 1995; Colamonici et al., 1995; Alcami et al., 2000). In summary, these viral gene products function to decrease the antiviral immune response and inflammatory cell infiltration into virus-infected tissues. Loss of protein function through deletion/mutation leads to decreased virulence and/or increased proinflammatory properties of the virus within host tissues.

Cytokines and chemokines can have potent antitumoral effects (Vicari et al., 2002; Homey et al., 2002). These effects can be on tumor cells themselves directly (e.g., TNF) or they can be indirect through effects on non-cancerous cells. An example of the latter is TNF, which can have antitumoral effects by causing toxicity to tumor-associated blood vessels; this leads to a loss of blood flow to the tumor followed by tumor necrosis. In addition, chemokines can act to recruit (and in some cases activate) immune effector cells such as neutrophils, eosinophils, macrophages and/or lymphocytes. These immune effector cells can cause tumor destruction by a number of mechanisms. These mechanisms include the expression of antitumoral cytokines (e.g., TNF), expression of fas-ligand, expression of perforin and granzyme, recruitment of natural killer cells, etc. The inflammatory response can eventually lead to the induction of systemic tumor-specific immunity. Finally, many of these cytokines (e.g., TNF) or chemokines can act synergistically with chemotherapy or radiation therapy to destroy tumors.

Clinically effective systemic administration of recombinant versions of these immunostimulatory proteins is not feasible due to 1) induction of severe toxicity with systemic administration and 2) local expression within tumor tissue is needed to stimulate local infiltration and antitumoral effects. Approaches are needed to achieve high local concentrations of these molecules within tumor masses while minimizing levels in the systemic circulation. Viruses can be engineered to express cytokine or chemokine genes in an attempt to enhance their efficacy. Expression of these genes from replication-selective vectors has potential advantages over expression from non-replicating vectors. Expression from replicating viruses can result in higher local concentrations within tumor masses; in addition, replicating viruses can help to induce antitumoral immunity through tumor cell destruction/oncolysis and release of tumor antigens in a proinflammatory environment. However, there are several limitations to this approach Serious safety concerns arise from the potential for release into the environment of a replication-competent virus (albeit tumor-selective) with a gene that can be toxic if expressed in high local concentrations. Viruses that express potent pro-inflammatory genes from their genome may therefore pose safety risks to the treated patient and to the general public. Even with tumor-targeting, replication-selective viruses expressing these genes, gene expression can occur in normal tissues resulting in toxicity. In addition, size limitations prevent expression of multiple and/or large genes from viruses such as adenovirus; these molecules will definitely act more efficaciously in combination. Finally, many of the oncolytic viruses in use express anti-inflammatory proteins and therefore these viruses will counteract the induction of a proinflammatory milieu within the infected tumor mass. The result will be to inhibit induction of antitumoral immunity, antivascular effects and chemotherapy-/radiotherapy-sensitization.

A. Vaccinia Virus

1. Interferon-Modulating Polypeptides

Interferon-α/-β blocks viral replication through several mechanisms. Interferon-γ has weaker direct viral inhibitory effects but is a potent inducer of cell-mediated immunity through several mechanisms. Viruses have evolved to express secreted gene products that are able to counteract the antiviral effects of interferons. For example, vaccinia virus (and other poxviruses) encodes the secreted proteins B8R and B18R which bind interferon-γ and -α/-β, respectively (Smith et al., 1997; Symons et al., 1995; Alcami et al., 2000). An additional example of a vaccinia gene product that reduces interferon induction is the caspase-1 inhibitor B13R which inhibits activation of the interferon-γ-inducing factor IL-18. Interferon modulating polypeptides include, but are not limited to, B18R, which may be termed B19R in other viral strains, such as the Copenhagen strain of Vaccinia virus; B8R; B13R; vC12L; A53R; E3L and other viral polypeptides with similar activities or properties. IFN modulating polypeptides may be divided into the non-exclusive categories of those that preferentially modulate IFNα and/or β pathways (such as B18R, B8R, B13R, or vC12L) and those that modulate IFNγ pathways (for example B8R, B13R, or vC12L).

Cancer cells are frequently resistant to the effects of interferons. A number of mechanisms are involved. These include the fact that ras signal transduction pathway activation (e.g., by ras mutation, upstream growth factor receptor overexpression/mutation, etc.), a common feature of cancer cells, leads to PKR inhibition. In addition, lymphocytes are often inhibited in tumor masses by a variety of mechanisms including IL-10 production and fas-L expression by tumor cells. Since lymphocytes are a major source of interferon-γ production, lymphocyte inhibition leads to a decrease in interferon-γ production in tumors. Therefore, tumor masses tend to be sanctuaries from: the effects of interferons. In addition, interferons themselves can have antitumoral effects. For example, IFN-γ can increase MHC class-I-associated antigen presentation; this will allow more efficient CTL-mediated killing of tumor cells IFN-α/β, for example, can block angiogenesis within tumor masses and thereby block tumor growth.

2. Complement Control Polypeptides

A major mechanism for the clearance of viral pathogens is the killing of infected cells within the host or of virions within an organism by complement-dependent mechanisms. As the infected cell dies it is unable to continue to produce infectious virus. In addition, during apoptosis intracellular enzymes are released which degrade DNA. These enzymes can lead to viral DNA degradation and virus inactivation. Apoptosis can be induced by numerous mechanisms including the binding of activated complement and the complement membrane attack complex. Poxviruses such as vaccinia have evolved to express gene products that are able to counteract the complement-mediated clearance of virus and/or virus-infected cells. These genes thereby prevent apoptosis and inhibit viral clearance by complement-dependent mechanisms, thus allowing the viral infection to proceed and viral virulence to be increased. For example, vaccinia virus complement control proteins (VCP; e.g., C21L) have roles in the prevention of complement-mediated cell killing and/or virus inactivation (Isaacs et al., 1992). VCP also has anti-inflammatory effects since its expression decreases leukocyte infiltration into virally-infected tissues. Complement control polypeptides include, but are not limited to, VCP, also known as C3L or C21L.

Cancer cells frequently overexpress cellular anti-complement proteins; this allows cancer cells to survive complement attack +/−tumor-specific antibodies (Caragine et al., 2002; Durrant et al., 2001; Andoh et al. 2002). Therefore, agents that preferentially target tumor cells due to their inherent resistance to complement-mediated killing would have selectivity and potential efficacy in a wide range of human cancers (Durrant et al., 2001). In addition, one of the hallmarks of cancer cells is a loss of normal apoptotic mechanisms (Gross et al., 1999). Resistance to apoptosis promotes carcinogenesis as well as resistance to antitumoral agents including immunologic, chemotherapeutic and radiotherapeutic agents (Eliopoulos et al., 1995). Apoptosis inhibition can be mediated by a loss of pro-apoptotic molecule function (e.g., bax), an increase in the levels/function of anti-apoptotic molecules (e.g., bcl-2) and finally a loss of complement sensitivity.

3. TNF-Modulating Polypeptides

One of the various mechanisms for the clearance of viral pathogens is the killing of infected cells within the host by the induction of apoptosis, as described above. Apoptosis can be induced by numerous mechanisms including the binding of TNF and lymphotoxin-alpha (LTα) to cellular TNF receptors, which triggers intracellular signaling cascades. Activation of the TNF receptors function in the regulation of immune and inflammatory responses, as well as inducing apoptotic cell death (Wallach et al., 1999)

Various strains of poxviruses, including some vaccinia virus strains, have evolved to express gene products that are able to counteract the TNF-mediated clearance of virus and/or virus-infected cells. The proteins encoded by these genes circumvent the proinflammatory and apoptosis inducing activities of TNF by binding and sequestering extracellular TNF, resulting in the inhibition of viral clearance. Because viruses are not cleared, the viral infection is allowed to proceed, and thus, viral virulence is increased. Various members of the poxvirus family express secreted viral TNF receptors (vTNFR). For example, several poxviruses encode vTNFRs, such as myxoma (T2 protein), cowpox and vaccinia virus strains, such as Lister, may encode one or more of the CrmB, CrmC (A53R), CrmD, CrmE, B28R proteins and/or equivalents thereof These vTNFRs have, roles in the prevention of TNF-mediated cell killing and/or virus inactivation (Saraiva and Alcami, 2001). TNF modulatory polypeptides include, but are not limited to, A53R, B28R (this protein is present, but may be inactive in the Copenhagen strain of vaccinia virus) and other polypeptides with similar activities or properties.

One of the hallmarks of cancer cells is aberrant gene expression, which may lead to a loss of sensitivity to a number of molecular mechanisms for growth modulation, such as sensitivity to the anti-cancer activities of TNF. Thus, viral immunomodulatory mechanisms may not be required for the propagation of a virus within the tumor microenvironment.

4. Serine Protease Inhibitors

A major mechanism for the clearance of viral pathogens is the induction of apoptosis in infected cells within the host. As the infected cell dies it is unable to continue to produce infectious virus. In addition, during apoptosis intracellular enzymes are released which degrade DNA. These enzymes can lead to viral DNA degradation and virus inactivation. Apoptosis can be induced by numerous mechanisms including the binding of cytokines (e.g., tumor necrosis factor), granzyme production by cytotoxic T-lymphocytes or fas-ligand binding; caspase activation is a critical part of the final common apoptosis pathway. Viruses have evolved to express gene products that are able to counteract the intracellular signalling cascade induced by such molecules including fas-ligand or tumor necrosis factor (TNF)/TNF-related molecules (e.g. E3 10.4/14.5, 14.7 genes of adenovirus (Wold et al., 1994); E1B-19 kD of adenovirus (Boyd et al., 1994); crmA from cowpoxvirus; B13R from vaccinia virus) (Dobbelstein et al., 1996; Kettle et. al., 1997). These gene products prevent apoptosis by apoptosis-inducing molecules and thus allow viral replication to proceed despite the presence of antiviral apoptosis-inducing cytokines, fas, granzyme or other stimulators of apoptosis.

VV SPI-2/B13R is highly homologous to cowpox CrmA; SPI-1 (VV) is weakly homologous to CrmA (Dobbelstein et al., 1996). These proteins are serpins (serine protease inhibitors) and both CrmA and SPI-2 have roles in the prevention of various forms of apoptosis. Inhibition of interleukin-1β-converting enzyme (ICE) and granzyme, for example, can prevent apoptosis of the infected cell. These gene products also have anti-inflammatory effects. They are able to inhibit the activation of IL-18 which in turn would decrease IL-18-mediated induction of IFN-γ. The immunostimulatory effects of IFN-γ on cell-mediated immunity are thereby inhibited (Kettle et al., 1997). SPIs include, but are not limited to, B13R, B22R, and other polypeptides with similar activities or properties.

One of the hallmarks of cancer cells is a loss of normal apoptotic mechanisms (Gross et al., 1999). Resistance to apoptosis promotes carcinogenesis as well as resistance to antitumoral agents including immunologic, chemotherapeutic and radiotherapeutic agents (Eliopoulos et al., 1995). Apoptosis inhibition can be mediated by a loss of pro-apoptotic molecule function (e.g., bax) or an increase in the levels/function of anti-apoptotic molecules (e.g., bcl-2).

5. IL-1β-Modulating Polypeptides

IL-1β is a biologically active factors that acts locally and also systemically. Only a few functional differences between IL-1β and IL-1α have been described. The numerous biological activities of IL-1β is exemplified by the many different acronyms under which IL-1 has been described. IL-1 does not show species specificity with the exception of human IL-1β that is inactive in porcine cells. Some of the biological activities of IL-1 are mediated indirectly by the induction of the synthesis of other mediators including ACTH (Corticotropin), PGE2 (prostaglandin E2), PF4 (platelet factor-4), CSF (colony stimulating factors), IL-6, and IL-8. The synthesis of IL-1 may be induced by other cytokines including TNF-α, IFN-α, IFN-β and IFN-γ and also by bacterial endotoxins, viruses, mitogens, and antigens. The main biological activity of IL-1 is the stimulation of T-helper cells, which are induced to secrete IL-2 and to express IL-2 receptors. Virus-infected macrophages produce large amounts of an IL-1 inhibitor that may support opportunistic infections and transformation of cells in patients with T-cell maturation defects. IL-1 acts directly on B-cells, promoting their proliferation and the synthesis of immunoglobulins. IL-1 also functions as one of the priming factors that makes B-cells responsive to IL-5. IL-1 stimulates the proliferation and activation of NK-cells and fibroblasts, thymocytes, glioblastoma cells.

Blockade of the synthesis of IL-1β by the viral protein is regarded as a viral strategy allowing systemic antiviral reactions elicited by IL-1 to be suppressed or diminished. Binding proteins effectively blocking the functions of IL-1 with similar activity as B15R have been found also to be encoded by genes of the cowpox virus. Vaccinia virus also encodes another protein, designated B8R, which behaves like a receptor for cytokines (Alcami and Smith, 1992; Spriggs et al., 1992). IL-1 modulating polypeptides include, but are not limited to, B13R, B15R, and other polypeptides with similar activities or properties.

One of the hallmarks of cancer cells is aberrant gene expression, which may lead to a loss of sensitivity to a number of molecular mechanisms for growth modulation, such as sensitivity to the anti-cancer activities of IL-1. Thus, viral immunomodulatory mechanisms may not be required for the propagation of a virus within the tumor microenvironment.

6. EEV Form

Viral spread to metastatic tumor sites, and even spread within an infected solid tumor mass, is generally inefficient (Heise et al., 1999). Intravenous administration typically results in viral clearance or inactivation by antibodies (e.g., adenovirus) (Kay et al., 1997) and/or the complement system (e.g., HSV) (Ikeda et al., 1999). In addition to these immune-mediated mechanisms, the biodistribution of these viruses results in the vast majority of intravenous virus depositing within normal tissues rather than in tumor masses. Intravenous adenovirus, for example, primarily ends up within the liver and spleen; less than 0.1% of the input virus depositing within tumors, even in immunodeficient mice (Heise et al., 1999). Therefore, although some modest antitumoral efficacy can be demonstrated with extremely high relative doses in immunodeficient mouse tumor models, intravenous delivery is extremely inefficient and significantly limits efficacy.

Vaccinia virus has the ability to replicate within solid tumors and cause necrosis. In addition, thymidine kinase-deletion mutants can infect tumor masses and ovarian tissue and express marker genes preferentially in mouse tumor model systems (Gnant et al., 1999). However, since these studies generally determined tumor targeting based on marker gene expression after ≧5 days, it is unclear whether the virus preferentially deposits in, expresses genes in or replicates in tumor/ovary tissue (Puhlmann et al., 2000). Regardless of the mechanism, the antitumoral efficacy of this virus without additional transgenes was not statistically significant (Gnant et al., 1999). In contrast intratumoral virus injection had significant antitumoral efficacy (McCart et al. 2000). Therefore, i.v. efficacy could be improved if i.v. delivery to the tumor were to be improved.

Vaccinia virus replicates in cells and produces both intracellular virus (IMV, intracellular mature virus; IEV, intracellular enveloped virus) and extracellular virus (EEV, extracellular enveloped virus; CEV, cell-associated extracellular virus) (Smith et al., 1998). IMV represents approximately 99% of virus yield following replication by wild-type vaccinia virus strains. This virus form is relatively stable in the environment, and therefore it is primarily responsible for spread between individuals; in contrast, this virus does not spread efficiently within the infected host due to inefficient release from cells and sensitivity to complement and/or antibody neutralization. In contrast, EEV is released into the extracellular milieu and typically represents only approximately 1% of the viral yield (Smith et al., 1998). EEV is responsible for viral spread within the infected host and is relatively easily degraded outside of the host. Importantly, EEV has developed several mechanisms to inhibit its neutralization within the bloodstream. First, EEV is relatively resistant to complement (Vanderplasschen et al., 1998); this feature is due to the incorporation of host cell inhibitors of complement into its outer membrane coat plus secretion of Vaccinia virus complement control protein (VCP) into local extracellular environment. Second, EEV is relatively resistant to neutralizing antibody effects compared to MV (Smith et al., 1997). EEV is also released at earlier time points following infection (e.g., 4-6 hours) than is IMV (which is only released during/after cell death), and therefore spread of the EEV form is faster (Blasco et al., 1993).

Unfortunately, however, wild-type vaccinia stains make only very small amounts of EEV, relatively. In addition, treatment with vaccinia virus (i.e., the input dose of virus) has been limited to intracellular virus forms to date. Standard vaccinia virus (VV) manufacturing and purification procedures lead to EEV inactivation (Smith et al., 1998), and non-human cell lines are frequently used to manufacture the virus; EEV from non-human cells will not be protected from complement-mediated clearance (complement inhibitory proteins acquired from the cell by EEV have species restricted effects). Vaccinia virus efficacy has therefore been limited by the relative sensitivity of the IMV form to neutralization and by its inefficient spread within solid tumor masses; this spread is typically from cell to adjacent cell. IMV spread to distant tumor masses, either through the bloodstream or lymphatics, is also inefficient.

Therefore, the rare EEV form of vaccinia virus has naturally acquired features that make it superior to the vaccinia virus form used in patients to date (IMV); EEV is optimized for rapid and efficient spread through solid tumors locally and to regional or distant tumor sites. Since EEV is relatively resistant to complement effects, when it is grown in a cell type from the same species, this virus form will have enhanced stability and retain activity longer in the blood following intravascular administration than standard preparations of vaccinia virus (which contain exclusively IMV) (Smith et al., 1998). Since EEV is resistant to antibody-mediated neutralization, this virus form will retain activity longer in the blood following intravascular administration than standard preparations of vaccinia virus (which contain almost exclusively IMV) (Vanderplasschen et al., 1998). This feature will be particularly important for repeat administration once neutralizing antibody levels have increased; all approved anti-cancer therapies require repeat administration. Therefore, the EEV form of vaccinia, and other poxviruses, will result in superior delivery of therapeutic viruses and their genetic payload to tumors through the bloodstream. This will lead to enhanced systemic efficacy compared with standard poxvirus preparations. Finally, the risk of transmission to individuals in the general public should be reduced significantly since EEV is extremely unstable outside of the body. Polypeptides involved in the modulation of the EEV form of a virus include, but are not limited to, A34R, B5R, and various other proteins that influence the production of the EEV form of the poxviruses. A mutation at codon 151 of A34R from a lysine to a glutamic acid (K151E mutation) renders the A34R protein less able to tether the EEV form to the cell membrane. B5R is an EEV-membrane bound polypeptide that may bind complement. The total deletion of A43R may lead to increased EEV release, but markedly reduced infectivity of the viruses, while the K151E mutation increases EEV release while maintaining infectivity of the released viruses. B5R has sequence homology to VCP (anti-complement), but complement inhibition has not yet been proven.

Briefly, one method for identifying a fortified EEV form is as follows. EEV are diluted in ice-cold MEM and mixed (1:1 volume) with active or heat-inactivated (56° C., 30 min, control) serum diluted in ice-cold MEM (final dilution of serum 1/10, 1/20, or 1/30). After incubation or 75 minutes at 7° C., samples are cooled on ice and mAb 5B4/2F2 is added to fresh EEV samples to neutralize any contaminates (IMV and ruptured EEV). Virions are then bound to RK13 cells for one hour on ice, complement and unbound virions are washed away, and the number of plaques are counted two days later. The higher the plaque number the greater the resistance to complement. Vanderplasschen et al. PNAS 1998; 95(13): 7544-7549, herein incorporated by reference. Exemplary methods describing the isolation of EEV forms of Vaccinia virus can be found in Blasco et al. 1992 (incorporated herein by reference).

7. Other Polypeptides

Other viral immunomodulatory polypeptides may include polypeptides that bind other mediators of the immune response and/or modulate molecular pathways associated with the immune response. For example, chemokine binding polypeptides such as B29R (this protein is present, but may be inactive in the Copenhagen strain of Vaccinia virus), C23L, vCKBP, A41L and polypeptides with similar activities or properties. Other vaccinia virus proteins such as the vaccinia virus growth factor (e.g., C11L), which is a viral EGF-like growth factor, may also be the target for alteration in some embodiments of the invention. Other polypeptides that may be classified as viral immunomodulatory factors include, but are not limited to B7R, N1L, or other polypeptides that whose activities or properties increase the virulence of a poxvirus.

8. Vaccinia Virus-Induced Cell Fusion

In certain embodiments of the invention an alteration, deletion, or mutation of A56R or K2L encoding nucleic genes may lead to cell-cell fusion or syncitia formation induced by VV infection. Vaccinia virus-induced cell fusion will typically increase antitumoral efficacy of VV due to intratumoral viral spread. Intratumoral vial spreading by cell fusion will typically allow the virus to avoid neutralizing antibodies and immune responses. Killing and infection of adjacent uninfected cells (i.e., a "bystander effect) may be more efficient in VV with mutations in one or both of these genes, which may result in improved local antitumoral effects.

B. Other Poxviruses

Vaccinia virus is a member of the family Poxviridae, the subfamily Chordopoxyirinae and the genus *Orthopoxvirus*. The genus *Orthopoxvirus* is relatively more homogeneous than other members of the Chordopoxyinae subfamily and includes 11 distinct but closely related species, which includes vaccinia virus, variola virus (causative agent of smallpox), cowpox virus, buffalopox virus, monkeypox virus, mousepox virus and horsepox virus species as well as others (see Moss, 1996). Certain embodiments of the invention, as described herein, may be extended to other members of *Orthopoxvirus* genus as well as the *Parapoxvirus, Avipoxvirus, Capripoxvirus, Leporipoxvirus, Suipoxvirus, Molluscipoxvirus*, and *Yatapoxvirus* genus. A genus of poxvirus family is generally defined by serological means including neutralization and cross-reactivity in laboratory animals. Various members of the Orthopoxvirus genus, as well as other members of the Chordovirinae subfamily utilize immunomodulatory molecules, examples of which are provided herein, to counteract the immune responses of a host organism. Thus, the invention described herein is not limited to vaccinia virus, but may be applicable to a number of viruses.

C. Virus Propagation

Vaccinia virus may be propagated using the methods described by Earl and Moss in Ausbel et al., Current Protocols in Molecular Biology, pages 16.15.1 to 16.18.10, which is incorporated by reference herein.

II. Proteinaceous and Nucleic Acid Compositions

The present invention concerns poxviruses that are advantageous in the study and treatment of cancer cells and cancer in a patient. It concerns poxviruses, particularly vaccinia viruses, that have been constructed with one or more mutations compared to wild-type such that the virus has desirable properties for use against cancer cells, while being less toxic or non-toxic to non-cancer cells. The teachings described below provide various protocols, by way of example, of implementing methods and compositions of the invention. They provide background for generating mutated viruses through the use of recombinant DNA technology.

A. Proteinaceous Compositions

In certain embodiments, the present invention concerns generating poxviruses that lack one or more functional polypeptides or proteins and/or generating poxviruses that have the ability to release more of a particular form of the virus, such as an infectious EEV form. In other embodiments, the present invention concerns poxviruses and their use in combination with proteinaceous composition as part of a pharmaceutically acceptable formulation.

As used herein, a "protein" or "polypeptide" refers to a molecule comprising at least one amino acid residue. In some embodiments, a wild-type version of a protein or polypeptide are employed, however, in many embodiments of the invention, a viral protein or polypeptide is absent or altered so as to render the virus more useful for the treatment of a cancer cells or cancer in a patient. The terms described above may be used interchangeably herein. A "modified protein" or "modified polypeptide" refers to a protein or polypeptide whose chemical structure is altered with respect to the wild-type protein or polypeptide. In some embodiments, a modified protein or polypeptide has at least one modified activity or function (recognizing that proteins or polypeptides may have multiple activities or functions). The modified activity or function may we reduced, diminished, eliminated, enhanced, improved, or altered in some other way (such as specificity) with respect to that activity or function in a wild-type protein or polypeptide.

It is specifically contemplated that a modified protein or polypeptide may be altered with respect to one activity or function yet retain wild-type activity or function in other respects. Alternatively, a modified protein may be completely nonfunctional or its cognate nucleic acid sequence may have been altered so that the polypeptide is no longer expressed at all, is truncated, or expresses a different amino acid sequence as a result of a frameshift.

In certain embodiments the size of a mutated protein or polypeptide may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 or greater amino molecule residues, and any range derivable therein. It is contemplated that polypeptides may be mutated by truncation, rendering them shorter than their corresponding wild-type form.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases. The coding regions for these known genes may be amplified and/or expressed using the techniques disclosed herein or as would be know to those of ordinary skill in the art.

1. Functional Aspects

When the present application refers to the function or activity of viral proteins or polypeptides, it is meant to refer to the activity or function of that viral protein or polypeptide under physiological conditions, unless otherwise specified. For example, an interferon-modulating polypeptide refers to a polypeptide that affects at least one interferon and its activity, either directly or indirectly. The polypeptide may induce, enhance, raise, increase, diminish, weaken, reduce, inhibit, or mask the activity of an interferon, directly or indirectly. An example of directly affecting interferon involves, in some embodiments, an interferon-modulating polypeptide that specifically binds to the interferon. Determination of which molecules possess this activity may be achieved using assays familiar to those of skill in the art. For example, transfer of genes encoding products that modulate interferon, or variants thereof, into cells that are induced for interferon activity compared to cells with such transfer of genes may identify, by virtue of different levels of an interferon response, those molecules having a interferon-modulating function.

It is specifically contemplated that a modulator may be a molecule that affects the expression proteinaceous compositions involved in the targeted molecule's pathway, such as by binding an interferon-encoding transcript Determination of which molecules are suitable modulators of interferon, IL-1β, INF, or other molecules of therapeutic benefit may be achieved using assays familiar to those of skill in the art—some of which are disclosed herein—and may include, for example, the use of native and/or recombinant viral proteins.

2. Variants of Viral Polypeptides

Amino acid sequence variants of the polypeptides of the present invention can be substitutional, insertional or deletion variants. A mutation in a gene encoding a viral polypeptide may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500 or more non-contiguous or contiguous amino acids of the polypeptide, as compared to wild-type. Various polypeptides encoded by Vaccinia Virus may be identified by reference to Rosel et al., 1986, Goebel et al., 1990 and Genbank Accession Number NC_001559, each of which is incorporated herein by reference.

Deletion variants lack one or more residues of the native or wild-type protein. Individual residues can be deleted or all or part of a domain (such as a catalytic or binding domain) can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of an immunoreactive epitope or simply one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a non-polar or uncharged amino acid, and vice versa.

term "functionally equivalent codon" is used herein to refer to codons that encode the same amino acid, such as the six codons for arginine or serine, and also refers to codons that encode biologically equivalent amino acids (see Table 1, below).

TABLE 1

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Gln | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

III. Nucleic Acid Molecules

A. Polynucleotides Encoding Native Proteins or Modified Proteins

The present invention concerns polynucleotides, isolatable from cells, that are capable of expressing all or part of a protein or polypeptide. In some embodiments of the invention, it concerns a viral genome that has been specifically mutated to generate a virus that lacks certain functional viral polypeptides. The polynucleotides may encode a peptide or polypeptide containing all or part of a viral amino acid sequence or they be engineered so they do not encode such a viral polypeptide or encode a viral polypeptide having at least one function or activity reduced, diminished, or absent. Recombinant proteins can be purified from expressing cells to yield active proteins. The genome, as well as the definition of the coding regions of Vaccinia Virus may be found in Rosel et al., 1986, Goebel et al., 1990, and/or Genbank Accession Number NC_00159, each of which is incorporated herein by reference.

As used herein, the term "DNA segment" refers to a DNA molecule that has been isolated free of total genomic DNA of a particular species. Therefore, a DNA segment encoding a polypeptide refers to a DNA segment that contains wild-type, polymorphic, or mutant polypeptide-coding sequences yet is isolated away from, or purified free from, total mammalian or human genomic DNA. Included within the term "DNA segment" are a polypeptide or polypeptides, DNA segments smaller than a polypeptide, and recombinant vectors, including, for example, plasmids, cosmids, phage, viruses, and the like.

As used in this application, the term "poxvirus polynucleotide" refers to a nucleic acid molecule encoding a poxvirus polypeptide that has been isolated free of total genomic nucleic acid. Similarly, a "vaccinia virus polynucleotide" refers to a nucleic acid molecule encoding a vaccinia virus polypeptide that has been isolated free of total genomic nucleic acid A "poxvirus genome" or a "vaccinia virus genome" refers to a nucleic acid molecule that can be provided to a host cell to yield a viral particle, in the presence or absence of a helper virus. The genome may or may have not been recombinantly mutated as compared to wild-type virus.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a particular polypeptide from a given species may be represented by natural variants that have slightly different nucleic acid sequences but, nonetheless, encode the same protein (see Table 1 above).

Similarly, a polynucleotide comprising an isolated or purified wild-type or mutant polypeptide gene refers to a DNA segment including wild-type or mutant polypeptide coding sequences and, in certain aspects, regulatory sequences, isolated substantially away from other naturally occurring genes or protein encoding sequences. In this respect, the term "gene" is used for simplicity to refer to a functional protein, polypeptide, or peptide-encoding unit (including any sequences required for proper transcription, post-translational modification, or localization). As will be understood by those in the art, this functional term includes genomic sequences, cDNA sequences, and smaller engineered gene segments that express, or may be adapted to express, proteins, polypeptides, domains, peptides, fusion proteins, and mutants. A nucleic acid encoding all or part of a native or modified polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs.

In particular embodiments, the invention concerns isolated DNA segments and recombinant vectors incorporating DNA sequences that encode a wild-type or mutant poxvirus polypeptide or peptide that includes within its amino acid sequence a contiguous amino acid sequence in accordance with, or essentially corresponding to a native polypeptide.

Thus, an isolated DNA segment or vector containing a DNA segment may encode, for example, a TNF modulator or TNF-modulating polypeptide that can inhibit or reduce TNF activity. The term "recombinant" may be used in conjunction with a polypeptide or the name of a specific polypeptide, and this generally refers to a polypeptide produced from a nucleic acid molecule that has been manipulated in vitro or that is the replicated product of such a molecule.

In other embodiments, the invention concerns isolated DNA segments and recombinant vectors incorporating DNA sequences that encode a polypeptide or peptide that includes within its amino acid sequence a contiguous amino acid sequence in accordance with, or essentially corresponding to the polypeptide.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode full-length polypeptide from any source or encode a truncated version of the polypeptide, for example a truncated vaccinia virus polypeptide, such that the transcript of the coding region represents the truncated version. The truncated transcript may then be translated into a truncated protein. Alternatively, a nucleic acid sequence may encode a full-length polypeptide sequence with additional heterologous coding sequences, for example to allow for purification of the polypeptide, transport, secretion, post-translational modification, or for therapeutic benefits such as targetting or efficacy. As discussed above, a tag or other heterologous polypeptide may be added to the modified polypeptide-encoding sequence, wherein "heterologous" refers to a polypeptide that is not the same as the modified polypeptide.

In a non-limiting example, one or more nucleic acid constructs may be prepared that include a contiguous stretch of nucleotides identical to or complementary to the a particular gene, such as the B18R gene. A nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100,000, 250,000, 500,000, 750,000, to at least 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values).

The DNA segments used in the present invention encompass biologically functional equivalent modified polypeptides and peptides, for example, a modified gelonin toxin. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein, to reduce toxicity effects of the protein in vivo to a subject given the protein, or to increase the efficacy of any treatment involving the protein.

In certain other embodiments, the invention concerns isolated DNA segments and recombinant vectors that include within their sequence a contiguous nucleic acid sequence from that shown in sequences identified herein (and/or incorporated by reference). Such sequences, however, may be mutated to yield a protein product whose activity is altered with respect to wild-type.

It also will be understood that this invention is not limited to the particular nucleic acid and amino acid sequences of these identified sequences. Recombinant vectors and isolated DNA segments may therefore variously include the poxvirus-coding regions themselves, coding regions bearing selected alterations or modifications in the basic coding region, or they may encode larger polypeptides that nevertheless include poxvirus-coding regions or may encode biologically functional equivalent proteins or peptides that have variant amino acids sequences.

The DNA segments of the present invention encompass biologically functional equivalent poxvirus proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein.

B. Mutagenesis of Poxvirus Polynucleotides

In various embodiments, the poxvirus polynucleotide may be altered or mutagenized. Alterations or mutations may include insertions, deletions, point mutations, inversions, and the like and may result in the modulation, activation and/or inactivation of certain pathways or molecular mechanisms, as well as altering the function, location, or expression of a gene product, in particular rendering a gene product non-functional. Where employed, mutagenesis of a polynucleotide encoding all or part of a Poxvirus may be accomplished by a variety of standard, mutagenic procedures (Sambrook et al., 1989). Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations may be induced following exposure to chemical or physical mutagens. Such mutation-inducing agents include ionizing radiation, ultraviolet light and a diverse array of chemical such as alkylating agents and polycyclic aromatic hydrocarbons all of which are capable of interacting either directly or indirectly (generally following some metabolic biotransformations) with nucleic acids. The DNA damage induced by such agents may lead to modifications of base sequence when the affected DNA is replicated or repaired and thus to a mutation. Mutation also can be site-directed through the use of particular targeting methods.

1. Random Mutagenesis a) Insertional Mutagenesis

Insertional mutagenesis is based on the inactivation of a gene via insertion of a known DNA fragment. Because it involves the insertion of some type of DNA fragment, the mutations generated are generally loss-of-function, rather than gain-of-function mutations. However, there are several examples of insertions generating gain-of-function mutations. Insertion mutagenesis has been very successful in bacteria and *Drosophila* (Cooley et al. 1988) and recently has become a powerful tool in corn (Arabidopsis; (Marks et al., 1991; Koncz et al. 1990); and Antirrhinum (Sommer et al. 1990). Insertional mutagenesis may be accomplished using standard molecular biology techniques.

b) Chemical Mutagenesis

Chemical mutagenesis offers certain advantages, such as the ability to find a full range of mutations with degrees of phenotypic severity, and is facile and inexpensive to perform. The majority of chemical carcinogens produce mutations in DNA. Benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the O4 position of thymine induced by exposure to n-nitrosoureas results in TA to CG transitions.

c) Radiation Mutagenesis

Biological molecules are degraded by ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible. Ionizing radiation causes DNA damage, generally proportional to the dose rate.

In the present invention, the term "ionizing radiation" means radiation comprising particles or photons that have sufficient energy or can produce sufficient energy to produce ionization (gain or loss of electrons). An exemplary and preferred ionizing radiation is an x-radiation. The amount of ionizing radiation needed in a given cell or for a particular molecule generally depends upon the nature of that cell or molecule and the nature of the mutation target. Means for determining an effective amount of radiation are well known in the art.

d) In Vitro Scanning Mutagenesis

Random mutagenesis also may be introduced using error prone PCR. The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale pertubations in protein conformation (Cunningham et al., 1989).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

2. Site-Directed Mutagenesis

Structure-guided site-specific mutagenesis represents a powerful tool for the dissection and engineering of protein-ligand interactions (Wells, 1996; Braisted et al., 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Zeng et al., 1996; Burton and Barbas, 1994; Yelton et al., 1995; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis. Other methods of site-directed mutagenesis are disclosed in U.S. Pat. Nos. 5,220,007; 5,284,760; 5,354,670; 5,366,878; 5,389,514; 5,635,377; and 5,789,166.

C. Vectors

To generate mutations in the poxvirus genome, native and modified polypeptides may be encoded by a nucleic acid molecule comprised in a vector. The term "vector" is used to refer to a carrier nucleic acid molecule into which an exogenous nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (1989) and Ausubel et al., 1994, both incorporated herein by reference. In addition to encoding a modified polypeptide such as modified gelonin, a vector may encode non-modified polypeptide sequences such as a tag or targetting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targetting molecule is one that directs the modified polypeptide to a particular organ, tissue, cell, or other location in a subject's body.

The term "expression vector" refers to a vector containing a nucleic acid sequence coding for at least part of a gene product capable of being bed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring" i.e., containing different elements of different transcriptional regulatory regions, and/ or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 2 lists several elements/promoters that may be employed, in the context of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |

TABLE 2-continued

Promoter and/or Enhancer

| Promoter/Enhancer | References |
|---|---|
| Papilloma Virus | Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI) × poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumali, et al., 1998), D1A dopamine receptor gene (Lee, et al., 1997), insulin-like growth factor II (Wu et al., 1997), human platelet endothelial cell adhesion molecule-1 (Almendro et al., 1996), and the SM22α promoter.

Also contemplated as useful in the present invention are the dectin-1 and dectin-2 promoters. Additional viral promoters, cellular promoters/enhancers and inducible promoters/enhancers that could be used in combination with the present invention are listed in Tables 2 and 3. Additionally any promoter/enhancer combination (as per the Eukaryotic Promoter Data Base EPDB) could also be used to drive expression of structural genes encoding oligosaccharide processing enzymes, protein folding accessory proteins, selectable maker proteins or a heterologous protein of interest. Alternatively, a tissue-specific promoter for cancer gene therapy (Table 4) or the targeting of tumors (Table 5) may be employed with the nucleic acid molecules of the present invention.

TABLE 4

Candidate Tissue-Specific Promoters for Cancer Gene Therapy

| Tissue-specific promoter | Cancers in which promoter is active | Normal cells in which promoter is active |
|---|---|---|
| Carcinoembryonic antigen (CEA)* | Most colorectal carcinomas; 50% of lung carcinomas; 40-50% of gastric carcinomas; most pancreatic carcinomas; many breast carcinomas | Colonic mucosa; gastric mucosa; lung epithelia; eccrine sweat glands; cells in testes |
| Prostate-specific antigen (PSA) | Most prostate carcinomas | Prostate epithelium |
| Vasoactive intestinal peptide (VIP) | Majority of non-small cell lung cancers | Neurons; lymphocytes; mast cells; eosinophils |
| Surfactant protein A (SP-A) | Many lung adenocarcinomas | Type II pneumocytes; Clara cells |
| Human achaete-scute homolog (hASH) | Most small cell lung cancers | Neuroendocrine cells in lung |
| Mucin-1 (MUC1)** | Most adenocarcinomas (originating from any tissue) | Glandular epithelial cells in breast and in respiratory, gastrointestinal, and genitourinary tracts |
| Alpha-fetoprotein | Most hepatocellular carcinomas; possibly many testicular cancers | Hepatocytes (under certain conditions); testis |
| Albumin | Most hepatocellular carcinomas | Hepatocytes |
| Tyrosinase | Most melanomas | Melanocytes; astrocytes; Schwann cells; some neurons |
| Tyrosine-binding protein (TRP) | Most melanomas | Melanocytes; astrocytes, Schwann cells; some neurons |
| Keratin 14 | Presumably many squamous cell carcinomas (e.g.: Head and neck cancers) | Keratinocytes |
| EBV LD-2 | Many squamous cell carcinomas of head and neck | Keratinocytes of upper digestive Keratinocytes of upper digestive tract |
| Glial fibrillary acidic protein (GFAP) | Many astrocytomas | Astrocytes |
| Myelin basic protein (MBP) | Many gliomas | Oligodendrocytes |
| Testis-specific angiotensin-converting enzyme (Testis-specific ACE) | Possibly many testicular cancers | Spermatazoa |
| Osteocalcin | Possibly many osteosarcomas | Osteoblasts |

TABLE 5

Candidate Promoters for Use with a Tissue-Specific Targeting of Tumors

| Promoter | Cancers in which Promoter is active | Normal cells in which Promoter is active |
|---|---|---|
| E2F-regulated promoter | Almost all cancers | Proliferating cells |
| HLA-G | Many colorectal carcinomas; many melanomas; possibly many other cancers | Lymphocytes; monocytes; spermatocytes; trophoblast |
| FasL | Most melanomas; many pancreatic carcinomas; most astrocytomas possibly many other cancers | Activated leukocytes: neurons; endothelial cells; keratinocytes; cells in immunoprivileged tissues; some cells in lungs, ovaries, liver, and prostate |
| Myc-regulated promoter | Most lung carcinomas (both small cell and non-small cell); most colorectal carcinomas | Proliferating cells (only some cell-types): mammary epithelial cells (including non-proliferating) |
| MAGE-1 | Many melanomas; some non-small cell lung carcinomas; some breast carcinomas | Testis |
| VEGF | 70% of all cancers (constitutive overexpression in many cancers) | Cells at sites of neovascularization (but unlike in tumors, expression is transient, less strong, and never constitutive) |
| bFGF | Presumably many different cancers, since bFGF expression is induced by ischemic conditions | Cells at sites of ischemia (but unlike tumors, expression is transient, less strong, and never constitutive) |
| COX-2 | Most colorectal carcinomas; many lung carcinomas; possibly many other cancers | Cells at sites of inflammation |
| IL-10 | Most colorectal carcinomas; many lung carcinomas; many squamous cell carcinomas of head and neck; possibly many other cancers | Leukocytes |
| GRP78/BiP | Presumably many different cancers, since GRP78 expression is induced by tumor-specific conditions | Cells at sites of ishemia |
| CarG elements from Egr-1 | Induced by ionization radiation, so conceivably most tumors upon irradiation | Cells exposed to ionizing radiation; leukocytes |

2. Initiation Signals and Internal Ribosome Binding Sites

A specific initiation signal also may be required for efficient translation of coding sequences. These signals include the ATG initiation-codon or adjacent sequences. Exogenous translational control signals, including the ATG initiation codon; may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

D. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors or viruses (which does not qualify as a vector if it expresses no exogenous polypeptides) A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris.*

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

E. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

F. Nucleic Acid Detection

In addition to their use in directing the expression of poxvirus proteins, polypeptides and/or peptides, the nucleic acid sequences disclosed herein have a variety of other uses. For example, they have utility as probes or primers for embodiments involving nucleic acid hybridization. They may be used in diagnostic or screening methods of the present invention. Detection of nucleic acids encoding poxvirus or poxvirus polypeptide modulators are encompassed by the invention.

1. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse ascription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assy (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, descried in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transition-based amplification systems (TAS), including nucleic acid sequence based amplification (NASBA) and 3SR (Kwoh et al., 1989; PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

G. Methods of Gene Transfer

Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art.

Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

H. Lipid Components and Moieties

In certain embodiments, the present invention concerns compositions comprising one or more lipids associated with a nucleic acid, an amino acid molecule, such as a peptide, or another small molecule compound. In any of the embodiments discussed herein, the molecule may be either a poxvirus polypeptide or a poxvirus polypeptide modulator, for example a nucleic acid encoding all or part of either a poxvirus polypeptide, or alternatively, an amino acid molecule encoding all or part of poxvirus polypeptide modulator. A lipid is a substance that is characteristically insoluble in water and extractable with an organic solvent. Compounds than those specifically described herein are understood by one of skill in the art as lipids, and are encompassed by the compositions and methods of the present invention. A lipid component and a non-lipid may be attached to one another, either covalently or non-covalently.

A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or amino acid molecule, such as a peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid/poxvirus-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL)-poxvirus or Superfect (Qiagen)-poxvirus complex is also contemplated.

In certain embodiments, a lipid composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 300%, about 31%, about 32%, about 33%, about 34%, about 35%, about 36%, about 37%, about 38%, about 39% about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77% about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of a particular lipid, lipid type or non-lipid component such as a drug, protein, sugar, nucleic acids or other material disclosed herein or as would be known to one of skill in the art. In a non-limiting example, a lipid composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a drug. Thus, it is contemplated that lipid compositions of the present invention may comprise any of the lipids, lipid types or other components in any combination or percentage range.

IV. Pharmaceutical Formulations, Delivery, and Treatment Regimens

In an embodiment of the present invention, a method of treatment for a hyperproliferative disease, such as cancer, by the delivery of an altered poxvirus, such as vaccinia virus, is contemplated. Examples of cancer contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, bladder cancer and any other cancers or tumors that may be treated.

An effective amount of the pharmaceutical composition, generally, is defined as that amount sufficient to detectably and repeatedly to ameliorate, reduce, minimize or limit the extent of the disease or its symptoms. More rigorous definitions may apply, including elimination, eradication or cure of disease.

Preferably, patients will have adequate bone marrow function (defined as a peripheral absolute granulocyte count of >2,000/mm$^3$ and a platelet count of 100,000/mm$^3$), adequate liver function (bilirubin <1.5 mg/dl) and adequate renal function (creatinine <1.5 mg/dl).

A. Administration

To kill cells, inhibit cell growth, inhibit metastasis, decrease tumor or tissue size and otherwise reverse or reduce the malignant phenotype of tumor cells, using the methods and compositions of the present invention, one would generally contact a hyperproliferative cell with the therapeutic compound such as a polypeptide or an expression construct encoding a polypeptide. The routes of administration will vary, naturally, with the location and nature of the lesion, and include, e.g., intradermal, transdermal, parenteral, intravenous, intramuscular, intranasal, subcutaneous, regional, percutaneous, intratracheal, intraperitoneal, intraarterial, intravesical, intratumoral, inhalation, perfusion, lavage, direct injection, and oral administration and formulation.

To effect a therapeutic benefit with respect to a vascular condition or disease, one would contact a vascular cell with the therapeutic compound. Any of the formulations and routes of administration discussed with respect to the treatment or diagnosis of cancer may also be employed with respect to vascular diseases and conditions.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising a poxvirus polypeptide or a poxvirus comprising a mutation that renders the poxyrus advantageous for treatment of cancer or cancer cells. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

The treatments may include various "unit doses.". Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher. Alternatively, depending on the kind of virus and the titer attainable, one will deliver 1 to 100, 10 to 50, 100-1000, or up to about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$ or $1\times10^{15}$ or higher infectious viral particles (vp) to the patient or to the patient's cells.

B. Injectable Compositions and Formulations

The preferred method for the delivery of an expression construct or virus encoding all or part of a poxvirus genome to cancer or tumor cells in the present invention is via intratumoral injection. However, the pharmaceutical compositions disclosed herein may alternatively be administered parenterally, intravenously, intradermally, intramuscularly, transdermally or even intraperitoneally as described in U.S. Pat. No. 5,543,158; U.S. Pat. No. 5,641,515 and U.S. Pat. No. 5,399,363 (each specifically incorporated herein by reference in its entirety).

Injection of nucleic acid constructs may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

C. Combination Treatments

The compounds and methods of the present invention may be used in the context of hyperproliferative diseases/conditions including cancer and atherosclerosis. In order to increase the effectiveness of a treatment with the compositions of the present invention, such as attenuated vaccinia viruses, it may be desirable to combine these compositions with other agents effective in the treatment of those diseases and conditions. For example, the treatment of a cancer may be implemented with therapeutic compounds of the present invention and other anti-cancer therapies, such as anti-cancer agents or surgery.

Various combinations may be employed; for example, an attenuated poxvirus, such as vaccinia virus, is "A" and the secondary anti-cancer therapy is "B":

A/B/A  B/A/B  B/B/A  A/A/B  A/B/B  B/A/A  A/B/B/B

B/A/B/B  B/B/B/A  B/B/A/B  A/A/B/B  A/B/A/B  A/B/B/A

B/B/A/A  B/A/B/A  B/A/A/B  A/A/A/B  B/A/A/A  A/B/A/A

A/A/B/A

Administration of the therapeutic expression constructs of the present invention to a patient will follow general protocols for the administration of that particular secondary therapy, taking into account the toxicity, if any, of the poxvirus treatment. It is expected that the treatment cycles would be repeated as necessary. It also is contemplated that various standard therapies, as well as surgical intervention, may be applied in combination with the described cancer or tumor cell therapy.

1. Anti-Cancer Therapy

An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver et al., 1992). In the context of the present invention, it is contemplated that poxvirus therapy could be used similarly in conjunction with chemotherapeutic, radiotherapeutic, immunotherapeutic or other biological intervention, in addition to other pro-apoptotic or cell cycle regulating agents.

Alternatively, the gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

a. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as biochemotherapy.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of certain poxvirus polypeptides would provide therapeutic benefit in the treatment of cancer.

Immunotherapy could also be used as part of a combined therapy. The general approach for combined therapy is discussed below. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to anticancer effects with immune stimulatory effects. Immune stimulating molecules also exist including: cytokines such as IL-2, IL-4, IL-12, GM-CSF, IFNγ, chemokines such as MIP-1, MCP-1, IL-8 and growth factors such as FLT3 ligand. Combining immune stimulating molecules, either as proteins or using gene delivery in combination with a tumor suppressor such as mda-7 has been shown to enhance anti-tumor effects (Ju et al., 2000).

As discussed earlier, examples of immunotherapies currently under investigation or in use are immune adjuvants (e.g., *Mycobacterium bovis*, *Plasmodium falciparum*, dinitrochlorobenzene and aromatic compounds) (U.S. Pat. No. 5,801,005; U.S. Pat. No. 5,739,169; Hui and Hashimoto, 1998; Christodoulides et al., 1998), cytokine therapy (e.g. interferons α, β and γ, IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. No. 5,830,880 and U.S. Pat. No. 5,846,945) and monoclonal antibodies (e.g. anti-ganglioside GM2, anti-HER-2, anti-p185) (Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999). Combination therapy of cancer with herceptin and chemotherapy has been shown to be more effective than the individual therapies. Thus, it is contemplated that one or more anti-cancer therapies may be employed with the poxvirus-related therapies described herein.

i) Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie and Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

ii) Active Immunotherapy

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often trasient antibodies and the exception to the rule appears to be anti-ganglioside or anticarbohydrate antibodies.

iii) Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this; one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

d. Genes

In yet another embodiment, the secondary treatment is a gene therapy in which a therapeutic polynucleotide is administered before, after, or at the same time as an attenuated poxvirus is administered. Delivery of a poxvirus in conjunction with a vector encoding one of the following gene products will have a combined anti-cancer effect on target tissues. Alternatively, the poxvirus may be engineered as a viral vector to include the therapeutic polynucleotide. A variety of proteins are encompassed within the invention, some of which are described below. Table 7 lists various genes that may be targeted for gene therapy of some form in combination with the present invention.

i) Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g. Src, Ab1 and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

ii) Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

In addition to p53, which has been described above, another inhibitor of cellular proliferation is p16. The major transitions of the eukaryotic cell cycle are triggered by cyclin-dependent kinases, or CDK's. One CDK, cyclin-dependent kinase 4(CDK4), regulates progression through the $G_1$. The activity of this enzyme may be to phosphorylate Rb at late $G_1$. The activity of CDK4 is controlled by an activating subunit, D-type cyclin, and by an inhibitory subunit, the p61$^{INK4}$ has been biochemically characterized as a protein that specifically binds to and in bits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein p16 also is known to regulate the function of CDK6.

p16$^{INK4}$ belongs to a newly descried class of CDK-inhibitory proteins that also includes p16$^B$, p19, p21$^{WAF1}$, and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1994; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, antithrombotic genes (e.g., COX-1, TFPI), PGS, Dp, E2F, ras, myc, neu, raf erb, fms, trk, ret, gsp, hst, abl, E1A, p300, genes involved in angiogenesis (e.g., VEGF, FGF, thrombospondin, BAI-1, GDAIF, or their receptors) and MCC.

iii) Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et. al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g. Bax, Bak, Bik, Bim, Bid, Bad, Harakiri).

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

f. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, agents that increase the sensitivity of the hyperproliferative cells to apoptotic inducers, or other biological agents immunomodulatory agents include tumor necrosis factor; interferon $\alpha$, $\beta$, and $\gamma$; IL-2 and other cytokines; F42K and other cytokine analogs; or MIP-1, MIP-1$\beta$, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Apo2 ligand (Apo2L, also called TRAIL) is a member of the tumor necrosis factor (TNF) cytokine family. TRAIL activates rapid apoptosis in many types of cancer cells, yet is not toxic to normal cells. TRAIL mRNA occurs in a wide variety of tissues. Most normal cells appear to be resistant to TRAIL's cytotoxic action, suggesting the existence of mechanisms that can protect against apoptosis induction by TRAIL. The first receptor described for TRAIL, called death receptor 4 (DR4), contains a cytoplasmic "death domain"; DR4 transmits the apoptosis: signal carried by TRAIL. Additional receptors have been identified that bind to TRAIL. One receptor, called DR5, contains a cytoplasmic death domain and signals apoptosis much like DR4. The DR4 and DR5 mRNAs are expressed in many normal tissues and tumor cell lines. Recently, decoy receptors such as DcR1 and DcR2 have been identified that prevent TRAIL from inducing apoptosis through DR4 and DR5. These decoy receptors thus represent a novel mechanism for regulating sensitivity to a pro-apoptotic cytokine directly at the cell's surface. The preferential expression of these inhibitory receptors in normal tissues suggests that TRAIL may be useful as an anticancer agent that induces apoptosis in cancer cells while sparing normal cells. (Marsters et al., 1999).

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia Local hyperthermia involves the application of heat to a small area, such as a tumor. Heat may be generated; externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

TABLE 6

| Gene | Source | Human Disease | Function |
|---|---|---|---|
| | | Oncogenes | |
| | | Growth Factors | |
| HST/KS | Transfection | | FGF family member |
| INT-2 | MMTV promoter Insertion | | FGF family member |
| INTI/WNTI | MMTV promoter Insertion | | Factor-like |
| SIS | Simian sarcoma virus | | PDGF B |
| | | Receptor Tyrosine Kinases | |
| ERBB/HER | Avian erythroblastosis virus; ALV promoter insertion; amplified human tumors | Amplified, deleted Squamous cell Cancer; glioblastoma | EGF/TGF-α/ Amphiregulin/ Hetacellulin receptor |
| ERBB-2/NEU/HER-2 | Transfected from rat Glioblastomas | Amplified breast, Ovarian, gastric cancers | Regulated by NDF/ Heregulin and EGF-Related factors |
| FMS | SM feline sarcoma virus | | CSF-1 receptor |
| KIT | HZ feline sarcoma virus | | MGF/Steel receptor Hematopoieis |
| TRK | Transfection from human colon cancer | | NGF (nerve growth Factor) receptor |
| MET | Transfection from human osteosarcoma | | Scatter factor/HGF Receptor |
| RET | Translocations and point mutations | Sporadic thyroid cancer; Familial medullary thyroid cancer; multiple endocrine neoplasias 2A and 2B | Orphan receptor Tyr Kinase |
| ROS | URII avian sarcoma Virus | | Orphan receptor Tyr Kinase |
| PDGF receptor | Translocation | Chronic Myelomonocytic Leukemia | TEL(ETS-like Transcription factor)/ PDGF receptor gene Fusion |
| TGF-β receptor | | Colon carcinoma Mismatch mutation target | |
| | | NONRECEPTOR TYROSINE KINASES | |
| ABI. | Abelson Mul.V | Chronic myelogenous Leukemia translocation with BCR | Interact with RB, RNA Polymerase, CRK, CBL |
| FPS/FES | Avian Fujinami SV; GA FeSV | | |
| LCK | Mul.V (murine leukemia virus) promoter insertion | | Src family; T cell Signaling; interacts CD4/CD8 T cells |
| SRC | Avian Rous sarcoma Virus | | Membrane-associated Tyr kinase with signaling function; activated by receptor kinases |
| YES | Avian Y73 virus | | Src family; signaling |
| | | SER/THR PROTEIN KINASES | |
| AKT | AKT8 murine retrovirus | | Regulated by PI(3)K?; regulate 70-kd S6 k? |
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS Pathway |

TABLE 6-continued

| Oncogenes | | | |
|---|---|---|---|
| Gene | Source | Human Disease | Function |
| MISCELLANEOUS CELL SURFACE | | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and Drosophiia homology | Nevoid basal cell cancer Syndrome (Gorline syndrome) | 12 transmembrane domain; signals through Gli homogue CI to antagonize Hedgehog pathway |
| TAN-1 Notch homologue | Translocation | T-ALI. | Signaling |
| MISCELLANEOUS SIGNALING | | | |
| BCL-2 | Translocation | B-cell lymphoma | Apoptosis |
| CBL | Mu Cas NS-1 V | | Tyrosine-Phosphorylated RING finger interact Abl |
| CRK | CT1010 ASV | | Adapted SH2/SH3 interact Abl |
| DPC4 | Tumor suppressor | Pancreatic cancer | TGF-β-related signaling Pathway |
| MAS | Transfection and Tumorigenicity | | Possible angiotensin Receptor |
| NCK | | | Adaptor SH2/SH3 |
| GUANINE NUCLEOTIDE EXCHANGERS AND BINDING PROTEINS | | | |
| BCR | | Translocated with ABL in CML | Exchanger; protein Kinase |
| DBL | Transfection | | Exchanger |
| GSP | | | |
| NF-1 | Hereditary tumor Suppressor | Tumor suppressor Neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many human tumors | Signal cascade |
| VAV | Transfection | | S112/S113; exchanger |
| NUCLEAR PROTEINS AND TRANSCRIPTION FACTORS | | | |
| BRCA1 | Heritable suppressor | Mammary Cancer/ovarian cancer | Localization unsettled |
| BRCA2 | Heritable suppressor | Mammary cancer | Function unknown |
| ERBA | Avian erythroblastosis Virus | | Thyroid hormone receptor (transcription) |
| ETS | Avian E26 virus | | DNA binding |
| EVII | MuLV promotor Insertion | AML | Transcription factor |
| FOS | FBI/FBR murine osteosarcoma viruses | | Transcription factor with c-JUN |
| GLI | Amplified glioma | Glioma | Zinc finger; cubitus Interruptus homologue is in hedgehog signaling pathway; inhibitory link PTC and hedgehog |
| HMGI/LIM | Translocation t(3:12) t(12:15) | Lipoma | Gene fusions high mobility group HMGI-C (XT-hook) and transcription factor LIM or acidic domain |
| JUN | ASV-17 | | Transcription factor AP-1 with FOS |
| MLL/VHRX + ELI/MEN | Translocation/fusion ELL with MLL Trithorax-like gene | Acute myeloid leukemia | Gene fusion of DNA-binding and methyl transferase MLL with ELI RNA pol II Elongation factor |
| MYB | Avian myeloblastosis Virus | | DNA binding |

TABLE 6-continued

| Oncogenes | | | |
|---|---|---|---|
| Gene | Source | Human Disease | Function |
| MYC | Avian MC29; Translocation B-cell Lymphomas; promoter Insertion avian leukosis Virus | Burkitt's lymphoma | DNA binding with MAX partner; cyclin Regulation; interact RB?; regulate Apoptosis? |
| N-MYC | Amplified | Neuroblastoma | |
| L-MYC | | Lung cancer | |
| REL | Avian Retriculoendotheliosis Virus | | NF-κB family Transcription factor |
| SKI | Avian SKV770 Retrovirus | | Transcription factor |
| VHL | Heritable suppressor | Von Hippel-Landau Syndrome | Negative regulator or elongin; transcriptional elongation complex |
| WT-1 | | Wilm's tumor | Transcription factor |
| CELL CYCLE/DNA DAMAGE RESPONSE | | | |
| ATM | Hereditary disorder | Ataxia-telangiectasia | Protein/lipid kinase Homology; DNA damage response upstream in P53 pathway |
| BCL-2 | Translocation | Follicular lymphoma | Apoptosis |
| FACC | Point mutation | Fanconi's anemia group C (predisposition Leukemia | |
| FHIT | Fragile site 3p14.2 | Lung carcinoma | Histidine triad-related Diadenosine 5',3''''- $P^1.p^4$ tetraphosphate Asymmetric hydrolase |
| hMLI/MutL | | HNPCC | Mismatch repair; MutL Homologue |
| HMSH2/MutS | | HNPCC | Mismatch repair; MutS Homologue |
| HPMS1 | | HNPCC | Mismatch repair; MutL Homologue |
| hPMS2 | | HNPCC | Mismatch repair; MutL Homologue |
| INK4/MTS1 | Adjacent INK-4B at 9p21; CDK complexes | Candidate MTS1 Suppressor and MLM melanoma gene | p16 CDK inhibitor |
| INK4B/MTS2 | | Candidate suppressor | p15 CDK inhibitor |
| MDM-2 | Amplified | Sarcoma | Negative regulator p53 |
| p53 | Association with SV40 T antigen | Mutated >50% human Tumors, including hereditary Li-Fraumeni syndrome | Transcription factor; Checkpoint control; apoptosis |
| PRAD1/BCL1 | Translocation with Parathyroid hormone or IgG | Parathyroid adenoma; B-CLL | Cyclin D |
| RB | Hereditary Retinoblastoma; Association with many DNA virus tumor Antigens | Retinoblastoma; Osteosarcoma; breast Cancer; other sporadic Cancers | Interact cyclin/cdk; regulate E2F transcription factor |
| XPA | | Xeroderma Pigmentosum; skin Cancer predisposition | Excision repair; photo-product recognition zinc finger |

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Vaccinia Virus Propagation in Cell Lines

A panel of 16 different routinely available vaccinia virus laboratory strains/available mutants (and rabbitpox, and other poxviruses) was evaluated: Copenhagen, Dairen, Evans, USSR, Tashkent, Tian Tan, WR, IHD-J, IED-W, Lister, NYCBOH, Patwadangar, King, and WR mutants B8R, B18R and B13R. Replication was assessed in both cancer cells and in normal cells. A preferred virus would have relatively high replication in the cancer cells and reduced replication in normal cells (i.e., a larger therapeutic ratio or index between tumor and normal cells). Two human tumor cell lines were tested: A2780 colon carcinoma and HCT116 colon carcinoma (American Type Culture Collection). Normal cells included normal human bronchial epithelial (NHBE) cells. For cytopathic effect assays using proliferating cells, cells were grown to 70% confluence (DMEM with 2% FBS) at which time cells were infected with multiplicities of infection (MOI) of 0.001 to 10. Five to six days later plates were stained with MTT (Promega) and the absorbance quantitated. Normal cells were made non-proliferative following growth to complete confluence and subsequent culture in DMEM with 0.2% FBS. Lack of proliferation was confirmed by cell cycle analysis and cell counts. Each sample was assayed in quaduplicate and was repeated at least twice. For viral replication assays, cells were grown to 70% confluence (37° C., 5% $CO^2$, DMEM with 2% FBS with additional growth factor supplementation for NHBE cells—as in Heise et al., (2000) at which time cells were infected with multiplicities of infection (MOI, particles per cell ratio) of 1 or 10 with each virus. After a three hour incubation the medium was removed and replaced with fresh supplemented media. Forty-eight hours later (previous data had demonstrated that vaccinia replication peaked at this time-point), both cells and supernatant were harvested for virus titration analysis. Cell lysates underwent three cycles of freezing and thawing, followed by a 30 second pulse in a sonicator/water bath. Virus was then purified through a sucrose cushion and serial dilutions of supernatants and lysates were titered on BSC-1 cells purification and titration as described in Alcami and Smith, (1995).

Figure 2:
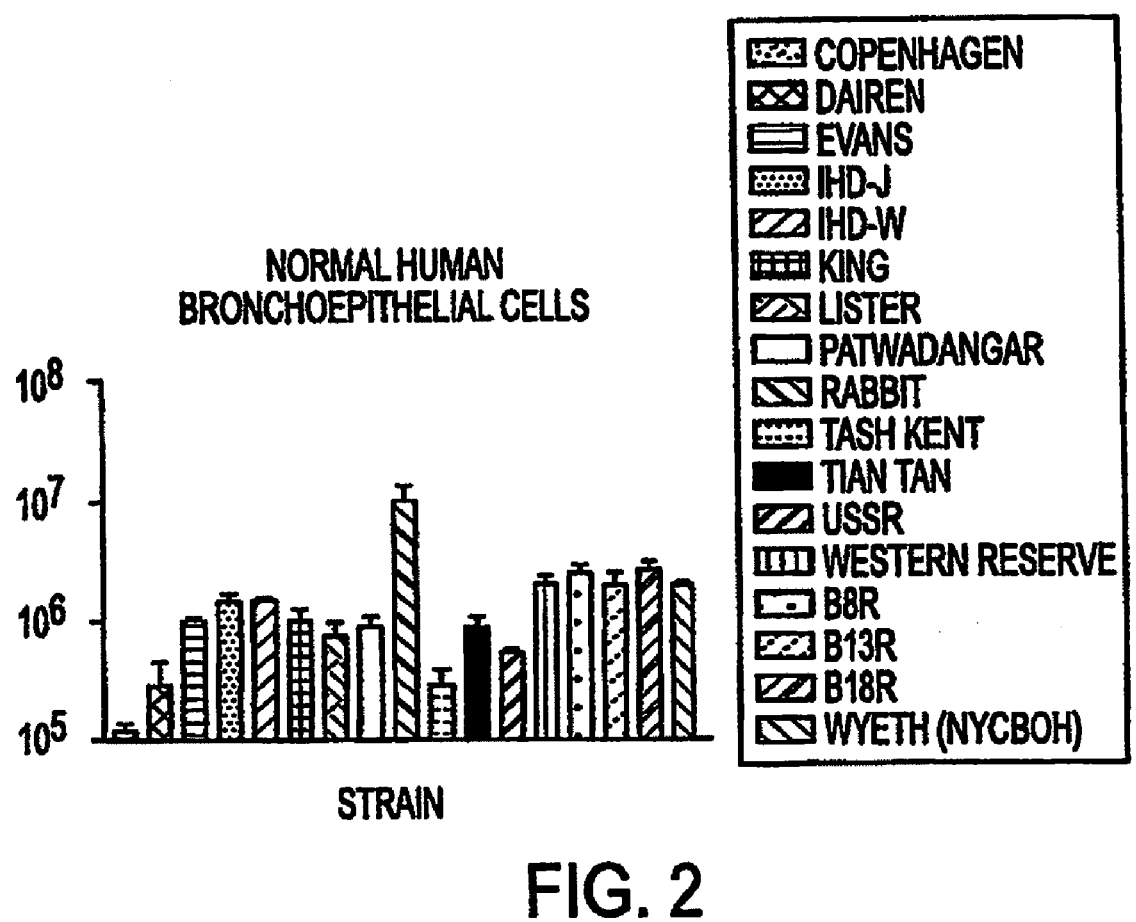
FIG. 2 illustrates an example of vaccinia virus strain replication in normal human bronchioepithelial cells (NHBE). (x-axis is the strain and the y-axis is plaque forming units per ml +/−S.E.)
Figure 3:
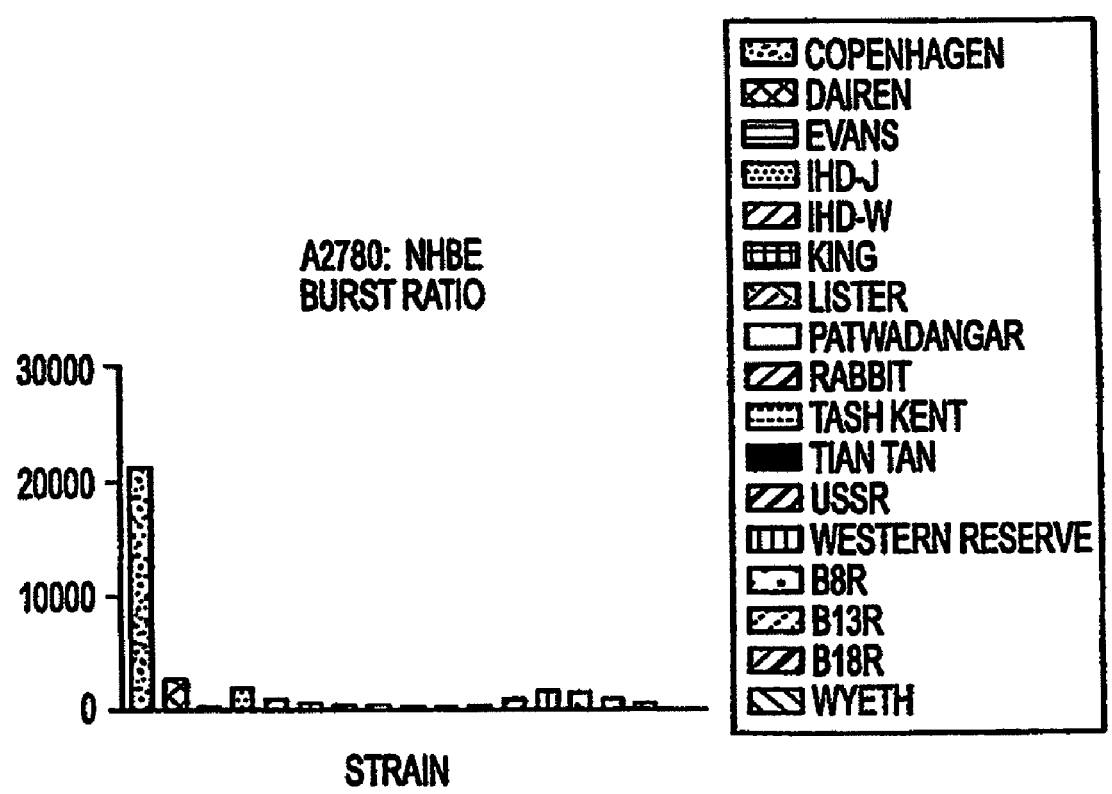
FIG. 3 illustrates an example of the ratio of burst in cancer cells (A2780) to normal cells (NBBE) (burst ratio) for vaccinia virus strains. (x-axis is the strain and the y-axis is the burst ratio).
Figure 4:
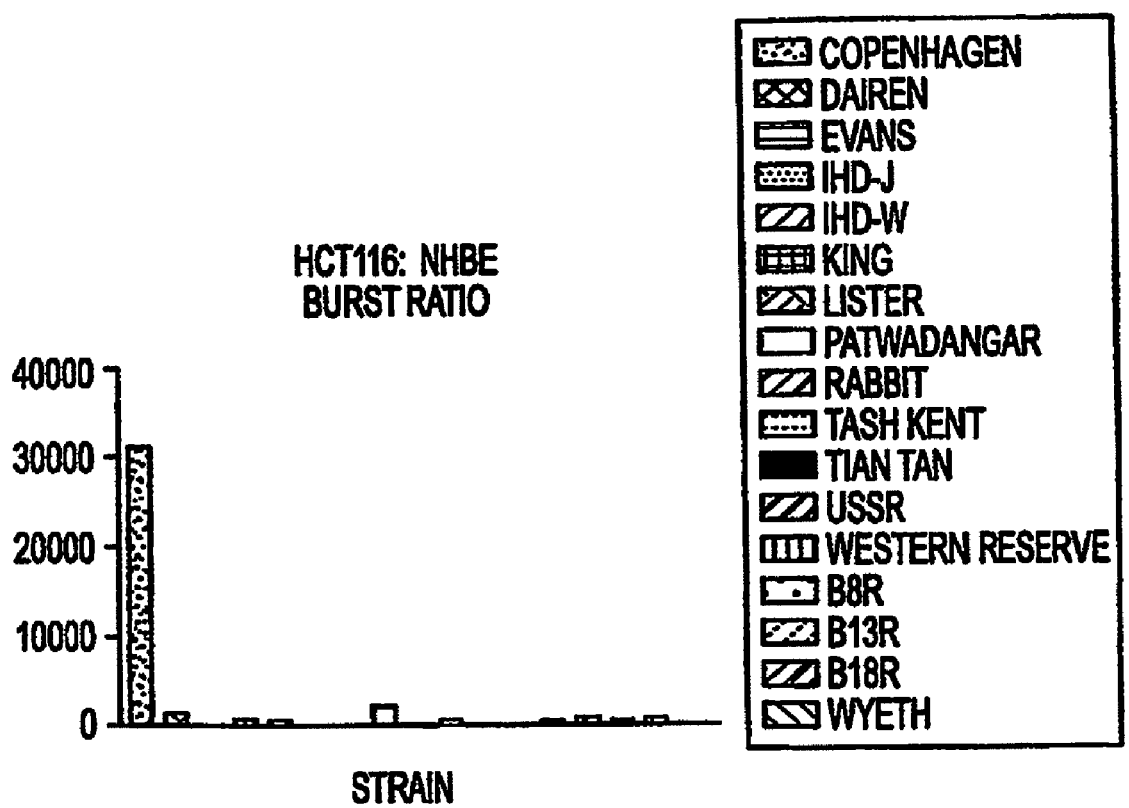
FIG. 4 illustrates an example of the ratio of burst in cancer cells (HCT116) to normal cells (NHBE) (burst ratio) for vaccinia virus strains. (x-axis is the strain and the y-axis is the burst ratio). Burst ratio is the ratio between PFU for a tumor cell compared to the PFU for a normal or non-tumor cell.

Exemplary results are shown in FIG. 1-4. The replication of Copenhagen virus in the two carcinoma lines was equivalent or superior to all other viruses in the assays (FIGS. 1A and 1B; y-axis is plaque-forming units per ml +/−S.E.). In contrast, in the normal human cells Copenhagen was attenuated relative to other viruses (FIG. 2). Finally, the ratio of the burst in cancer cells to normal cells are shown for all viruses in FIG. 3 (A2780: NHBE) and FIG. 4 (HCT116: NHBE). Copenhagen had a significantly greater burst ratio in both A2780 ($P<0.001$) and HCT116 ($p<0.001$). While the burst ratio was approximately 20,000 and 30,000 for Copenhagen, respectively, all other viruses had ratios less than five thousand, and most were less than two thousand (e.g., Lister and Wyeth). Similarly, the tumor cell killing by Copenhagen in cytopathic effect assays in vitro in A2780 and HCT116 was greater than or equal to Lister and NYCBOH strains.

Example 2

Vaccinia Virus in Combination with Paclitaxel

Although viruses such as adenovirus and HSV have been tested in combination with chemotherapy, vaccinia viruses have not (including the Copenhagen strain). VV has been engineered to express prodrug-activating enzymes (e.g. thymide kinase) have been tested in combination with relatively non-toxic prodrugs that become toxic following activation by the prodrug-activating gene product (Puhlmann et al., 2000).

Figure 5A:
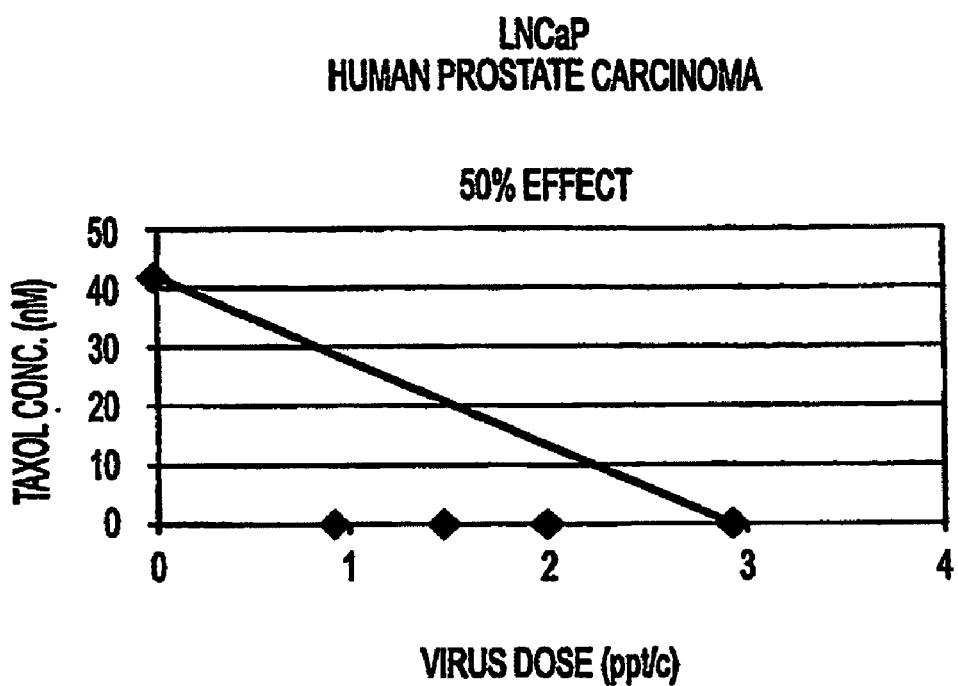
FIGS. 5A and 5B illustrate exemplary isobologram analysis derived from the data presented in FIGS. 6, 7, 8, and 9 exemplifying synergy between vaccinia virus (Copenhagen strain) and paclitaxel in HCT116 (FIG. 5B) and LNCaP (FIG. 5A) cell lines.
Figure 5B:
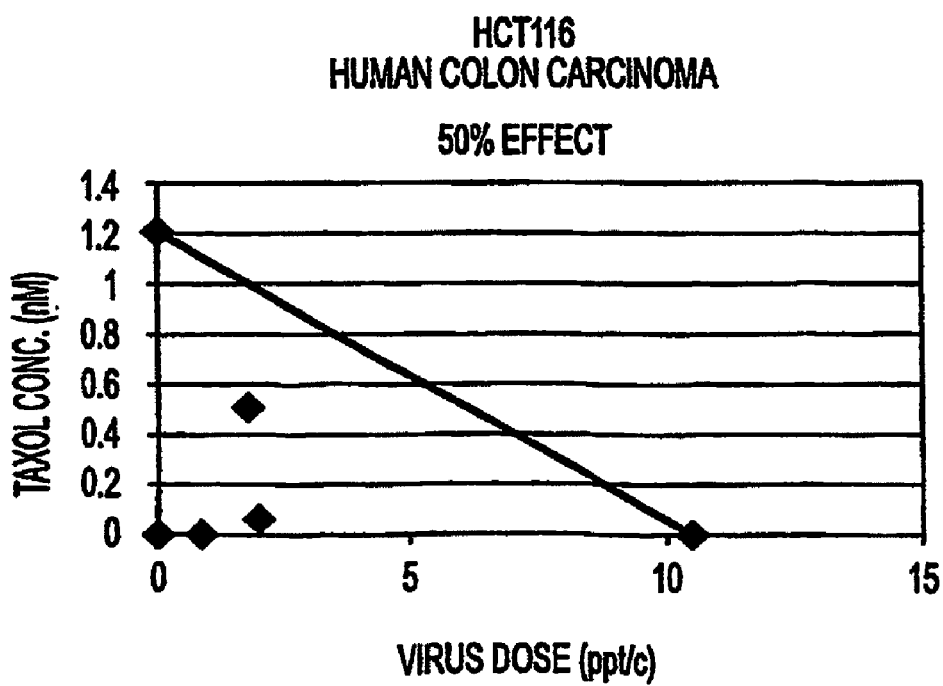
Figures 6A, 6B, 6C:
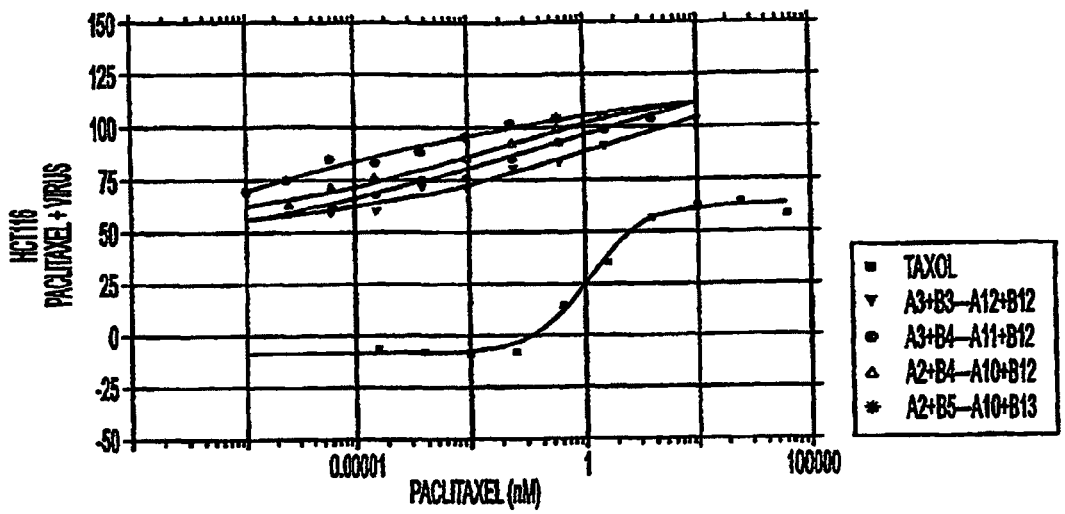
FIG. 6 illustrates exemplary HCT116 cell proliferation data derived from an exemplary MTS assay using combinations of paclitaxel and vaccinia virus.
Figures 7A, 7B, 7C:
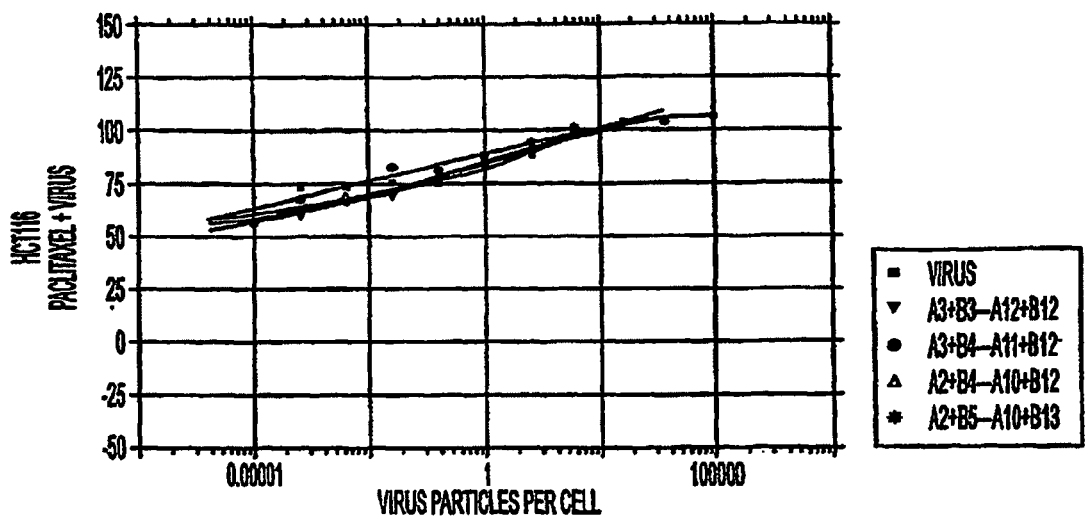
FIG. 7 illustrates exemplary HCT116 cell proliferation data derived from an exemplary MTS assay using combinations of paclitaxel and vaccinia virus.
Figures 8A, 8B, 8C:
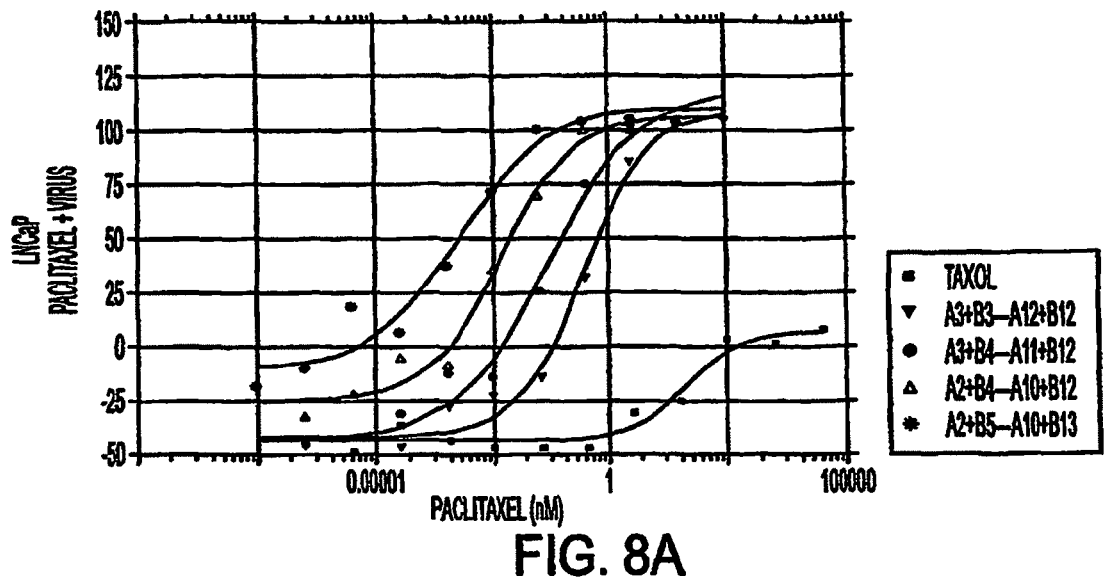
FIG. 8 illustrates exemplary LNCaP cell proliferation data derived from an exemplary MTS assay using combinations of paclitaxel and vaccinia virus.
Figures 9A, 9B, 9C:
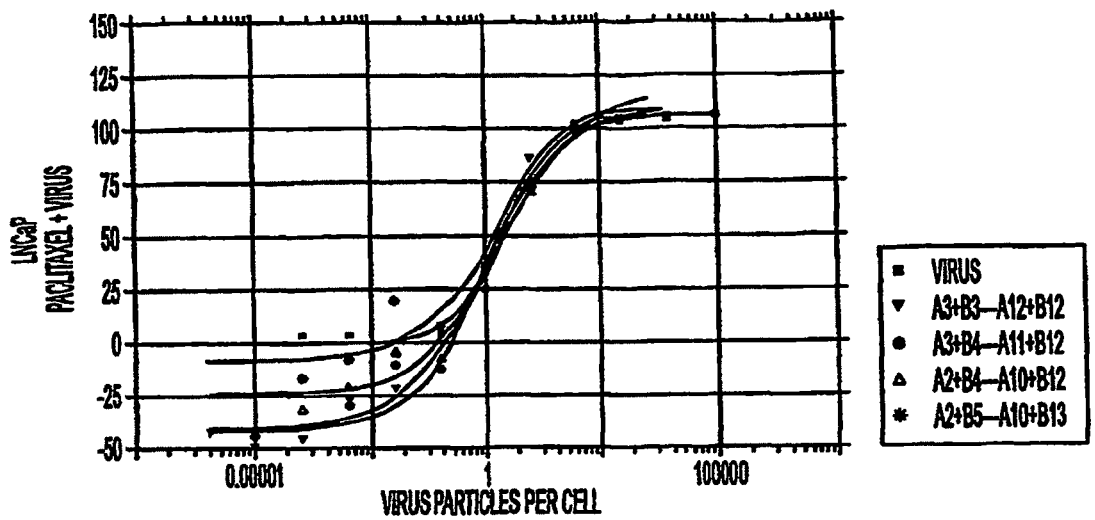
FIG. 9 illustrates exemplary LNCaP cell proliferation data derived from an exemplary MTS assay using combinations of paclitaxel and vaccinia virus.

Synergy between standard cytotoxic chemotherapeutics that are approved for the treatment of cancer patients and Vaccinia viruses would be an favorable feature for a poxvirus, including vaccinia and specifically Copenhagen strain. Paclitaxel (a.k.a taxol) is approved for use in cancer patients in the U.S. and Europe. VV Copenhagen were tested in combination with Taxol in both HCT116 and LNCaP cancer cell lines. Isobologram generation and analysis has shown synergy of VV in combination with Taxol (FIG. 5). Isobolograms were generated using data derived from a MTS assay, such as the CellTiter96®AQueous Non-Radioactive Cell Proliferation Assay (Catalog #G5421, Promega Corp., Madison, Wis.), on cell survival illustrated in FIGS. 6, 7, 8, and 9. All data points in FIG. 5 lie beneath the line that symbolizes the expected positions of the datapoints if no synergy nor antagonism were present; therefore these data points are supportive of a synergistic interaction in the killing of these carcinoma cell lines.

The methods included growing cell lines in 96 well dishes in 5% $CO^2$ at 37° DMEM plus 10% FCS. Once cells reached approximately 50% confluency the medium was changed to DMEM plus 2% FCS and they were treated with paclitaxel (dose range $3\times10^{-8}$ to $3\times10^4$ nM, log increments) and/or virus (VV Copenhagen at MOI of $10^{-6}$ to $10^5$ particles per cell). Cells were either 1) mock-treated, 2) virus-treated only, 3) taxol-treated only, 4) virus-treated followed by taxol treatment. Cells were infected for 6 days total and were then put into the MTS assay (Promega, Wis. USA see manufacturers instructions). Cells were exposed to taxol for 6 days total and were then put into the MTS assay (see manufacturers instructions). Cells treated with the combination were infected in identical fashion to the virus-only treatment group and were subsequently treated with taxol (in fixed ratios of virus:taxol) immediately as above. Cells were then assayed as above. MTS cell survival data was expressed as percentage of control cell survival as in FIGS. 6, 7, 8, and 9. Data analysis for evaluation of synergy (isobolgram generation and analysis) was as described in Nielsen et al. (1997, 1998). Briefly, dose response curves were generated to calculate the $EC_{50}$ values for each cell line (compared to untreated cells) for each cell (i.e., and all test conditions). Nine concentrations of each agent were used (see above) alone and in combination. Four different dilution ratios for VV/paclitaxel were included in each experiment (3, 33, 333, 3333). Isobolograms were generated to determine synergistic or antagonistic effects. Each data point represented triplicate samples.

Example 3

Tumor Regression Results from Vaccinia Virus Administration

Subcutaneous murine tumor xenografts were formed by injecting $5\times10^5$ CMT-64 cells or $10^6$ CMT-93 cells (murine rectal carcinoma) suspended in 100 μl PBS subcutaneously into the flanks of C57B/6 mice. In the first experiment, VV WR strain mutants in B8R and B18R were; injected into subcutaneous CMT-93 tumors (estimated baseline tumor sizes 40-100 μl) in the flanks of immunocompetent C57/B6 mice at doses of $10^4$ to $10^8$ particles suspended in 40 μl per day on days 1, 3 and 5. A single needle puncture was made in the center of the tumor and four needle tracts were made out into each tumor quadrant. Approximately one-fourth of the solution was injected into each tract as the needle was being withdrawn. Controls received identical treatment with psoralen-UV inactivated virus or PBS. Bidimensional tumor measurements were performed biweekly and the tumor volume established by the following formula: (length)(width)(width) (3.14/6).

Significant antitumoral effects and increased survival were demonstrated compared to vehicle or inactivated virus control-injected tumors, and a dose-response relationship was seen. Eight of ten mice treated with $10^8$ or $10^{10}$ B8R mutant- VV had complete tumor regressions and remained tumor-free throughout follow-up (3 months total). Nine of ten mice receiving B18R at the same dose levels had complete regressions and remained tumor-free throughout the same follow-up period. Only one durable complete regression was noted in the control groups. Median survival was two weeks and all mice were sacrificed by day 24 post-treatment initiation. Survival was significantly increased in the $10^8$ to $10^{10}$ particle treatment groups (KM survival analysis, log rank test; p<0.01). Animals were observed for gross appearance (e.g. activity, ruffled fur) and weighed twice weekly, no significant weight or appearance changes were reported.

The identical treatment/injection regimen was then performed with B18R and vehicle control in the CMT-64 murine tumor xenograft model. Although, no complete responses were demonstrated, delay in the time to tumor progression requiring sacrifice was highly significant for the B18R-treatment group versus PBS or psoralen-UV-inactivated virus (median approximately 2 weeks versus 4 weeks; p<0.05, log rank test, Kaplan-Meier analysis of time to sacrifice due to tumor progression).

Example 4

EEV-Enhanced Efficacy Regarding Murine Tumor Xenografts

Subcutaneous murine tumor xenografts were formed by injecting $5 \times 10^5$ JC murine breast carcinoma cells suspended in 100 µl PBS subcutaneously into the flanks of immunocompetent BALB/c mice. Western Reserve (WR without the IHD-J mutation) VV, the IHD-J mutant of WR (A34R/K151E mutation) virus or PBS was injected into the subcutaneous JC tumors, once they reached injectable sizes (baseline tumor sizes 40-100 µl). Virus doses were $10^{10}$ particles per day, suspended in 40 µA PBS, on days 1, 3 and 5 (n=8 mice per treatment group). A PBS control was injected in a similar regimen. A single needle puncture was made in the center of the tumor and four needle tracts were made out into each tumor quadrant. Approximately one-fourth of the solution was injected into each tract as the needle was being withdrawn. Controls received identical treatment with PBS. Bidimensional tumor measurements were performed biweekly and the tumor volume estimated by the following formula: (length)(width)(width)(3.14/6).

The IHD-J-treated group demonstrated significant antitumoral effects (tumor growth delay and tumor shrinkage) and increased time-to-tumor-progression requiring sacrifice (i.e. survival) compared to PBS-treated or Western Reserve-treated groups. Based on Kaplan-Meier survival analysis, the time-to-tumor-progression requiring sacrifice (survival) of the IHD-J group was significantly superior to both PBS (p-value <0.05) and WR (p-value <0.05) based on the log rank statistical test (used to compare survival curves). The median survival time was 2 weeks for the two control groups versus 4.5 weeks for IHD-J. None of the mice in any treatment group demonstrated any significant gross toxicity and no treatment-related animal deaths occurred. The IHD-J mutation led to a significant improvement in antitumoral efficacy (compared to the WR virus without the IHD-J mutation) without increased toxicity. Tumors will be grown subcutaneously and treatment will be initiated when they reach 2-6 mm in diameter.

Example 5

Figure 10:
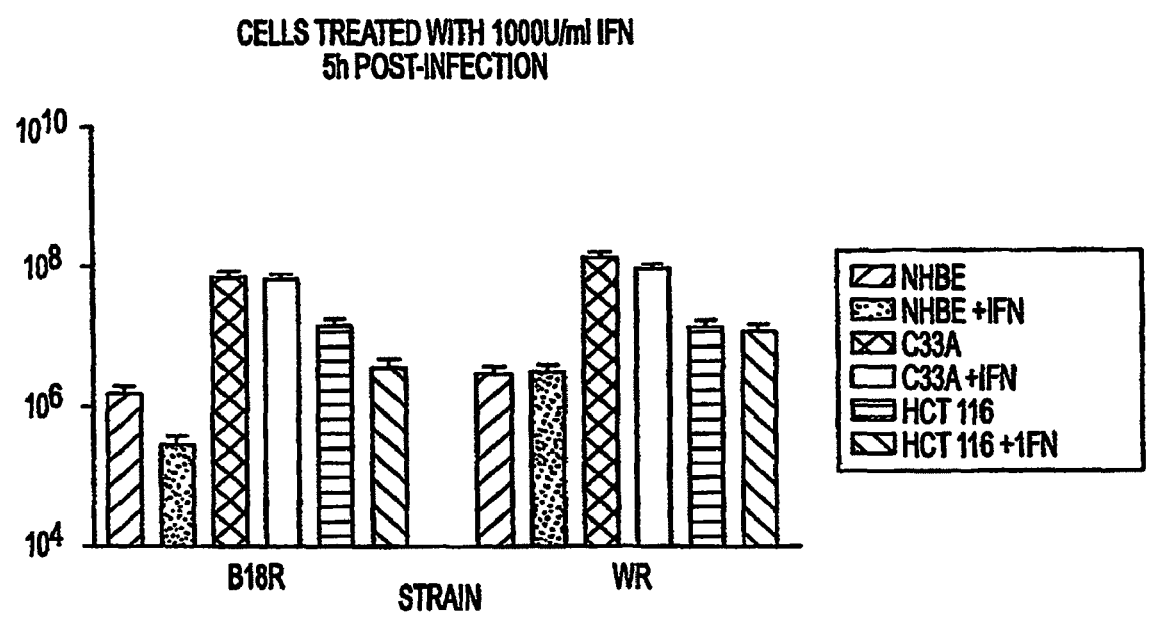
FIG. 10 illustrates an exemplary study where IFN-resistant and IFN-sensitive cells were infected with WR or WR-B18R (−) +/−IFN treatment (treated 5 hours post infection with IFN-alpha).

Deletion of Interferon-Binding Gene and Increased Selectivity for IFN-Resistant Cancer Cells Versus Normal Cells Studies were carried out to assess whether poxviruses with deletions in interferon binding genes had greater tumor-selectivity, and reduced replication in normal cells, compared to a wildtype control poxvirus. WR (Western Reserve) and a WR mutant with a deletion in the B18R gene (B18R) were compared for replication in the presence or absence of IFN-alpha (1,000 Units/ml applied 5 hours after infection in vitro) (FIG. 10). Cells tested were the normal human bronchial epithelial cells (NHBE, Clonetics Corp., USA), C33A human cervical carcinoma cells (ATCC) and HCT116 human colon carcinoma cells (ATCC). In a pilot study, these cells were initially pretreated with IFN (5,000 Units/ml) for 24 hours prior to infection with these viruses to determine their sensitivity to interferon effects on viral replication. As expected, both viruses were equally sensitive to suppression by interferon pre-treatment. The NHBE and HCT116 cells were demonstrated to be IFN-sensitive since viral replication was significantly reduced in the presence of IFN pretreatment; C33A cells were IFN-resistant since IFN-pretreatment had no significant impact on viral replication.

Cancer cells were grown in DMEM with 10% FCS; normal cells were grown in DMEM with serum supplementation as described in the supplier's instructions. Cells were infected at a multiplicity-of-infection (moi) of 10 particles per cell when cells reached approximately 70% confluency. Five hours after infection, IFN was either added to the medium at a concentration of 1,000 Units/ml (IFN+ cells) or not (IFN− cells). Cells and lysate were harvested 48 hours after infection and standard VV isolation and virus titrations (plaque-forming unit determination) were performed (titration on BS-C-1 cells as described by Tscharke et al., 2002, incorporated herein by reference). As shown in FIG. 10, VV with a mutation in B18R have significantly inhibited replication in the presence of IFN in the two IFN-sensitive cell types, including NHBE (p<0.01, student's t-test versus in the absence of IFN). In contrast, this mutant virus is not inhibited in the IFN-resistant C33A carcinoma cells. As expected, the wildtype WR was not affected by IFN treatment due to the presence of the functional B18R gene product (P=0.8). Similar results were obtained with other IFN-resistant carcinoma cell lines. Therefore, deletion of the IFN-binding gene B18R resulted in an increased therapeutic index and normal cell protection compared to the wildtype virus.

IFN-binding mutants in B8R and B18R also demonstrated antitumoral efficacy in a murine tumor xenograft model. The relative safety enhancement resulting from B18R and/or B8R deletion will be underestimated in mice since murine versions of the target IFN molecules are bound with significantly reduced affinity (Symons et al., 2002). Additional studies may be performed using intradermal injection studies performed in rabbits or non-human primates using the methods described in Symons, et al. and results may be obtained that are similar to the results reported therein for rabbits (B8R mutant VV demonstrated increased inflammatory cell recruitment and as a result accelerated clearance of the virus from the skin lesions compared with wildtype control). Therefore, both antitumoral efficacy and accelerated viral clearance from normal cells has been demonstrated in vitro and may be demonstrated in vivo (Symons et al).

Example 6

Prophetic Example to Show Effect of Loss of TNF-Modulating Function

Matched viruses with and without deletion/inactivation of one or more cytokine- or chemokine-inhibitory genes (e.g., wild-type WR vaccinia and a mutant with a deletion in B29R/vCKBP) will be used to infect murine tumors (e.g. CMT-93, CMT-64 or JC) in immunocompetent (C57B/6 or BALB/c) mice. This comparison will only be valid if the viral gene product is able to inhibit the murine cytokines/chemokines to a degree similar to that for the human version. Viral replication (plaque-forming units over time), CC chemokine levels (e.g., immunohistochemical staining or ELISA assay), cytokine levels (e.g., immunohistochemical (IHC) staining or ELISA assay) and inflammatory cell infiltration (H and E or IHC staining) will be evaluated in tumor tissues and normal tissues following intravenous and/or intratumoral administration (viral particles form $10^5$ to $10^{10}$, administered for 1 to 6 doses). In addition, the antitumoral efficacy (Kaplan-Meier tumor regression/survival curves) and toxicity (weight loss; hematology, and serum chemistry test) of both viruses will be evaluated. The result would be that the mutant virus(es) would demonstrate 1) enhanced efficacy and inflammation induction within tumors (e.g., increased immune effector cell recruitment; 2) similar or reduced replication and toxicity in normal tissues (e.g. liver, spleen, lung and/or brain); 3) and enhanced or maintained induction of tumor-specific cell-mediated immunity. Finally, antitumoral efficacy in combination with chemotherapy and/or radiotherapy is expected to be greater with the mutant virus(es) than with the wild-type virus. Toxicity studies may also be conducted in rabbits or non-human primtes to further characterize a virus of the present invention (Tscharke et al., 2002, incorporated herein by reference).

Example 7

Prophetic Example to Show Effect of Loss of Interferon-Modulating Function

Matched viruses with and without deletion/inactivation of one or more interferon-binding polypeptides (e.g., wild-type WR vaccinia and a mutant with a deletion in B18R) will be used to infect tumors in immunocompetent animals whose target IFN molecules are efficiently bound by the vaccinia virus gene product, as discussed in the previous examples. Of note, since murine interferon is relatively resistant to VV polypeptide(s) compared with human interferon, results in mice are expected to be much less significant than they will be in humans. Viral replication and spread in tumor tissues and normal tissues will be evaluated following intravenous and/or intratumoral administration, as described above. In addition, the antitumoral efficacy and toxicity of both viruses will be evaluated, as described above. The expected result would be that the mutant virus(es) would demonstrate reduced replication and toxicity in normal tissues (e.g., liver, spleen, lung and/or brain) but that replication and necrosis induction would still occur in tumors. The wildtype vaccinia (e.g., WR) will demonstrate a smaller differential of replication/necrosis induction between normal and tumor tissues. In addition, the tumors treated with the mutant virus(es) will have reduced vascularity (e.g., by H and E staining, IHC for CD31 on equivalent vascular markers) compared to saline-treated controls and wild-type virus-treated control tumors. Finally, immune-mediated antitumoral efficacy and efficacy in combination with chemotherapy and/or radiation is expected to be greater with the mutant virus(es) than with the wild-type virus. Toxicity studies may also be conducted in rabbits or non-human primates to further characterize a virus of the present invention (Tscharke et al., 2002, incorporated herein by reference).

Example 8

Prophetic Example to Show Effect of Loss of Serine Protease Inhibitor Function

Matched viruses with and without deletion/inactivation of anti-apoptosis genes could be used to infect tumors in immunocompetent mice, as described above. Viruses include but are not limited to vaccinia viruses with or without expression of B13R (SPI-2). Viral replication and spread in tumor tissues and normal tissues would be evaluated following intravenous administration, as described above. In addition, the antitumoral efficacy and toxicity of mutant viruses would be evaluated following intratumoral and/or intravenous administration, as described above. The expected result would be that the mutant viruses would demonstrate reduced replication and toxicity in normal tissues, and/or would be cleared faster from normal tissues, compared to tumor tissues. The wild-type virus would show a smaller differential (if any) between replication and toxicity in normal tissues compared to that in tumor tissues. The antitumoral efficacy of the mutant virus(es), following intratumoral, intraperitoneal, intravenous or other routes of administration, is expected to be equivalent or superior to efficacy with the wild-type virus. Combination chemotherapy studies would use the same model system. Mice would receive vehicle (placebo), chemotherapy alone, virus alone (wild-type or mutant) or virus plus chemotherapy. The efficacy with the mutant virus plus chemotherapy is expected to be superior to chemotherapy alone and to wild-type virus plus chemotherapy. Similar findings are expected in combination with radiotherapy.

Example 9

Prophetic Example to Show Effect of Loss of Complement Control Function

Matched viruses with and without deletion/inactivation of VCP genes could be used to infect tumors in immunocompetent mice, as described above. Viral replication and spread in tumor tissues and normal tissues would be evaluated following intravenous or other routes of administration, as described above. In addition, the antitumoral efficacy and toxicity of mutant viruses would be evaluated, as described above, following intratumoral and/or intravenous administration. The expected result would be that the mutant viruses would demonstrate reduced replication and toxicity in normal tissues, and/or would be cleared more efficiently from normal tissues, compared to tumor tissues. The wild-type virus would show a smaller differential (if any) between replication and toxicity in normal tissues compared to that in tumor tissues. The antitumoral efficacy of the mutant virus(es), following intratumoral, intraperitoneal, intravenous or other routes of administration, would be equivalent or superior to efficacy with the wild-type virus. Combination therapy studies would use the same model system. For example, mice would receive vehicle (placebo), chemotherapy alone, virus alone (wild-type or mutant) or virus plus chemotherapy. The efficacy with the mutant virus plus chemotherapy is expected to be superior to chemotherapy alone and to wild-type virus plus chemotherapy. Similar results will be demonstrated with tumor-targeting monoclonal antibodies in combination with these viruses.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference.
U.S. Pat. No. 4,554,101
U.S. Pat. No. 4,683,195
U.S. Pat. No. 4,683,202
U.S. Pat. No. 4,684,611
U.S. Pat. No. 4,800,159
U.S. Pat. No. 4,879,236
U.S. Pat. No. 4,883,750
U.S. Pat. No. 4,946,773
U.S. Pat. No. 4,952,500
U.S. Pat. No. 5,220,007
U.S. Pat. No. 5,279,721
U.S. Pat. No. 5,284,760
U.S. Pat. No. 5,302,523
U.S. Pat. No. 5,322,783
U.S. Pat. No. 5,354,670
U.S. Pat. No. 5,366,878
U.S. Pat. No. 5,384,253
U.S. Pat. No. 5,389,514
U.S. Pat. No. 5,399,363
U.S. Pat. No. 5,464,765
U.S. Pat. No. 5,466,468
U.S. Pat. No. 5,538,877
U.S. Pat. No. 5,538,880
U.S. Pat. No. 5,543,158
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,633,016
U.S. Pat. No. 5,635,377
U.S. Pat. No. 5,641,515
U.S. Pat. No. 5,656,610
U.S. Pat. No. 5,702,932
U.S. Pat. No. 5,736,524
U.S. Pat. No. 5,739,169
U.S. Pat. No. 5,780,448
U.S. Pat. No. 5,789,166
U.S. Pat. No. 5,789,215
U.S. Pat. No. 5,798,208
U.S. Pat. No. 5,798,339
U.S. Pat. No. 5,801,005
U.S. Pat. No. 5,824,311
U.S. Pat. No. 5,824,348
U.S. Pat. No. 5,830,650
U.S. Pat. No. 5,830,880
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,225
U.S. Pat. No. 5,846,233
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,846,945
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,871,740
U.S. Pat. No. 5,871,986
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,525
U.S. Pat. No. 5,925,565
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,819
U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,994,624
Alcami and Smith, *Cell.*, 71(1):153-67, 1992.
Alcami et al., *Sem. Virol.*, 5:419-427, 1998.

Alcami et al., *Virology*, 74(23):11230-9, 2000.
Almendro et al., *J. Immunol.*, 157(12):5411-5421, 1996.
Andoh et al., *Cancer Immunol. Immunother.*, 50(12):663-72, 2002.
Angel et al., *Mol. Cell. Biol.*, 7:2256, 1987.
Angel et al., *Cell*, 49:729, 1987b.
Angel et al., *Mol. Cell. Biol.*, 7:2256, 1987a
Arap et al., *Cancer Res.*, 55(6):1351-1354, 1995.
Atchison and Perry, *Cell*, 46:253, 1986.
Atchison and Perry, *Cell*, 48:121, 1987.
Austin-Ward and Villaseca, *Rev. Med. Chil.*, 126(7):838-45, 1998.
Ausubel et al., In: *Current Protocols in Molecular Biology*, John, Wiley & Sons, Inc, New York, 1994.
Bajorin et al., *J. Clin. Oncol.*, 6(5):786-92, 1988.
Bakhshi et al., *Cell.*, 41(3):899-906, 1985.
Baneiji et al., *Cell.*, 27(2 Pt 1):299-308, 1981.
Baneiji et al., *Cell*, 33(3):729-740, 1983.
Bellus, *J. Macromol. Sci. Pure Appl. Chem.*, A31(1): 1355-1376, 1994.
Berkhout et al., *Cell*, 59:273-282, 1989.
Blanar et al., *EMBO J.*, 8:1139, 1989.
Blasco and Moss, *J. Virology*, 66(7): 4170-4179, 1992.
Blasco et al., *J. Virology*, 67(6):3319-3325, 1993.
Bodine and Ley, *EMBO J.*, 6:2997, 1987.
Boshart et al., *Cell*, 41:521, 1985.
Bosze et al., *EMBO J.*, 5(7):1615-1623, 1986.
Boyd et al., *Cell.*, 79:341-351, 1994.
Braddock et al., *Cell*, 58:269, 1989.
Braisted and Wells, *Proc. Natl. Acad. Sci. USA*, 93(12):5688-5692, 1996.
Brizel, *Semin. Radiat. Oncol.*, 8(4):237-246, 1998.
Bukowski et al., *Clin. Cancer Res.*, 4(10):2337-47, 1998.
Bulla and Siddiqui, *J. Virol.*, 62:1437, 1986.
Burton and Barbas, *Adv. Immunol.*, 57:191-280, 1994.
Caldas et al., *Nat. Genet.*, 8(1):27-32, 1994.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Caragine et al., *Cancer Res.*, 62(4):1110-5, 2002.
Carbonelli et al., *FEMS Microbiol. Let.*, 177(1):75-82, 1999.
Celander and Haseltine, *J. Virology*, 61:269, 1987.
Celander et al., *J. Virology*, 62:1314, 1988.
Chandler et al., *Cell*, 33:489, 1983.
Chandler et al., *Proc. Natl. Acad. Sci. USA*, 94(8):3596-601, 1997.
Chang et al., *Mol. Cell. Biol.*, 9:2153, 1989.
Chattejee et al., *Proc Natl. Acad Sci. USA.*, 86:9114, 1989.
Chen and Okayama, *Mol. Cell Biol.*, 7(8):2745-2752, 1987.
Cheng et al., *Cancer Res.*, 54(21):5547-5551, 1994.
Choi et al., *Cell*, 53:519, 1988.
Christodoulides et al., *Microbiology*, 144(Pt 11):3027-37, 1998.
Cleary and Sklar, *Proc. Natl. Acad. Sci. USA*, (21):7439-7443, 1985.
Cleary et al., *J. Exp. Med.*, 164(1):315-320, 1986.
Cocea, *Biotechniques*, 23(5):814-816, 1997.
Cohen et al., *J. Cell. Physiol.*, 5:75, 1987.
Colamonici et al., *J. Biol. Chem.*, 270:15974-15978, 1995.
Cooley et al., *Science*, 239(4844):1121-1128, 1988.
Costa et al., *Mol. Cell. Biol.*, 8:81, 1988.
Cripe et al., *EMBO J.*, 6:3745, 1987.
Culotta and Hamer, *Mol. Cell. Biol.*, 9:1376, 1989.
Culver et al., *Science*, 256(5063):1550-1552, 1992.
Cunningham and Wells, *Science*, 244(4908):1081-1085, 1989
Curran, *Semin. Radiat. Oncol.*, 8(4 Suppl 1):2-4, 1998.
Dandolo et al., *J. Virology*, 47:55-64, 1983.
Davidson et al., *J. Immunother.*, 21(5):389-98, 1998.
De Villiers et al., *Nature*, 312(5991):242-246, 1984.
Deschamps et al., *Science*, 230:1174-1177, 1985.
Dillman, *Cancer Biother. Radiopharm.*, 14(1):5-10, 1999.
Dobbelstein and Shenk, *J. Virology*, 70:6479-6485, 1996.
Durrant and Spendlove, *Curr. Opin. Investig. Drugs*, 2(7): 959-66, 2001.
Edbrooke et al., *Mol. Cell. Biol.*, 9:1908, 1989.
Edlund et al., *Science*, 230:912-916, 1985.
Eliopoulos et al., *Oncogene*, 11(7):1217-28, 1995.
el-Kareh and Secomb, *Crit. Rev. Biomed. Eng.*, 25(6):503-571, 1997.
Erlandsson, *Cancer Genet. Cytogenet.*, 104(1):1-18, 1998.
European Appl. 320 308
Europe Appl. 329 822
Feng and Holland, *Nature*, 334:6178, 1988.
Firak and Subramanian, *Mol. Cell. Biol.*, 6:3667, 1986.
Foecking and Hofstetter, *Gene*, 45(1):101-105, 1986.
Fraley et al., *Proc. Natl. Acad. Sci. USA*, 76:3348-3352, 1979.
Frohman, In: *PCR Protocols: A Guide To Methods And Applications*, Academic Press, N.Y., 1990.
Fujita et al., *Cell*, 49:357, 1987.
GB Application 2 202 328
Genbank Accession NumberNC_001559
Gertig et al., *Semin. Cancer Biol.*, 8(4): 285-98, 1998.
Gilles et al., *Cell*, 33:717, 1983.
Gloss et al., *EMBO J.*, 6:3735, 1987.
Gnant et al., *Cancer Res.*, 59(14):3396-403, 1999.
Godbout et al., *Mol. Cell. Biol.*, 8:1169, 1988.
Goebel et al., *Virology*, 179(1): 247-66 and 517-63, 1990.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Graham and Van Der Eb, *Virology*, 52:456-467, 1973.
Graham et al., *Virology*, 229(1):12-24, 1997.
Greene et al., *Immunology Today*, 10:272, 1989
Gross et al., *Genes Dev.*, 13(15):1899-911, 1999.
Grosschedl and Baltimore, *Cell*, 41:885, 1985.
Hanibuchi et al., *Int J. Cancer*, 78(4):480-5, 1998.
Harland and Weintraub, *J. Cell Biol.*, 101:1094-1099, 1985.
Haslinger and Karin, *Proc. Natl. Acad. Sci. USA*, 82:8572, 1985.
Hauber and Cullen, *J. Virology*, 62:673, 1988.
Heise et al., *Cancer Gene Ther.*, 6(6):499-504, 1999.
Hellstand et al., *Acta Oncol.*, 37(4):347-353, 1998.
Hen et al., *Nature*, 321:249, 1986.
Hensel et al., *Lymphokine Res.*, 8:347, 1989.
Hermiston, *J. Clin. Invest.*, 105:1169-1172, 2000.
Herr and Clarke, *Cell.*, 45:461, 1986.
Hilton et al., *J. Biol. Chem.*, 271(9):4699-4708, 1996.
Hirochika et al., *J. Virolology*, 61:2599, 1987.
Hirsch et al., *Mol. Cell. Biol.*, 10:1959, 1990.
Ho et al., *Environ Health Perspect*, 106(5):1219-1228, 1998.
Holbrook et al., *Virology*, 157:211, 1987.
Homey et al., *Nature. Rev. Immunol.*, 2:175-184, 2002.
Horlick and Benfield, *Mol. Cell. Biol.*, 9:2396, 1989.
Huang et al., *Cell.*, 27:245, 1981.
Hug et al., *Mol. Cell. Biol.*, 8:3065, 1988.
Hui and Hashimoto, *Infect. Immun.*, 66(11):5329-36, 1998.
Hussussian et al., *Nat. Genet.*, 8(1):15-21, 1994.
Hwang et al., *Mol Cell. Biol.*, 10:585, 1990.
Ikeda et al., *Nat. Med.*, 5(8):881-7, 1999.
Imagawa et al., *Cell*, 51:251, 1987.
Imbra and Karin, *Nature*, 323:555, 1986.
Imler et al., *Mol. Cell. Biol.*, 7:2558, 1987.

Imperiale and Nevins, *Mol. Cell. Biol.*, 4:875, 1984.
Innis et al., *Proc. Natl. Acad. Sci. USA*, 85(24):9436-9440, 1988.
Inouye and Inouye, *Nucleic Acids Res.*, 13:3101-3109, 1985.
Irie and Morton, *Proc. Natl. Acad. Sci. USA*, 83(22):8694-8698, 1986.
Irie et al., *Lancet.*, 1(8641):786-787, 1989.
Isaacs et al., *Proc. Natl. Acad. Sci. USA*, 89(2):628-32, 1992.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson and Hamdy, *Oncol. Rep.*, 5(3):553-7, 1998.
Johnson et al., *Mol. Cell. Biol.*, 9:3393, 1989.
Ju et al., *J. Neuropathol. Exp. Neurol.*, 59(3):241-50, 2000.
Kadesch and Berg, *Mol. Cell. Biol.*, 6:2593, 1986.
Kaeppler et al, *Plant Cell Reports*, 9: 415-418, 1990.
Kamb et al., *Nat. Genet.*, 8(1):23-2, 1994.
Kaneda et al., *Science*, 243:375-378, 1989.
Karin et al., *Mol. Cell. Biol.*, 7:606, 1987.
Karin et al., *Mol. Cell. Biol.*, 7:606, 1987.
Katinka et al., *Cell*, 20:393, 1980.
Kato et al., *J. Biol. Chem.*, 266:3361-3364, 1991.
Kawamoto et al., *Mol. Cell. Biol.*, 8:267, 1988.
Kay et al., *Proc. Natl. Acad. Sci. USA*, 94(9):4686-91, 1997.
Kerr et al., *Br. J. Cancer*, 26(4):239-257, 1972.
Kettle et al., *J. Gen. Virology*, 78:677-685, 1997.
Kiledjian et al., *Mol. Cell. Biol.*, 8:145, 1988.
Kirn et al., *Nat. Med.*, 7(7):781-787, 2001.
Klamut et al., *Mol. Cell. Biol.*, 10:193, 1990.
Koch et al., *Mol. Cell. Biol.*, 9:303, 1989.
Kolmel, *J. Neurooncol.*, 38(2-3):121-5, 1998.
Koncz et al., *EMBO J.*, 9(5):1337-1346, 1990.
Kraus et al., *FEBS Lett.*, 428(3):165-170, 1998.
Kriegler and Botchan, *In: Eukaryotic Viral Vectors*, Gluzman (ed), Cold Spring Harbor Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Kwoh et al., *Proc. Nat. Acad. Sci. USA*, 86: 1173, 1989.
Kyte and Doolittle, *J. Mol. Biol.*, 57(1):105-32, 1982.
Lareyre et al., *J. Biol. Chem.*, 274(12):8282-8290, 1999.
Larsen et al., *Proc Natl. Acad. Sci. USA.*, 83:8283, 1986.
Laspia et al., *Cell*, 59:283, 1989.
Latiner et al., *Mol. Cell. Biol.*, 10:760, 1990.
Lee et al., *DNA Cell. Biol.*, 16(11):1267-75, 1997.
Lee et al., *Nature*, 294:228, 1981.
Lee et al., *Nucleic Acids Res.*, 12:4191-206, 1984.
Levenson et al., *Hum Gene Ther.* 20; 9(8):1233-1236, 1998.
Levinson et al., *Nature*, 295:79, 1982.
Liebermann, *Oncogene*, 17(10):1189-94, 1998.
Lin et al., *Mol. Cell. Biol.*, 10:850, 1990.
Luria et al., *EMBO J.*, 6:3307, 1987.
Lusky and Botchan, *Proc. Natl. Acad. Si. USA*, 83:3609, 1986.
Lusky et al., *Mol. Cell. Biol.* 3:1108, 1983.
Macejak and Sarnow, *Nature*, 353:90-94, 1991.
Magi-Galluzzi et al., *Anal. Quant. Cytol. Histol.*, 20(5):343-50, 1998.
Majors and Varmus, *Proc. Natl. Acad. Sci. USA*, 80:5866, 1983.
Mangray and King, *Front Biosci.*, 3:D1148-60, 1998.
Marks et al., *Symp. Soc. Exp. Biol.*, 45:77-87, 1991.
Marsters et al., *Recent Prog Horm Res*, 54:225-234, 1999.
Mayer et al., *Radiat. Oncol. Investig.*, 6(6):281-288, 1998.
McCart et al., *Gene Ther.*, 7(14):1217-23, 2000.
McNeall et al., *Gene*, 76:81, 1989.
Miksicek et al., *Cell*, 46:203, 1986.
Mitchell et al., *Ann. NY Acad. Sci.*, 690:153-166, 1993.
Mitchell et al., *J. Clin. Oncol.*, 8(5):856-869, 1990.
Mordacq and Linzer, *Genes and Dev.*, 3:760, 1989.
Moreau et al., *Nucl. Acids Res.*, 9:6047, 1981.
Mori et al., *Cancer Res.*, 54(13):3396-3397, 1994.
Morton et al., *Arch. Surg.*, 127:392-399, 1992.
Moss, In: *Fields Virology*, Fields (ed.), Lippincott-Raven Publ, Phila., 3:3637, 2672, 1996.
Moss, In: *Fields Virology*, Fields (ed.), Lippincott-Raven Publ, Phila, 3:3637-2672, 1996.
Mossman et al., *Virology*, 215(1):17-30, 1996.
Mougin et al., *Ann. Biol. Clin.*, (Paris) 56(1): 21-8, 1998.
Muesing et al., *Cell*, 48:691, 1987.
Mumby and Walter, *Cell Regul.*, 2(8):589-98, 1991.
Natoli et al., *Biochem. Pharmacol.*, 56(8):915-20, 1998.
Ng et al., *Nuc. Acids Res.*, 17:601, 1989.
Nicolau and Sene, *Biochim. Biophys. Acta*, 721:185-190, 1982.
Nicolau et al., *Methods Enzymol.*, 149:157-176, 1987.
Nielsen et al., *Cancer Gene Therapy*, 4(6):S12, 1997.
Nielsen et al., *Clin. Cancer Res.*, 4(4):835-846, 1998.
Nobori et al., *Nature*, 368(6473):753-6, 1994.
Nomoto et al., *Gene*, 236(2):259-71, 1999.
Ochi et al., *Am. J. Gastroenterol.*, 93(8): 1366-8, 1998.
Ochi et al., *Am. J. Gastroenterol.*, 93(8):1366-1368, 1998.
Ohara et al., *Proc. Natl. Acad. Sci. USA*, 86:5673-5677, 1989.
Ohara, *Gan To Kagaku Ryoho*, 25(6): 823-8, 1998.
Okamoto et al., *Proc. Natl. Acad. Sci. USA*, 1(23):11045-11049, 1994.
Omirulleh et al., *Plant Mol. Biol.*, 21(3):415-428, 1993.
Ondek et al., *EMBO J.*, 6:1017, 1987.
Orlow et al., *Cancer Res.*, 54(11):2848-2851, 1994.
Orntz et al., *Mol. Cell. Biol.*, 7:3466, 1987.
Palmiter et al., *Nature*, 300:611, 1982.
PCT Appl. PCT/US87/00880
PCT Appl. PCT/US89/01025
PCT Appl. WO 88/10315
PCT Appl. WO 89/06700
PCT Appl. WO 90/07641
PCT Appl. WO 94/09699
PCT Appl. WO 95/06128
Pech et al., *Mol. Cell. Biol.*, 9:396, 1989.
Pelletier and Sonenberg, *Nature*, 334(6180):320-325, 1988.
Perez-Stable and Constantini, *Mol. Cell. Biol.*, 10:1116, 1990.
Picard and Schaffner, *Nature*, 307:83, 1984.
Pietras et al., *Oncogene*, 17(17):2235-49, 1998.
Pietras et al., *Oncogene*, 17(17):2235-49, 1998.
Pinkert et al., *Genes and Dev.*, 1:268, 1987.
Ponta et al., *Proc Natl. Acad. Sci. USA*, 82:1020, 1985.
Porton et al., *Mol. Cell. Biol.*, 10:1076, 1990.
Potrykus et al., *Mol. Gen. Genet.*, 199:183-188, 1985.
Puhlmann, et al., *Cancer Gene Ther.*, 7(1):66-73, 2000.
Qin et al., *Proc. Natl. Acad Sci. USA*, 95(24):14411-14416, 1998.
Queen and Baltimore, *Cell*, 35:741, 1983.
Quinn et al., *Mol. Cell. Biol.*, 9:4713, 1989.
Ravindranath and Morton, *Intern. Rev. Immunol.*, 7: 303-329, 1991.
Redondo et al., *Science*, 247:1225, 1990.
Reisman and Rotter, *Mol. Cell. Biol.*, 9:3571, 1989.
Remington's Pharmaceutical Sciences" 15th Edition, pages 1035-1038 and 1570-1580
Resendez Jr. et al., *Mol. Cell. Biol.*, 8:4579, 1988.

Ripe et al., *Mol. Cell. Biol.*, 9:2224, 1989.
Rippe et al., *Mol. Cell. Biol.*, 10:689-695, 1990.
Rittling et al., *Nuc. Acids Res.*, 17:1619, 1989.
Rosel et al., *J. Virology*, 60(2):436-449, 1986.
Rosen et al., *Cell*, 41:813, 1988.
Rosenberg et al., *Ann. Surg.* 210(4):474-548, 1989.
Rosenberg et al., *N. Engl. J. Med.*, 319:1676, 1988.
Sakai et al., *Genes and Dev.*, 2:1144, 1988.
Sambrook et al., In *Molecular Cloning: A Laboratory Manual*, Second edition, Cold Spring Harbor Laboratory, Cold Spring Harbor, N.Y., 1989.
Saraiva and Alcami, *J. Virology*, 75(1):226-33, 2001.
Satake et al., *J. Virology*, 62:970, 1988.
Schaffner et al., *J. Mol. Biol.*, 201-81, 1988.
Searle et al., *Mol. Cell. Biol.*, 5:1480, 1985.
Seet et al., *Proc. Natl. Acad. Sci. USA*, 98(16):9008-13, 2001.
Serrano et al., *Nature*, 366:704-707, 1993.
Serrano et al., *Science*, 267(5195):249-252, 1995.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Sinkovics and Horvath, *J. Clin. Viro.*, 16:1-15, 2000.
Sleigh and Lockett, *J. EMBO*, 4:3831, 1985.
Smith and Vanderplasschen, *Adv. Exp. Med. Biol.*, 440:395-414, 1998.
Smith et al., *Immunol., Rev.*, 159:137-154, 1997.
Solyanik et al., *Cell. Prolif.*, 28(5):263-78, 1995.
Sommer et al. *EMBO J.*, 9(3):605-613, 1990.
Spalholz et al., *Cell*, 42:183, 1985.
Spandau and Lee, *J. Virology*, 62:427, 1988.
Spandidos and Wilkie, *EMBO J.*, 2:1193, 1983.
Spriggs et al., *Cell*, 71(1):145-52, 1992.
Stephens and Hentschel, *Biochem. J*, 248:1, 1987.
Stokke et al., *Cell Prolif.*, 30(5):197-218, 1997.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Symons et al., *Cell*, 81:551-560, 1995.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Thiesen et al., *J Virology*, 62:614, 1988.
Todo et al., *Cancer Res.*, 61:153-161, 2001.
Treisman, *Cell*, 42:889, 1985.
Tronche et al., *Mol. Biol. Med.*, 7:173, 1990.
Trudel and Constantini, *Genes and Dev.* 6:954, 1987.
Tsujimoto and Croce, et al., *Proc. Natl. Acad. Sci. USA*, 83(14):5214-5218, 1986.
Tsujimoto et al., *Science*, 228(4706):1440-1443, 1985.
Tsumaki et al., *J. Biol. Chem.*, 273(36):22861-4, 1998.
Tyndell et al., *Nuc. Acids. Res.*, 9:6231, 1981.
Upton et al., *Virology*, 184(1):370-82, 1991.
Vanderplasschen et al, *Proc. Natl. Acad. Sci. USA*, 95(13):7544-9, 1998.
Vannice and Levinson, *J. Virology*, 62:1305, 1988.
Vasseur et al., *Proc Natl. Acad. Sci. USA.*, 77:1068, 1980.
Vicari and Caus, *Cytokine Growth Factor Rev.*, 13:143-154, 2002.
Vogelstein and Kinzier, *Cell*, 70(4):523-6, 1992.
Walker et al., *Proc. Natl. Acad. Sci. USA*, 89:392-396 1992.
Wallach et al., In: *The cytokine network and immune functions*, Theze (ed.), Oxford Univ. Press, Oxford, UK, 51-84, 1999.
Wang and Calame, *Cell*, 47:241, 1986.
Warren et al., *Biochemistry*, 35(27):8855-8862, 1996.
Weber et al., *Cell*, 36:983, 1984.
Weinberger et al. *Mol. Cell. Biol.*, 8:988, 1984.
Winoto and Baltimore, *Cell* 59:649, 1989.
Wold et al., *Trends Microbiol.*, 2:437-443, 1994.
Wong et al., *Gene*, 10:87-94, 1980.
Wu and Wu, *J. Biol. Chem.*, 262:4429-4432, 1987.
Yelton et al., *J. Immunol.*, 155(4):1994-2004, 1995.
Yutzey et al. *Mol. Cell. Biol.*, 9:1397, 1989.
Zeng et al., *Biochemistry*, 35(40):13157-13164, 1996.
Zhao-Emonet et al., *Biochim. Biophys. Acta*, 1442(2-3):109-119, 1998.

The invention claimed is:

1. A method for treating a cancerous tumor in a subject comprising administering to the subject an effective amount of a vaccinia virus encoding an A34R polypeptide comprising a K151E substitution that results in increased production of an extracellular enveloped virus (EEV) form of the vaccinia virus.

2. The method of claim 1, wherein the vaccinia virus lacks at least one interferon-modulating polypeptide selected from B18R, B8R, B13R, vC12L, A53R or E3L.

3. The method of claim 1, wherein the vaccinia virus is Copenhagen or Western Reserve strain.

4. The method of claim 1, wherein the virus lacks at least one functional complement control polypeptide.

5. The method of claim 1, wherein the virus lacks at least one functional TNF-modulating polypeptide.

6. The method of claim 1, wherein the virus lacks at least one functional serine protease inhibitor.

7. The method of claim 1, wherein the virus lacks at least one functional IL-1β modulator.

8. The method of claim 1, wherein the virus is administered intravascularly.

9. The method of claim 1, wherein the subject is a human.

* * * * *